(12) United States Patent
Steber et al.

(10) Patent No.: US 9,491,916 B2
(45) Date of Patent: Nov. 15, 2016

(54) MUTATION BREEDING FOR RESISTANCE TO FUNGAL DISEASE AND FOR DROUGHT TOLERANCE

(75) Inventors: Camille Marie Steber, Pullman, WA (US); Kimberlee Kae Kidwell, Pullman, WA (US); Victor Louis Demacon, Pullman, WA (US); Patricia Ann Okubara, Pullman, WA (US)

(73) Assignees: WASHINGTON STATE UNIVERSITY, Pullman, WA (US); UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 1423 days.

(21) Appl. No.: 12/278,563

(22) PCT Filed: Feb. 7, 2007

(86) PCT No.: PCT/US2007/061805
§ 371 (c)(1),
(2), (4) Date: Sep. 2, 2008

(87) PCT Pub. No.: WO2007/092907
PCT Pub. Date: Aug. 16, 2007

(65) Prior Publication Data
US 2009/0320152 A1    Dec. 24, 2009

Related U.S. Application Data

(60) Provisional application No. 60/771,402, filed on Feb. 7, 2006, provisional application No. 60/771,285, filed on Feb. 7, 2006.

(51) Int. Cl.
*A01H 1/06* (2006.01)
*A01H 1/04* (2006.01)

(52) U.S. Cl.
CPC . *A01H 1/06* (2013.01); *A01H 1/04* (2013.01)

(58) Field of Classification Search
None
See application file for complete search history.

(56) References Cited

U.S. PATENT DOCUMENTS

| 6,137,030 | A | 10/2000 | Turner |
| 6,143,963 | A | 11/2000 | Keeling et al. |
| 7,432,082 | B2 * | 10/2008 | Zhao et al. ............. 435/91.2 |
| 2004/0216182 | A1 | 10/2004 | Federspiel et al. |
| 2005/0132439 | A1 | 6/2005 | Kogel et al. |

OTHER PUBLICATIONS

Feng et al., "Glyphospate Inhibitors Rust Disease in Glyphosate-Resistant Wheat and Soybeans," Proc. Nat. Acad. Sci., Nov. 2005, vol. 102, No. 48, abstract, p. 17290.
Chen et al., "Distuption of the Cellulose Synthase Gene, AtCesA8/IRX1, Enhances Drought and Osmotic Stress Tolerance in Arabidopsis," Planta. J. Jul. 2005, vol. 43, No. 2, abstract.

\* cited by examiner

*Primary Examiner* — Cynthia Collins
(74) *Attorney, Agent, or Firm* — Whitham, Curtis & Cook, P.C.

(57) ABSTRACT

Particular aspects provide novel mutant plants and plant parts thereof, derived via mutagenesis, having disease resistance and other useful traits. Particular embodiments provide a wheat genotype 'RRR Scarlet' ('Scarlet-Rz1'), plants and seeds thereof, methods for producing a plant comprising crossing 'Scarlet-Rz1' plants with another wheat plant, hybrid wheat seeds and plants produced by crossing 'Scarlet-Rz1' plants with another line or plant, and creation of variants by mutagenesis or transformation of 'Scarlet-Rz1'. Additional aspects provide methods for producing other varieties or breeding lines derived from 'Scarlet-Rz1' and to varieties or breeding lines produced thereby. Further aspects provide for mutant plants and plant parts thereof that are resistant and/or tolerant to plant root fungal pathogens such as *Rhizoctonia* and *Pythium*. Additional embodiments provide mutant plants and plant parts thereof that exhibit stress tolerance and/or resistance. Yet further aspects provide mutant plants and plant parts thereof that are drought resistant or tolerant.

28 Claims, 19 Drawing Sheets

Root Scan of wild type 'Scarlet' with *Rhizoctonia*

Root Scan of 'Scarlet' Mutant S-015-6-4 with *Rhizoctonia*

Highly Susceptible 'Scarlet' Mutant Line with *Rhizoctonia*

FIGURES 15A, 15B, 15C, and 15D

MUTATION BREEDING FOR RESISTANCE TO FUNGAL DISEASE AND FOR DROUGHT TOLERANCE

CROSS-REFERENCE TO RELATED APPLICATIONS

This application is a United States nationalization, pursuant to 35 U.S.C. §371, of PCT/US2007/061805 filed 7 Feb. 2007 of same title, which claims the benefit of priority from U.S. Provisional Patent Application Ser. Nos. 60/771,402, filed 7 Feb. 2006 and entitled "MUTATION BREEDING FOR RESISTANCE TO DISEASE AND OTHER USEFUL TRAITS," and 60/771,285, filed 7 Feb. 2006 and entitled "GLYPHOSATE-TOLERANT WHEAT GENOTYPE," both of which are incorporated herein by reference.

FIELD OF THE INVENTION

Aspects of the present invention relate generally to novel plants, plant parts thereof, and novel methods and compositions having substantial utility for resistance to disease and other useful traits. Particular aspects relate to wheat (*Triticum aestivum* L.) breeding, and particularly to a wheat genotype designated 'Root Rot Resistant (RRR) Scarlet' or 'Rz1' (formerly laboratory number Scarlet 015-6-4) representing the world's first *Rhizoctonia* root rot resistant gene for use in wheat improvement.

BIOLOGICAL DEPOSIT 2,500 wheat seeds derived from selection Scarlet-Rz1 (described herein) were named 'Scarlet RZ-1' (or 'Scarlet-Rz1'), were increased by self-pollination, and were deposited on 6 Feb. 2007 at 9:39 AM under the terms of the Budapest Treaty at the American Type Culture Collection, 10801 University Boulevard, Manassas, Va. 20110-2209, U.S.A., and have received ATCC Patent Deposit Number PTA-8198. Seeds from this deposit will be irrevocably made available upon the grant of a patent that makes reference to this deposit. However, the availability of these seeds is not to be construed as a license to practice the claimed invention in contravention of rights granted under the authority of any government in accordance with its patent or breeder's right laws.

BACKGROUND

Wheat is grown worldwide and is the most widely adapted cereal. There are five main wheat market classes. They include the four common wheat (*Triticum aestivum* L.) classes: hard red winter, hard red spring, soft red winter, and white. The fifth class is durum (*Triticum turgidum* L.). Common wheats are used in a variety of food products such as bread, cookies, cakes, crackers, and noodles. In general the hard wheat classes are milled into flour used for breads and the soft wheat classes are milled into flour used for pastries and crackers. Wheat starch is used in the food and paper industries, as laundry starches, and in other products. Because of its use in baking, the grain quality of wheat is very important. To test the grain quality of wheat for use as flour, milling properties are analyzed. Important milling properties are relative hardness or softness, weight per bushel of wheat (test weight), siftability of the flour, break flour yield, middlings flour yield, total flour yield, flour ash content, and wheat-to-flour protein conversion. Good processing quality for flour is also important. Good quality characteristics for flour from soft wheats include low to medium-low protein content, low water absorption, production of large-diameter test cookies and large volume cakes. Wheat glutenins and gliadins, which together confer the properties of elasticity and extensibility, play an important role in the grain quality. Changes in quality and quantity of these proteins change the end product for which the wheat can be used.

*Rhizoctonia* root rot. *Rhizoctonia* root rot is an important, yield-limiting disease in direct-seed wheat production systems. Under severe disease pressure, plants are stunted, creating bare patches in the field that can severely limit grain yield. Pathogenic *Rhizoctonia* and *Pythium* are endemic throughout the Pacific North West (PNW) of the United States and in cereal production regions in Australia and throughout the world. Disease pressure by these pathogens is also dependent upon soil type, moisture, temperature and other abiotic and biotic factors. If direct-seed systems are to succeed in the PNW and other areas where *Rhizoctonia* root rot is a problem), varieties adapted to reduced tillage or direct seed environments, and associated diseases, must be developed. Significantly, despite considerable effort, no naturally occurring *Rhizoctonia* resistant wheat plants have been identified to date (Smith, J. D., K. K. Kidwell, M. A. Evans, R. J. Cook and R. W. Smiley. 2003a, Assessment of spring wheat genotypes for disease reaction to *Rhizoctonia solani* AG-8 in controlled environment and direct-seeded field evaluations, Crop Science 43:694-700; Smith, J. D., K. K. Kidwell, M. A. Evans, R. J. Cook and R. W. Smiley. 2003b, Evaluation of spring cereal grains and wild *Triticum* germplasm for resistance to *Rhizoctonia solani* AG-8, Crop Science 43:701-709). Moreover, although differences in disease response to *Rhizoctonia* root rot have been detected among adapted spring wheat varieties, all varieties tested to date are susceptible (Smith, J. D., K. K. Kidwell, M. A. Evans, R. J. Cook and R. W. Smiley. 2003a, Assessment of spring wheat genotypes for disease reaction to *Rhizoctonia solani* AG-8 in controlled environment and direct-seeded field evaluations, Crop Science 43:694-700). Furthermore, a survey of a sub-sample of wild relatives of wheat also failed to identify a suitable resistance gene donor for *Rhizoctonia* root rot (Smith, J. D., K. K. Kidwell, M. A. Evans, R. J. Cook and R. W. Smiley. 2003b, Evaluation of spring cereal grains and wild *Triticum* germplasm for resistance to *Rhizoctonia solani* AG-8, Crop Science 43:701-709).

Mutation Breeding. Mutation Breeding comprises the use of chemical mutagenesis to increase genetic diversity. Natural mutations arise due to errors in replicating DNA. Such mutations are exploited when they are introduced from wild relatives of crop plants. The error rate during DNA replication is increased by treatment of plant seeds with chemicals called mutagens, and this chemical mutagenesis is a tool for increasing the variation in a plant population. Chemical-induced variants are currently accepted as an alternative to "Genetically Modified" plants made by transformation. Over 2,250 crop varieties now in use come from mutation breeding (M. J. Chrispeels and D. E. Sadava 2003, Plants, Genes, and Crop Biotechnology ($2^{nd}$ edition), Jones and Bartlett Publishers (Boston). Currently, for example, the herbicide-resistant Clearfield Wheat is a well-known example of a wheat variety from mutation breeding.

There is a pronounced need in the art for root rot resistant plants (e.g., wheat). There is a pronounced need in the art *Rhizoctonia* root rot resistant plants (e.g., wheat). There is a pronounced need in the art for novel methods for generating such resistant plants. There is a pronounced need in the art for novel methods comprising mutation breeding used to address the major problems that occur in wheat production (e.g., *Rhizoctonia* root rot).

SUMMARY OF PARTICULAR ASPECTS OF THE INVENTION

Particular aspect relate to a novel and distinctive wheat variety genotype, designated 'RRR Scarlet' or 'Rz1,' which is result careful breeding and selection in a wheat mutation breeding program.

Particular embodiments provide novel mutant plants and plant parts thereof derived via chemical mutagenesis comprising disease resistance and other useful plant traits.

Additional embodiments include a wheat variety genotype designated 'RRR Scarlet' or 'Rz1,' the plants and seeds thereof.

Further embodiments provide methods for producing a wheat plant produced by crossing the variety genotype 'RRR Scarlet' ('Rz1') with another wheat plant, and hybrid wheat seeds and plants produced by crossing the genotype 'RRR Scarlet' ('Rz1') with another wheat line or plant, and the creation of variants by mutagenesis or transformation of genotype 'RRR Scarlet' ('Rz1').

Additional aspects comprise methods for producing other wheat varieties or breeding lines derived from wheat variety 'RRR Scarlet' ('Rz1') and to wheat varieties or breeding lines produced by those methods.

Further aspects provide for mutant plants and plant parts thereof that are resistant and/or tolerant to plant pathogens such as *Rhizoctonia* and *Pythium*. As used herein, the term "plant parts" includes plant protoplasts, plant cell tissue cultures from which wheat plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, and the like. The term also includes products of a plant, including but not limited to flour, starch, oil, wheat germ, and so on.

In more particular aspects, the invention comprises mutant plants and plant parts thereof that are tolerant to the root pathogens *Rhizoctonia solani, Rhizoctonia oryzae, Pythium ultimum*, and *Pythium irregulare*.

Certain aspects provide methods using chemical mutagens to increase the genetic diversity within the spring wheat cultivars (e.g., Zak and Scarlet), wherein mutagenized cultivars (e.g., Zak and Scarlet) are screened for mutations that give them greater resistance to *Rhizoctonia* and/or *Pythium*.

Additional embodiments comprise methods for the recovery of a novel genetic change in gene(s) conferring the desired response (resistance gene) 'RRR Scarlet' ('Rz1') with little disruption to the remaining genetic pathways. Thus, according to particular aspects, mutated cultivars (e.g., Zak and Scarlet) and plants with resistance are genetically similar to the respective parent with the advantage of the new resistance gene.

Particular preferred aspects provide a wheat plant or a part thereof, comprising a mutation that confers fungal tolerance derived from a root fungal pathogen-tolerant wheat genotype resulting from chemical mutagenesis of wheat germplasm. In certain embodiments, the chemical mutagenesis comprises treatment of wheat seeds with ethyl methane sulfonate (EMS). In particular embodiments, the root fungal pathogen-tolerant wheat genotype is Scarlet-Rz1 (ATCC Patent Deposit Number PTA-8198). In particular aspects, the fungus-tolerance trait is derived by crossing a plant of the root fungal pathogen-tolerant wheat genotype with a plant of a wheat variety that lacks the root fungal pathogen-tolerance trait to produce progeny, and selecting the wheat plant comprising the root fungal pathogen-tolerance trait from the progeny.

In certain aspects, the root fungal pathogen-tolerant wheat genotype is tolerant to at least one root fungal pathogen selected from the group consisting of *Rhizoctonia* and *Pythium*. In particular embodiments, the *Rhizoctonia* spp comprises at least one selected from the group consisting of *R. solani* and *R. oryzae*. In certain embodiments, the *Pythium* spp comprises at least one selected from the group consisting of *P. ultimum, P. irregulare, P. debaryanum, P. aristosporum, P. volutum*, and *P. sylvaticum*.

In particular embodiments, the root fungal pathogen-tolerant wheat genotype comprises a semi-dominant mutation. In certain aspects, the wheat plant or part thereof comprises two or more different mutations that confer root fungal pathogen-tolerance, wherein at least one of the two or more different mutations is derived from a root fungal pathogen-tolerant wheat genotype resulting from chemical mutagenesis of wheat germplasm. In particular aspects, each of the two or more different mutations is derived from a root fungal pathogen-tolerant wheat genotype resulting from chemical mutagenesis of wheat germplasm. In particular aspects, at least one of the two or more different mutations comprises a semi-dominant mutation. In particular embodiments, the root fungal pathogen-tolerant wheat genotype is tolerant to at least one root fungal pathogen selected from the group consisting of *Rhizoctonia* and *Pythium*.

In particular aspects, the wheat plant or part thereof further comprises at least one trait selected from the group consisting of: male sterility, resistance to an herbicide, insect resistance, disease resistance; waxy starch; modified fatty acid metabolism, modified phytic acid metabolism, modified carbohydrate metabolism, modified waxy starch content, modified gluten content, and modified water stress tolerance. In certain aspects, the herbicide consists of or comprises glyphosate or a derivative thereof. In particular embodiments, the resistance to herbicide, is derived from a glyphosate-tolerant wheat genotype selected from the group consisting of GT-Louise, LouiseFR1-04, LouiseFR1-33, MaconFR1-05, MaconFR1-19 and TaraFR1-07.

Additional aspects provide a seed of a root fungal pathogen-tolerant wheat genotype, wherein the root fungal pathogen-tolerant wheat genotype resulting from chemical mutagenesis of wheat germplasm. In certain aspects, the chemical mutagenesis comprises treatment of wheat seeds with ethyl methane sulfonate (EMS). In particular aspects, the root fungal pathogen-tolerant wheat genotype is Scarlet-Rz1 (ATCC Patent Deposit Number PTA-8198).

Additional aspects provide a true-breeding seed of any of the above described plants. Further embodiments provide a wheat plant or part thereof produced by growing the seed of claim 19. Yet additional aspects provide a wheat plant or part thereof having all the physiological and morphological characteristics of a Scarlet-Rz1 (ATCC Patent Deposit Number PTA-8198) genotype.

Further aspects provide a method of making a root fungal pathogen-tolerant wheat genotype or wheat plant, comprising: providing germplasm of a wheat variety; treating the germplasm with a mutagen to produce a mutagenized germplasm; selecting from the mutagenized germplasm a root fungal pathogen-tolerant wheat seed comprising a genotype conferring root fungal pathogen-tolerance that is caused by the mutagen; and growing a root fungal pathogen-tolerant wheat plant from the root fungal pathogen-tolerant wheat seed. In certain aspects the germplasm comprises a plurality of seeds. In additional aspect the germplasm comprises wheat microspores. In certain embodiments, the mutagen is a chemical mutagen. In particular embodiments, the chemical mutagen is ethyl methane sulfonate (EMS). In particular aspects, the genotype conferring root fungal pathogen-tolerance comprises at least one mutation selected from the group consisting of a point mutation and a deletion mutation. In certain embodiments, the genotype conferring root fungal pathogen-tolerance comprises a semi-dominant mutation. In particular aspects, the root fungal pathogen-tolerant wheat seed is identified by growing the root fungal pathogen-tolerant plant from the root fungal pathogen-tolerant wheat seed under conditions suitable to expose roots thereof to a root fungal pathogen, and observing the roots or the growth of the root fungal pathogen-tolerant plant during or after exposure to the root fungal pathogen. In certain embodiments, the root fungal pathogen-tolerant wheat genotype or plant is tolerant to at least one root fungal pathogen selected from the group consisting of Rhizoctonia and Pythium. In certain embodiments, the Rhizoctonia spp comprises at least one selected from the group consisting of R. solani and R. oryzae. In particular embodiments, the Pythium spp comprises at least one selected from the group consisting of P. ultimum, P. irregulare, P. debaryanum, P. aristosporum, P. volutum, and P. sylvaticum. In certain embodiments, the root fungal pathogen-tolerant wheat plant is phenotypically similar to an unmutagenized wheat plant of the selected wheat variety.

Yet further aspects, provide a method of making a root fungal pathogen-tolerant wheat genotype or wheat plant, comprising: providing a plurality of seeds of a selected wheat variety; treating the plurality of wheat seeds with a chemical mutagen to produce a mutagenized germplasm; selecting from the plurality of mutagenized wheat seeds a root fungal pathogen-tolerant wheat seed comprising a genotype conferring root fungal pathogen-tolerance that is caused by the mutagen; and growing a root fungal pathogen-tolerant wheat plant from the root fungal pathogen-tolerant wheat seed, wherein the root fungal pathogen-tolerant wheat plant is phenotypically similar to an unmutagenized wheat plant of the selected wheat variety. In certain embodiments, the root fungal pathogen-tolerant wheat genotype or plant is tolerant to at least one root fungal pathogen selected from the group consisting of Rhizoctonia and Pythium. In particular embodiments, the Rhizoctonia spp comprises at least one selected from the group consisting of R. solani and R. oryzae.

Additional embodiments provide a method of producing a root fungal pathogen-tolerant wheat genotype or plant, comprising: crossing a plant of a selected wheat variety with a root fungal pathogen-tolerant wheat plant having a genotype derived from a root fungal pathogen-tolerant wheat genotype resulting from chemical mutagenesis of wheat germplasm, thereby producing a plurality of progeny; and selecting a progeny that is root fungal pathogen-tolerant. In certain embodiments, the chemical mutagenesis comprises treatment of wheat seeds with ethyl methane sulfonate (EMS). In certain embodiments, the root fungal pathogen-tolerant wheat genotype is that of Scarlet-Rz1 (ATCC Patent Deposit Number PTA-8198).

In certain embodiments, the method comprises: (a) crossing plants grown from seed of the root fungal pathogen-tolerant wheat genotype, with plants of the selected wheat variety to produce F1 progeny plants; (b) selecting F1 progeny plants that have the root fungal pathogen-tolerance trait; (c) crossing the selected F1 progeny plants with the plants of the selected wheat variety to produce backcross progeny plants; (d) selecting for backcross progeny plants that have the root fungal pathogen-tolerance trait and physiological and morphological characteristics of said selected wheat genotype to produce selected backcross progeny plants; and (e) repeating steps (c) and (d) three or more times in succession to produce selected fourth or higher backcross progeny plants that comprise the root fungal pathogen-tolerance trait and physiological and morphological characteristics of said selected wheat genotype as determined at the 5% significance level when grown in the same environmental conditions.

In certain aspects, the method comprises: (a) crossing plants grown from seed of the root fungal pathogen-tolerant wheat genotype, with plants of said selected wheat variety to produce F1 progeny plants, wherein the selected wheat variety comprises a desired trait; (b) selecting F1 progeny plants that have the desired trait to produce selected F1 progeny plants; (c) crossing the selected progeny plants with the plants of the root fungal pathogen-tolerant wheat genotype to produce backcross progeny plants; (d) selecting for backcross progeny plants that have the desired trait and physiological and morphological characteristics of the root fungal pathogen-tolerant wheat genotype to produce selected backcross progeny plants; and (e) repeating steps (c) and (d) three or more times in succession to produce selected fourth or higher backcross progeny plants that comprise the desired trait and physiological and morphological characteristics of said root fungal pathogen-tolerant wheat genotype as determined at the 5% significance level when grown in the same environmental conditions. In certain embodiments, the desired trait comprises at least one selected from the group consisting of: male sterility, resistance to an herbicide, insect resistance, disease resistance; waxy starch; modified fatty acid metabolism, modified phytic acid metabolism, modified carbohydrate metabolism, modified waxy starch content, modified gluten content, and modified water stress tolerance.

In certain embodiments of the methods, the herbicide consists of or comprises glyphosate or a derivative thereof. In particular aspects, the resistance to herbicide, is derived from a glyphosate-tolerant wheat genotype selected from the group consisting of GT-Louise, LouiseFR1-04, LouiseFR1-33, MaconFR1-05, MaconFR1-19 and TaraFR1-07.

Yet further aspects provide a method of producing a root fungal pathogen-tolerant wheat genotype or plant, comprising; providing a selected wheat variety; and introducing into the selected wheat variety using suitable methods a transgene comprising a mutation that confers fungal tolerance, the mutation derived from a root fungal pathogen-tolerant wheat genotype resulting from chemical mutagenesis of wheat germplasm. In certain embodiments, the chemical mutagenesis comprises treatment of wheat seeds with ethyl methane sulfonate (EMS). In certain embodiments, the root fungal pathogen-tolerant wheat genotype from which the mutation is derived is Scarlet-Rz1 (ATCC Patent Deposit Number PTA-8198). Additional aspects provide transgenic plants obtained by introducing such transgenes.

Additional aspects proved a method of making a drought-tolerant wheat genotype or wheat plant, comprising: providing germplasm of a wheat variety; treating the germplasm with a mutagen to produce a mutagenized germplasm; selecting from the mutagenized germplasm a drought-tolerant wheat seed comprising a genotype conferring drought-tolerance that is caused by the mutagen; and growing a drought-tolerant wheat plant from the drought-tolerant wheat seed. In certain embodiments, the germplasm comprises a plurality of seeds. In particular embodiments, the mutagen is a chemical mutagen. In certain aspects, the chemical mutagen comprises or consists of ethyl methane sulfonate (EMS). In particular embodiments, the drought-tolerant wheat seed is identified based on increased sensitivity to the plant hormone ABA (abscisic acid) during seed germination.

BRIEF DESCRIPTION OF THE DRAWINGS

FIG. 7A shows wild type Scarlet (Wt) without *Rhizoctonia* treatment. FIG. 7D shows mean root lengths of 24 plants from each of the above treatments.

DETAILED DESCRIPTION OF THE INVENTION

Figure 1:
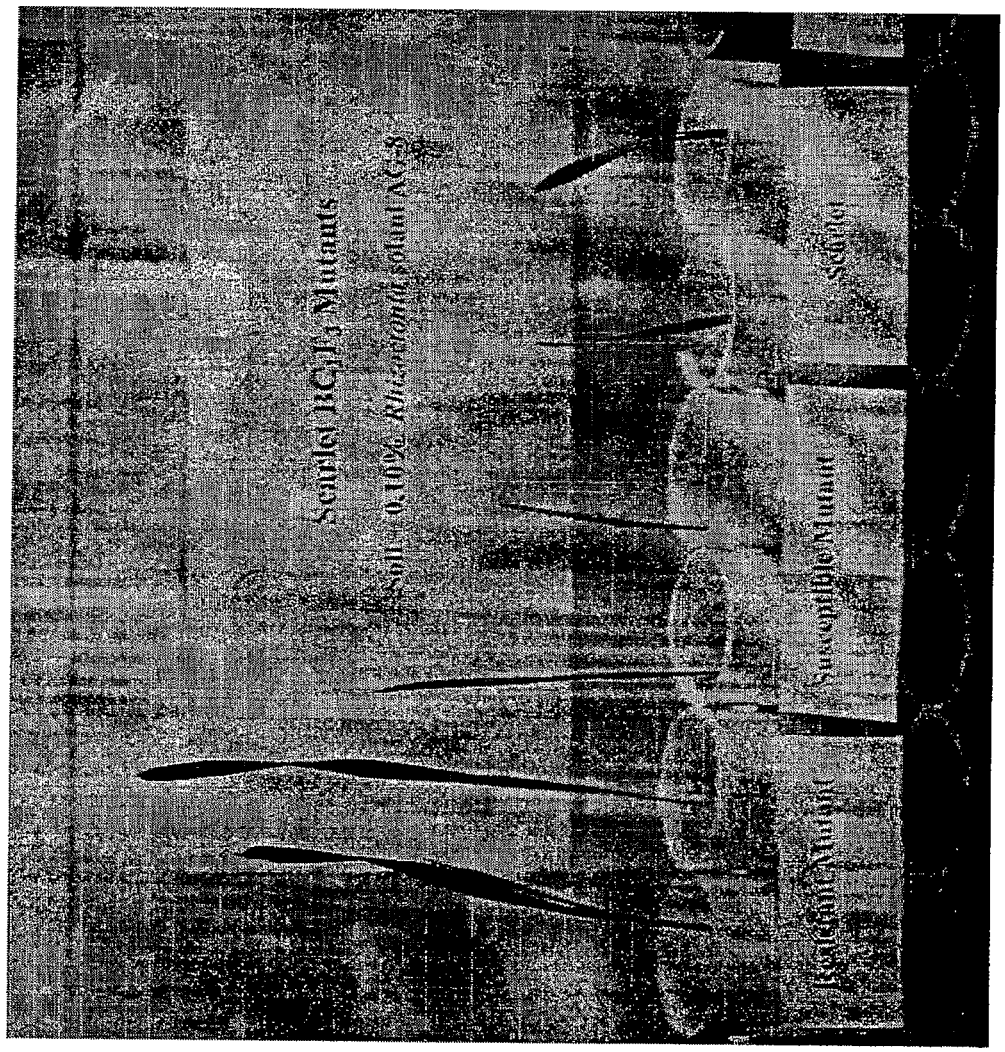
FIG. 1 shows, according to particular exemplary embodiments of the present invention, growth chamber evaluated wheat seedlings with and without *Rhizoctonia solani* inoculum at the M1 stage. The resistant mutant RRR Scarlet is in the two containers in the far left of the photograph, a susceptible mutant is found in containers 3 and 4, and the control Scarlet, with and without *Rhizoctonia* inoculum, is found in containers 5 and 6, and 7 and 8, respectively. Seedling height is significantly correlated with disease infection levels. RRR Scarlet is similar in height to the non-inoculated control. RRR Scarlet is variously referred to as Resistant Mutant, Scarlet Mutant Line 15, S 015 or S 015-6-4 in the figure.
Figure 2:
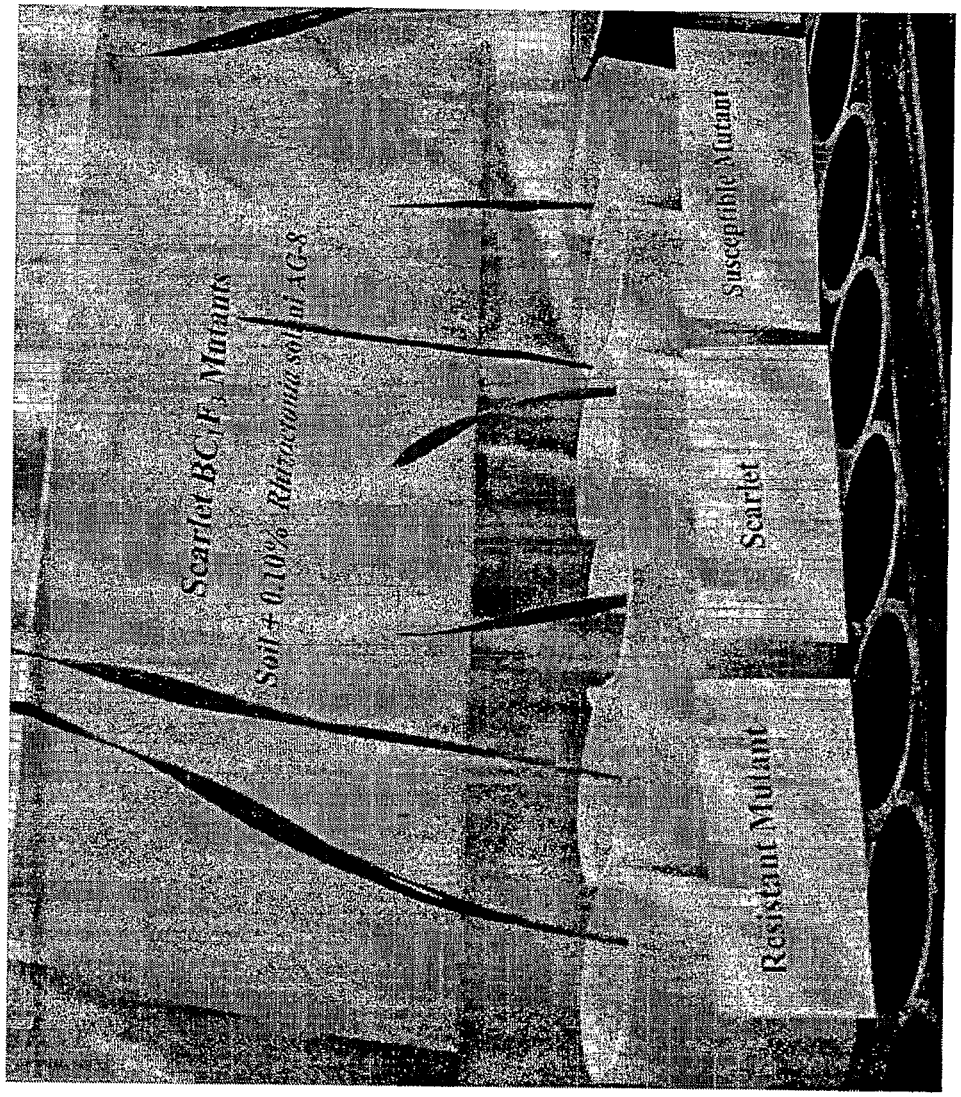
FIG. 2 shows, according to particular exemplary embodiments of the present invention, growth chamber evaluated wheat seedling with and without *Rhizoctonia solani* inoculum at the $BC_1F_3$ (pedigree=Scarlet2*RRR Scarlet) stage. Reading from left to right, $BC_1$ derivatives of RRR Scarlet are found in cones 1 and 2, inoculated Scarlet is in cones 3 and 4, $BC_1$ derivatives of a susceptible mutant are found in cones 5 and 6, and un-inoculated Scarlet is found in cones 7 and 8. RRR Scarlet is similar in height to the un-inoculated control indicating that this genotype is tolerant to the pathogen, and that this resistance is heritable. RRR Scarlet is variously referred to as Resistant Mutant, Scarlet Mutant Line 15, S 015 or S 015-6-4 in the figure.
Figure 3A:
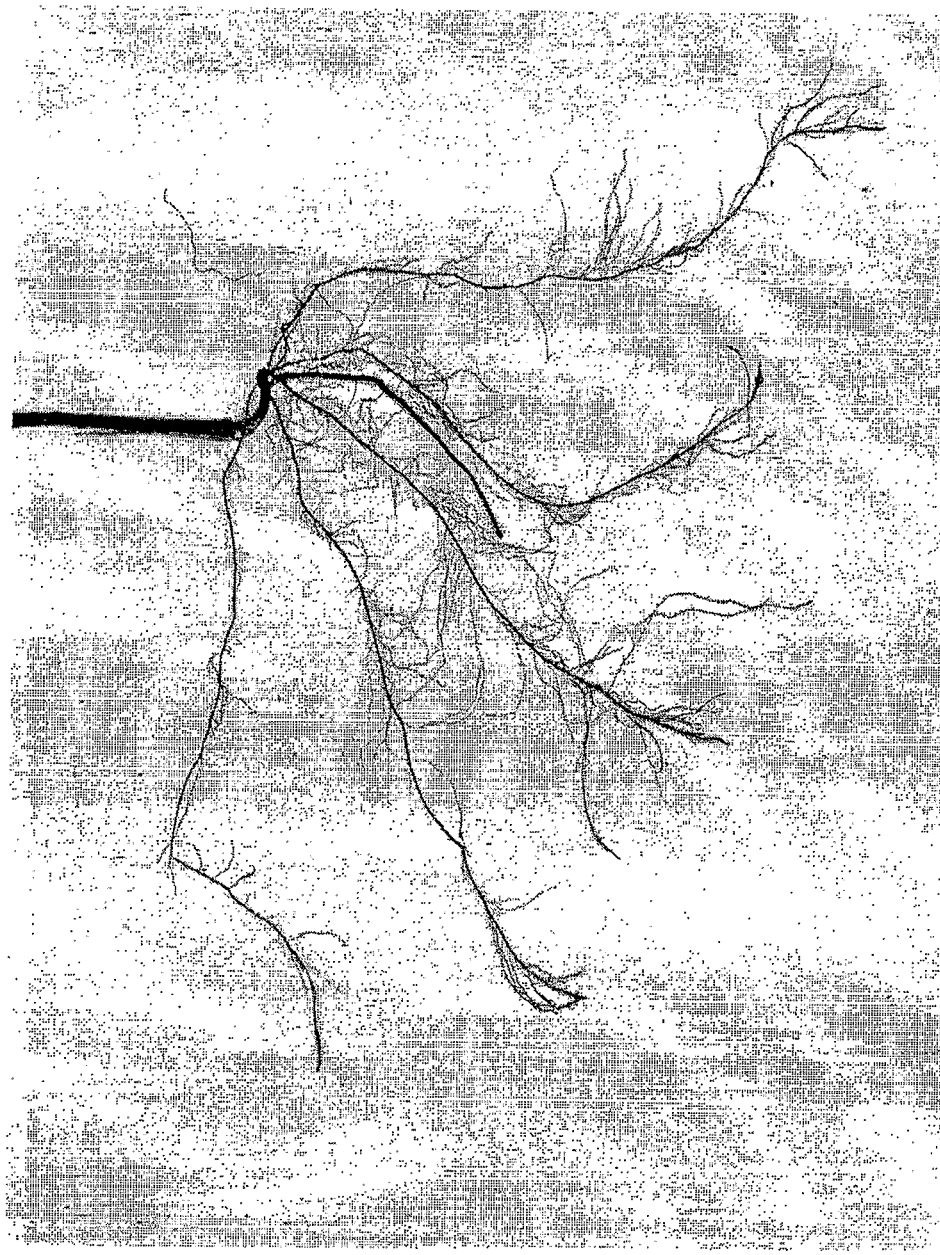
FIG. 3 shows, according to particular exemplary embodiments of the present invention, root scans, which reflect root health, of Scarlet and RRR Scarlet treated with or without *Rhizoctonia solani*. Large root mass is associated with low disease levels. A) Scarlet without inoculum; B) Scarlet with inoculum; C) Scarlet-015-6-4 with inoculum; and D) highly susceptible mutant line with inoculum. The root mass of inoculated Scarlet-015-6-4 is similar to that of un-inoculated Scarlet. RRR Scarlet is variously referred to as Resistant Mutant, Scarlet Mutant Line 15, S 015 or S 015-6-4 in the figure.
Figure 3B:
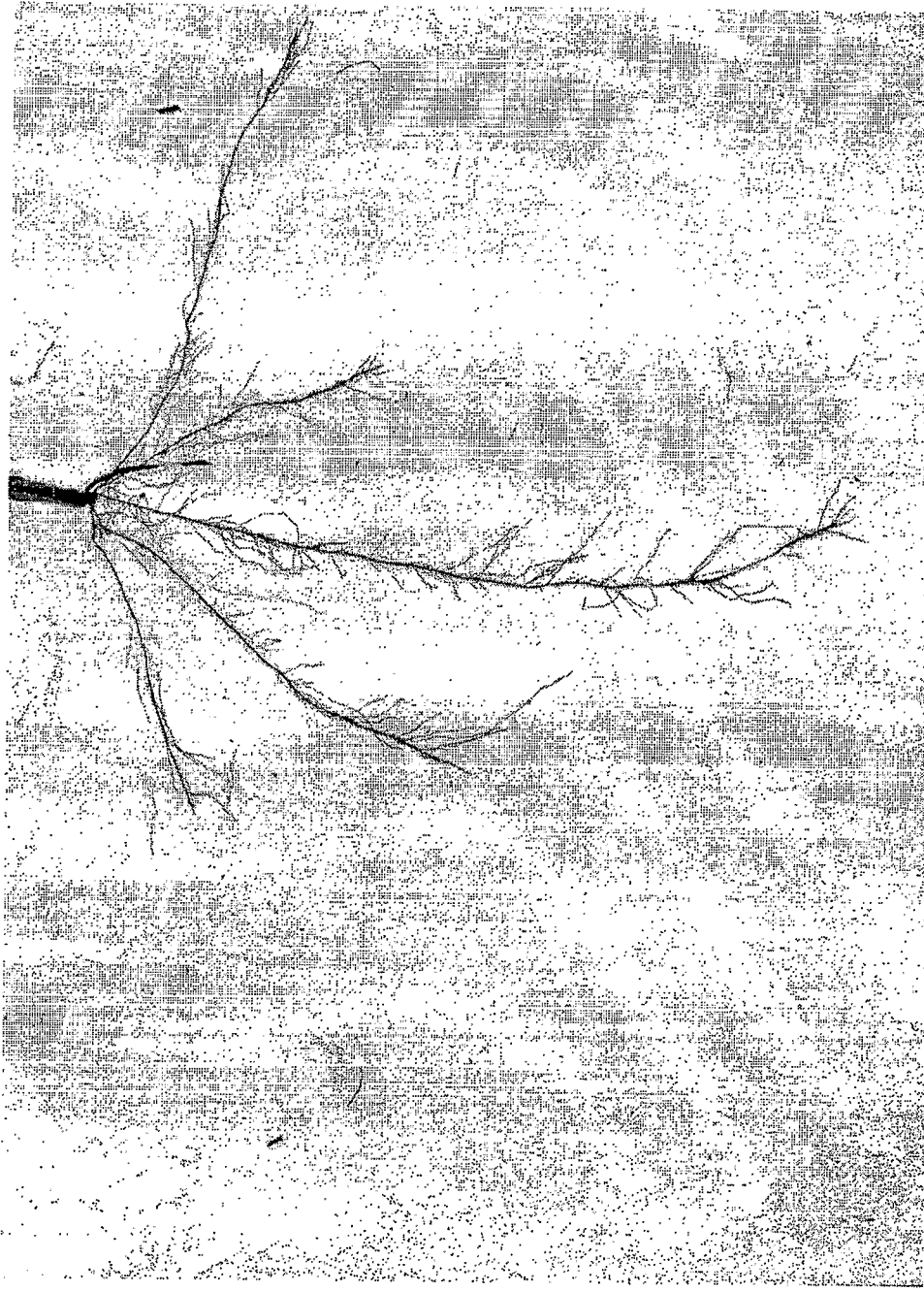
Figure 3C:
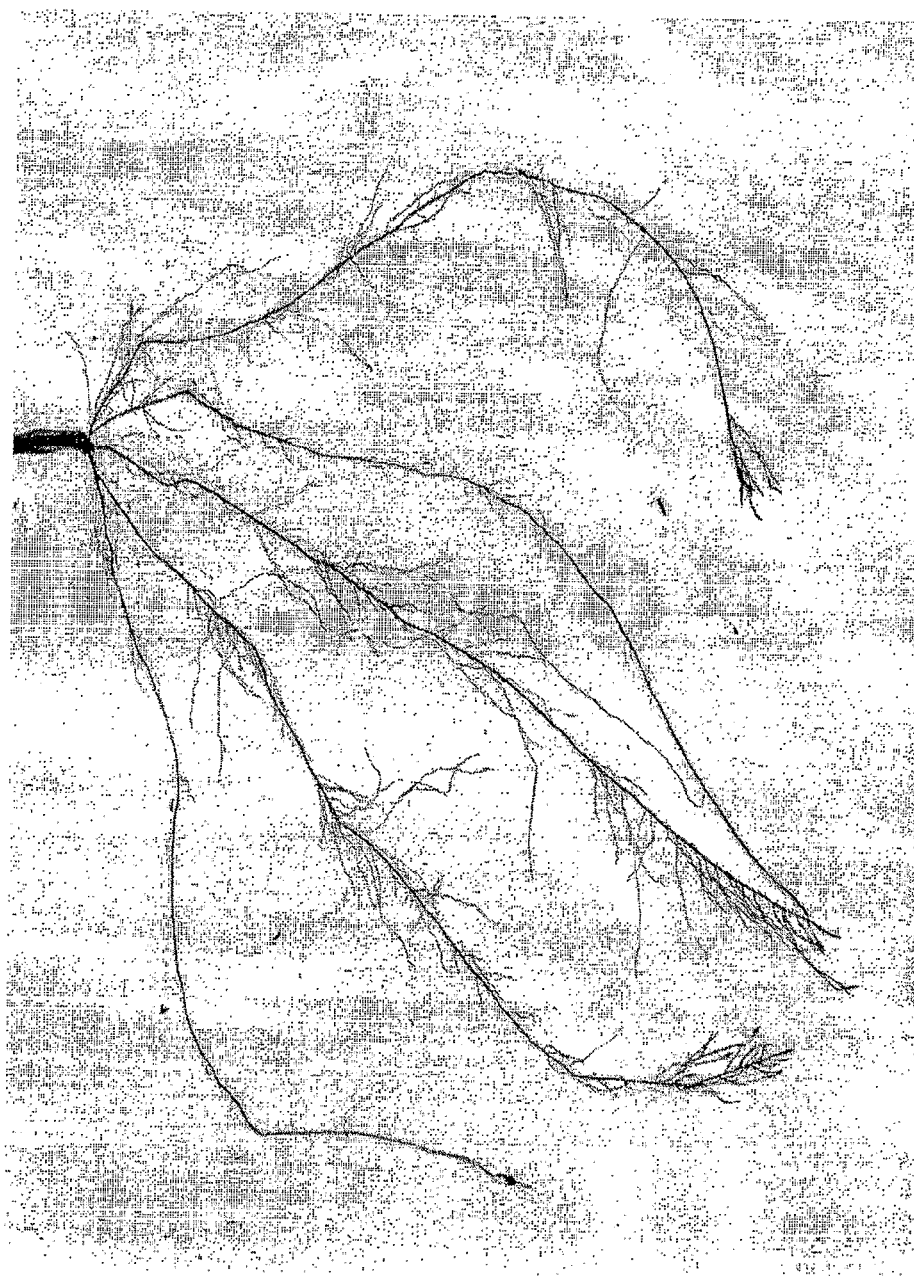
Figure 3D:

Embodiments of the invention comprise the treatment of a wheat plant with a mutagen and the plant produced by mutagenesis of the wheat plant. Information about mutagens and mutagenizing seeds or pollen are presented in the IAEA's *Manual on Mutation Breeding* (IAEA, 1977) other information about mutation breeding in wheat can be found in C. F. Konzak, "Mutations and Mutation Breeding" chapter 7B, of *Wheat and Wheat Improvement,* 2$^{nd}$ edition, ed. Heyne, 1987.

Exemplary Preferred Embodiments:

Particular aspects provide a wheat plant or a part thereof, comprising a mutation that confers fungal tolerance derived from a root fungal pathogen-tolerant wheat genotype resulting from chemical mutagenesis of wheat germplasm. In certain embodiments, the chemical mutagenesis comprises treatment of wheat seeds with ethyl methane sulfonate (EMS). In particular embodiments, the root fungal pathogen-tolerant wheat genotype is Scarlet-Rz1 (ATCC Patent Deposit Number PTA-8198). In particular aspects, the fungus-tolerance trait is derived by crossing a plant of the root fungal pathogen-tolerant wheat genotype with a plant of a wheat variety that lacks the root fungal pathogen-tolerance trait to produce progeny, and selecting the wheat plant comprising the root fungal pathogen-tolerance trait from the progeny.

In certain aspects, the root fungal pathogen-tolerant wheat genotype is tolerant to at least one root fungal pathogen selected from the group consisting of *Rhizoctonia* and *Pythium*. In particular embodiments, the *Rhizoctonia* spp comprises at least one selected from the group consisting of *R. solani* and *R. oryzae*. In certain embodiments, the *Pythium* spp comprises at least one selected from the group consisting of *P. ultimum, P. irregulare, P. debaryanum, P. aristosporum, P. volutum,* and *P. sylvaticum*.

In particular embodiments, the root fungal pathogen-tolerant wheat genotype comprises a semi-dominant mutation. In certain aspects, the wheat plant or part thereof comprises two or more different mutations that confer root fungal pathogen-tolerance, wherein at least one of the two or more different mutations is derived from a root fungal pathogen-tolerant wheat genotype resulting from chemical mutagenesis of wheat germplasm. In particular aspects, each of the two or more different mutations is derived from a root fungal pathogen-tolerant wheat genotype resulting from chemical mutagenesis of wheat germplasm. In particular aspects, at least one of the two or more different mutations comprises a semi-dominant mutation. In particular embodiments, the root fungal pathogen-tolerant wheat genotype is tolerant to at least one root fungal pathogen selected from the group consisting of *Rhizoctonia* and *Pythium*.

In particular aspects, the wheat plant or part thereof further comprises at least one trait selected from the group consisting of: male sterility, resistance to an herbicide, insect resistance, disease resistance; waxy starch; modified fatty acid metabolism, modified phytic acid metabolism, modified carbohydrate metabolism, modified waxy starch content, modified gluten content, and modified water stress tolerance. In certain aspects, the herbicide consists of or comprises glyphosate or a derivative thereof. In particular embodiments, the resistance to herbicide, is derived from a glyphosate-tolerant wheat genotype selected from the group consisting of GT-Louise, LouiseFR1-04, LouiseFR1-33, MaconFR1-05, MaconFR1-19 and TaraFR1-07.

Additional aspects provide a seed of a root fungal pathogen-tolerant wheat genotype, wherein the root fungal pathogen-tolerant wheat genotype resulting from chemical mutagenesis of wheat germplasm. In certain aspects, the chemical mutagenesis comprises treatment of wheat seeds with ethyl methane sulfonate (EMS). In particular aspects, the root fungal pathogen-tolerant wheat genotype is Scarlet-Rz1 (ATCC Patent Deposit Number PTA-8198).

Additional aspects provide a true-breeding seed of any of the above described plants.

Further embodiments provide a wheat plant or part thereof produced by growing the seed of claim 19.

Yet additional aspects provide a wheat plant or part thereof having all the physiological and morphological characteristics of a Scarlet-Rz1 (ATCC Patent Deposit Number PTA-8198) genotype.

Further aspects provide a method of making a root fungal pathogen-tolerant wheat genotype or wheat plant, comprising: providing germplasm of a wheat variety; treating the germplasm with a mutagen to produce a mutagenized germplasm; selecting from the mutagenized germplasm a root fungal pathogen-tolerant wheat seed comprising a genotype conferring root fungal pathogen-tolerance that is caused by the mutagen; and growing a root fungal pathogen-tolerant wheat plant from the root fungal pathogen-tolerant wheat seed. In certain aspects the germplasm comprises a plurality of seeds. In additional aspect the germplasm comprises wheat microspores. In certain embodiments, the mutagen is a chemical mutagen. In particular embodiments, the chemical mutagen is ethyl methane sulfonate (EMS). In particular aspects, the genotype conferring root fungal pathogen-tolerance comprises at least one mutation selected from the group consisting of a point mutation and a deletion mutation. In certain embodiments, the genotype conferring root fungal pathogen-tolerance comprises a semi-dominant mutation. In particular aspects, the root fungal pathogen-tolerant wheat seed is identified by growing the root fungal pathogen-tolerant plant from the root fungal pathogen-tolerant wheat seed under conditions suitable to expose roots thereof to a root fungal pathogen, and observing the roots or the growth of the root fungal pathogen-tolerant plant during or after exposure to the root fungal pathogen. In certain embodiments, the root fungal pathogen-tolerant wheat genotype or plant is tolerant to at least one root fungal pathogen selected from the group consisting of *Rhizoctonia* and *Pythium*. In certain embodiments, the *Rhizoctonia* spp comprises at least one selected from the group consisting of *R. solani* and *R. oryzae*. In particular embodiments, the *Pythium* spp comprises at least one selected from the group consisting of *P. ultimum, P. irregulare, P. debaryanum, P. aristosporum, P. volutum,* and *P. sylvaticum*. In certain embodiments, the root fungal pathogen-tolerant wheat plant is phenotypically similar to an unmutagenized wheat plant of the selected wheat variety.

Yet further aspects, provide a method of making a root fungal pathogen-tolerant wheat genotype or wheat plant, comprising: providing a plurality of seeds of a selected wheat variety; treating the plurality of wheat seeds with a chemical mutagen to produce a mutagenized germplasm; selecting from the plurality of mutagenized wheat seeds a root fungal pathogen-tolerant wheat seed comprising a genotype conferring root fungal pathogen-tolerance that is caused by the mutagen; and growing a root fungal pathogen-tolerant wheat plant from the root fungal pathogen-tolerant wheat seed, wherein the root fungal pathogen-tolerant wheat plant is phenotypically similar to an unmutagenized wheat plant of the selected wheat variety. In certain embodiments, the root fungal pathogen-tolerant wheat genotype or plant is tolerant to at least one root fungal pathogen selected from the group consisting of *Rhizoctonia* and *Pythium*. In particular embodiments, the *Rhizoctonia* spp comprises at least one selected from the group consisting of *R. solani* and *R. oryzae*.

Additional embodiments provide a method of producing a root fungal pathogen-tolerant wheat genotype or plant, comprising: crossing a plant of a selected wheat variety with a root fungal pathogen-tolerant wheat plant having a genotype derived from a root fungal pathogen-tolerant wheat genotype resulting from chemical mutagenesis of wheat germplasm, thereby producing a plurality of progeny; and selecting a progeny that is root fungal pathogen-tolerant. In certain embodiments, the chemical mutagenesis comprises treatment of wheat seeds with ethyl methane sulfonate (EMS). In certain embodiments, the root fungal pathogen-tolerant wheat genotype is that of Scarlet-Rz1 (ATCC Patent Deposit Number PTA-8198).

In certain embodiments, the method comprises: (a) crossing plants grown from seed of the root fungal pathogen-tolerant wheat genotype, with plants of the selected wheat variety to produce F1 progeny plants; (b) selecting F1 progeny plants that have the root fungal pathogen-tolerance trait; (c) crossing the selected F1 progeny plants with the plants of the selected wheat variety to produce backcross progeny plants; (d) selecting for backcross progeny plants that have the root fungal pathogen-tolerance trait and physiological and morphological characteristics of said selected wheat genotype to produce selected backcross progeny plants; and (e) repeating steps (c) and (d) three or more times in succession to produce selected fourth or higher backcross progeny plants that comprise the root fungal pathogen-tolerance trait and physiological and morphological characteristics of said selected wheat genotype as determined at the 5% significance level when grown in the same environmental conditions.

In certain aspects, the method comprises: (a) crossing plants grown from seed of the root fungal pathogen-tolerant wheat genotype, with plants of said selected wheat variety to produce F1 progeny plants, wherein the selected wheat variety comprises a desired trait; (b) selecting F1 progeny plants that have the desired trait to produce selected F1 progeny plants; (c) crossing the selected progeny plants with the plants of the root fungal pathogen-tolerant wheat genotype to produce backcross progeny plants; (d) selecting for backcross progeny plants that have the desired trait and physiological and morphological characteristics of the root fungal pathogen-tolerant wheat genotype to produce selected backcross progeny plants; and (e) repeating steps (c) and (d) three or more times in succession to produce selected fourth or higher backcross progeny plants that comprise the desired trait and physiological and morphological characteristics of said root fungal pathogen-tolerant wheat genotype as determined at the 5% significance level when grown in the same environmental conditions. In certain embodiments, the desired trait comprises at least one selected from the group consisting of: male sterility, resistance to an herbicide, insect resistance, disease resistance; waxy starch; modified fatty acid metabolism, modified phytic acid metabolism, modified carbohydrate metabolism, modified waxy starch content, modified gluten content, and modified water stress tolerance.

In certain embodiments of the methods, the herbicide consists of or comprises glyphosate or a derivative thereof. In particular aspects, the resistance to herbicide, is derived from a glyphosate-tolerant wheat genotype selected from the group consisting of GT-Louise, LouiseFR1-04, LouiseFR1-33, MaconFR1-05, MaconFR1-19 and TaraFR1-07.

Yet further aspects provide a method of producing a root fungal pathogen-tolerant wheat genotype or plant, comprising; providing a selected wheat variety; and introducing into the selected wheat variety using suitable methods a transgene comprising a mutation that confers fungal tolerance, the mutation derived from a root fungal pathogen-tolerant wheat genotype resulting from chemical mutagenesis of wheat germplasm. In certain embodiments, the chemical mutagenesis comprises treatment of wheat seeds with ethyl methane sulfonate (EMS). In certain embodiments, the root fungal pathogen-tolerant wheat genotype from which the mutation is derived is Scarlet-Rz1 (ATCC Patent Deposit Number PTA-8198). Additional aspects provide transgenic plants obtained by introducing such transgenes.

Additional aspects proved a method of making a drought-tolerant wheat genotype or wheat plant, comprising: providing germplasm of a wheat variety; treating the germplasm with a mutagen to produce a mutagenized germplasm; selecting from the mutagenized germplasm a drought-tolerant wheat seed comprising a genotype conferring drought-tolerance that is caused by the mutagen; and growing a drought-tolerant wheat plant from the drought-tolerant wheat seed. In certain embodiments, the germplasm comprises a plurality of seeds. In particular embodiments, the mutagen is a chemical mutagen. In certain aspects, the chemical mutagen comprises or consists of ethyl methane sulfonate (EMS). In particular embodiments, the drought-tolerant wheat seed is identified based on increased sensitivity to the plant hormone ABA (abscisic acid) during seed germination.

Backcross Conversion

An additional embodiment comprises or is a backcross conversion of wheat variety genotype 'RRR Scarlet' ('Rz1'). A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to nutritional enhancements, industrial enhancements, disease resistance, insect resistance, herbicide resistance, agronomic enhancements, grain quality enhancement, waxy starch, breeding enhancements, seed production enhancements, and male sterility. Descriptions of some of the cytoplasmic male sterility genes, nuclear male sterility genes, chemical hybridizing agents, male fertility restoration genes, and methods of using the aforementioned are discussed in "Hybrid Wheat" by K. A. Lucken (pp. 444-452 In *Wheat and Wheat Improvement*, ed. Heyne, 1987). Examples of genes for other traits include: Leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), Powdery Mildew resistance genes (Pm21), common bunt resistance genes (Bt-10), and wheat streak mosaic virus resistance gene (Wsm1), Russian wheat aphid resistance genes (Dn series such as Dn1, Dn2, Dn4, Dn5), Black stem rust resistance genes (Sr38), Yellow rust resistance genes (Yr series such as Yr1, YrSD, Yrsu, Yr17, Yr15, YrH52), Aluminum tolerance genes (Alt(BH)), dwarf genes (Rht), vernalization genes (Vm), Hessian fly resistance genes (H9, H10, H21, H29), grain color genes (R/r), glyphosate resistance genes (EPSPS), glufosinate genes (bar, pat) and water stress tolerance genes (Hva1, mtID). The trait of interest is transferred from the donor parent to the recurrent parent, in this case, the wheat plant disclosed herein. Single gene traits may result from either the transfer of a dominant allele or a recessive allele. Selection of progeny containing the trait of interest is done by direct selection for a trait associated with a dominant allele. Selection of progeny for a trait that is transferred via a recessive allele requires growing and 'selfing' the first backcross to determine which plants carry the recessive alleles. Recessive traits may require additional progeny testing in successive backcross generations to determine the presence of the gene of interest.

A further embodiment comprises or is a method of developing a backcross conversion 'RRR Scarlet' ('Rz1') plant that involves the repeated backcrossing to wheat variety 'RRR Scarlet' ('Rz1'). The number of backcrosses made may be 2, 3, 4, 5, 6 or greater, and the specific number of backcrosses used will depend upon the genetics of the donor parent and whether molecular markers are utilized in the backcrossing program. See, for example, R. E. Allan, "Wheat" in *Principles of Cultivar Development*, Fehr, W. R. Ed. (Macmillan Publishing Company, New York, 1987) pages 722-723, incorporated herein by reference. Using backcrossing methods, one of ordinary skill in the art can develop individual plants and populations of plants that retain at least 70%, 75%, 79%, 80%, 81%, 82%, 83%, 84%, 85%, 86%, 87%, 88%, 89%, 90% 91%, 92%, 93%, 94%, 95%, 96%, 97%, 98%, or 99% of the genetic profile of variety RRR Scarlet. The percentage of the genetics retained in the backcross conversion may be measured by either pedigree analysis or through the use of genetic techniques such as molecular markers or electrophoresis. In pedigree analysis, on average 50% of the starting germplasm would be passed to the progeny line after one cross to another line, 75% after backcrossing once, 87.5% after backcrossing twice, and so on. Molecular markers could also be used to confirm and/or determine the recurrent parent used. The backcross conversion developed from this method may be similar to variety 'RRR Scarlet' ('Rz1') for the results listed in TABLE 1. Such similarity may be measured by a side by side phenotypic comparison, with differences and similarities determined at a 5% significance level. Any such comparison should be made in environmental conditions that account for the trait being transferred. For example, herbicide should not be applied in the phenotypic comparison of herbicide resistant backcross conversion of 'RRR Scarlet' ('Rz1') to variety 'RRR Scarlet' ('Rz1').

Essentially Derived Varieties

Another embodiment of the invention is an essentially derived variety of genotype 'RRR Scarlet' ('Rz1'). As determined by the UPOV Convention, essentially derived varieties may be obtained for example by the selection of a natural or induced mutant, or of a somaclonal variant, the selection of a variant individual from plants of the initial variety, backcrossing, or transformation by genetic engineering. An essentially derived variety of genotype 'RRR Scarlet' ('Rz1') is further defined as one whose production requires the repeated use of genotype 'RRR Scarlet' ('Rz1') or is predominately derived from genotype of variety 'RRR Scarlet' ('Rz1'). International Convention for the Protection of New Varieties of Plants, as amended on Mar. 19, 1991, Chapter V, Article 14, Section 5(c).

Plant Breeding

Additional aspects comprise methods for using wheat variety 'RRR Scarlet' ('Rz1') in plant breeding. One such embodiment is the method of crossing wheat variety 'RRR Scarlet' ('Rz1') with another variety of wheat to form a first generation population of F1 plants. The population of first generation F1 plants produced by this method is also an embodiment of the invention. This first generation population of F1 plants will comprise an essentially complete set of the alleles of wheat variety 'RRR Scarlet' ('Rz1'). One of ordinary skill in the art can utilize either breeder books or molecular methods to identify a particular F1 plant produced using wheat variety 'RRR Scarlet' ('Rz1'), and any such individual plant is also encompassed by this invention. These embodiments also cover use of transgenic or backcross conversions of wheat variety 'RRR Scarlet' ('Rz1') to produce first generation F1 plants.

Yet additional aspects comprise a method of developing a 'RRR Scarlet' ('Rz1')-progeny wheat plant comprising crossing variety 'RRR Scarlet' ('Rz1') with a second wheat plant and performing a breeding method is also an embodiment of the invention. A specific method for producing a line derived from wheat variety 'RRR Scarlet' ('Rz1') is as follows. One of ordinary skill in the art would cross wheat variety 'RRR Scarlet' ('Rz1') with another variety of wheat, such as an elite variety. The F1 seed derived from this cross would be grown to form a homogeneous population. The F1 seed would contain one set of the alleles from variety 'RRR Scarlet' ('Rz1') and one set of the alleles from the other wheat variety. The F1 genome would be made-up of 50% variety RRR Scarlet and 50% of the other elite variety. The F1 seed would be grown and allowed to self, thereby forming F2 seed. On average the F2 seed would have derived 50% of its alleles from the genotype of 'RRR Scarlet' ('Rz1') and 50% from the other wheat variety, but various individual plants from the population would have a much greater percentage of their alleles derived variety 'RRR Scarlet' ('Rz1') (Wang J. and R. Bernardo, 2000, Crop Sci. 40:659-665 and Bernardo, R. and A. L. Kahler, 2001, Theor. Appl. Genet 102:986-992). The F2 seed would be grown and selection of plants would be made based on visual observation and/or measurement of traits. The 'RRR Scarlet' ('Rz1')-derived progeny that exhibit one or more of the desired 'RRR Scarlet' ('Rz1')-derived traits would be selected and each plant would be harvested separately. This F3 seed from each plant would be grown in individual rows and allowed to self. Then selected rows or plants from the rows would be harvested and threshed individually. The selections would again be based on visual observation and/or measurements for desirable traits of the plants, such as one or more of the desirable 'RRR Scarlet' ('Rz1')-derived traits. The process of growing and selection would be repeated any number of times until a homozygous 'RRR Scarlet' ('Rz1')-derived wheat plant is obtained. The homozygous 'RRR Scarlet' ('Rz1')-derived wheat plant would contain desirable traits derived from wheat genotype 'RRR Scarlet' ('Rz1'), some of which may not have been expressed by the other original wheat variety to which wheat genotype 'RRR Scarlet' ('Rz1') was crossed and some of which may have been expressed by both wheat varieties but now would be at a level equal to or greater than the level expressed in wheat genotype RRR Scarlet. The homozygous 'RRR Scarlet' ('Rz1')-derived wheat plants would have, on average, 50% of their genes derived from wheat variety genotype 'RRR Scarlet' ('Rz1'), but various individual plants from the population would have a much greater percentage of their alleles derived from genotype of 'RRR Scarlet' ('Rz1'). The breeding process, of crossing, selfing, and selection may be repeated to produce another population of 'RRR Scarlet' ('Rz1')-derived wheat plants with, on average, 25% of their genes derived from wheat 'RRR Scarlet' ('Rz1'), but various individual plants from the population would have a much greater percentage of their alleles derived from genotype 'RRR Scarlet' ('Rz1'). Another embodiment comprises or is a homozygous RRR Scarlet-derived wheat plant that has received RRR Scarlet-derived traits.

The previous example can be modified in numerous ways, for instance selection may or may not occur at every selfing generation, selection may occur before or after the actual self-pollination process occurs, or individual selections may be made by harvesting individual spikes, plants, rows or plots at any point during the breeding process described. In addition, double haploid breeding methods may be used at any step in the process. The population of plants produced at each and any generation of selfing is also an embodiment of the invention, and each such population variety 'RRR Scarlet' ('Rz1'), 25% of its genes from wheat variety 'RRR Scarlet' ('Rz1') in the second cycle of crossing, selfing, and selection, 12.5% of its genes from wheat variety 'RRR Scarlet' ('Rz1') in the third cycle of crossing, selfing, and selection, and so on.

Another embodiment of this invention is the method of crossing plants of the genotype 'RRR Scarlet' ('Rz1') with another variety of wheat and applying double haploid methods to the F1 seed or F1 plant or to any generation of 'RRR Scarlet' ('Rz1') -derived wheat obtained by the selfing of this cross.

Further aspects are directed to methods for producing 'RRR Scarlet' ('Rz1')-derived wheat plants by crossing wheat variety 'RRR Scarlet' ('Rz1') with a wheat plant and growing the progeny seed, and repeating the crossing or selfing along with the growing steps with the 'RRR Scarlet' ('Rz1')-derived wheat plant from 1 to 2 times, 1 to 3 times, 1 to 4 times, or 1 to 5 times. Thus, any and all methods using wheat variety 'RRR Scarlet' ('Rz1') in breeding are part of this invention, including selfing, pedigree breeding, backcrossing, hybrid production and crosses to populations. Unique starch profiles, molecular marker profiles and/or breeding records can be used by those of ordinary skill in the art to identify the progeny lines or populations derived from these breeding methods.

In addition, this invention also encompasses progeny with the same or greater yield of 'RRR Scarlet' ('Rz1'), the same or greater drought tolerance of 'RRR Scarlet' ('Rz1'), and the same or greater resistance to lodging as 'RRR Scarlet' ('Rz1'). The expression of these traits may be measured by a side by side phenotypic comparison, with differences and similarities determined at a 5% significance level. Any such comparison should be made in the same environmental conditions.

General Breeding and Selection Methods

Overview. Plant breeding is the genetic manipulation of plants. The goal of wheat breeding is to develop new, unique and superior wheat varieties. In practical application of a wheat breeding program, and as discussed in more detail herein below, the breeder initially selects and crosses two or more parental lines, followed by repeated 'selfing' and selection, producing many new genetic combinations. The breeder can theoretically generate billions of different genetic combinations via crossing, 'selfing' and naturally induced mutations. The breeder has no direct control at the cellular level, and two breeders will never, therefore, develop exactly the same line. Each year, the plant breeder selects the germplasm to advance to the next generation. This germplasm may be grown under unique and different geographical, climatic and soil conditions, and further selections may be made during and at the end of the growing season.

Proper testing can detect major faults and establish the level of superiority or improvement over current varieties. In addition to showing superior performance, it is desirable that this a demand for a new variety. The new variety should optimally be compatible with industry standards, or create a new market. The introduction of a new variety may incur additional costs to the seed producer, the grower, processor and consumer, for special advertising and marketing, altered seed and commercial production practices, and new product utilization. The testing preceding release of a new variety should take into consideration research and development costs as well as technical superiority of the final variety. Ideally, it should also be feasible to produce seed easily and economically.

These processes, which lead to the final step of marketing and distribution, can take from six to twelve years from the time the first cross is made. Therefore, development of new varieties is a time-consuming process that requires precise forward planning, efficient use of resources, and a focused direction. Various breeding and selection methods are known in the art, and have substantial utility in the context of particular aspects of the present invention.

Goals of Breeding. Wheat (*Triticum aestivum* L.), is an important and valuable field crop, and a continuing goal of wheat breeders is to develop stable, high yielding wheat varieties that are agronomically sound and have good milling and baking qualities for its intended use. A wheat breeder must therefore select and develop wheat plants that have the traits that result in superior varieties. There are numerous steps in the development of any novel and desirable plant germplasm. Plant breeding begins with the analysis and definition of problems and weaknesses of the current germplasm, the establishment of program goals, and the definition of specific breeding objectives. This assessment is followed by selection of germplasm that possess the traits to meet the program goals; that is, to combine in a single variety an improved combination of desirable traits from the parental germplasm. These important traits may include, but are not limited to higher seed yield, resistance to diseases and insects, tolerance to drought and heat, improved grain quality, better agronomic qualities, herbicide resistance, etc.

Breeding methods reflect pollination mode. Field crops are bred through techniques that take advantage of the plant's method of pollination. A plant is self-pollinated if pollen from one flower is transferred to the same or another flower of the same plant. A plant is sib-pollinated when individuals within the same family or line are used for pollination. A plant is cross-pollinated if the pollen comes from a flower on a different plant from a different family or line. The term cross-pollination herein does not include self-pollination or sib-pollination. Wheat plants (*Triticum aestivum* L.), are recognized to be naturally self-pollinated plants which, while capable of undergoing cross-pollination, rarely do so in nature. Thus, in the case of wheat, intervention for control of pollination is critical to the establishment of superior varieties. A cross between two different homozygous lines produces a uniform population of hybrid plants that may be heterozygous for many gene loci. A cross of two heterozygous plants each that differ at a number of gene loci will produce a population of plants that differ genetically and will not be uniform. Regardless of parentage, plants that have been self-pollinated and selected for type for many generations become homozygous at almost all gene loci and produce a uniform population of true breeding progeny.

The term 'homozygous plant' is hereby defined as a plant with homozygous genes at 95% or more of its loci.

The term "inbred" as used herein refers to a homozygous plant or a collection of homozygous plants.

Choice of breeding or selection methods. Choice of breeding or selection methods depends on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. The complexity of inheritance also influences choice of the breeding method. Breeding generally starts with cross-hybridizing two genotypes (a "breeding cross"), each of which may have one or more desirable characteristics that is lacking in the other or which complements the other. If the two original parents do not provide all the desired characteristics, other sources can be included by making more crosses. In each successive filial generation (e.g., F1→F2; F2→F3; F3 →F4; F4→F5, etc.), plants are 'selfed' to increase the homozygosity of the line. Typically in a breeding program five or more generations of selection and 'selfing' are practiced to obtain a homozygous plant. Each wheat breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Promising advanced breeding lines are thoroughly tested and compared to appropriate standards in environments representative of the commercial target area(s), or Areas of Adaptability; that is, the location with the environmental conditions that would be well suited for this wheat variety. Area of adaptability is based on a number of factors, for example: days to heading, winter hardiness, insect resistance, disease resistance, and drought resistance. Area of adaptability does not indicate that the wheat variety will grow in every location within the area of adaptability or that it will not grow outside the area. Exemplary areas of adaptability are: Northern area=States of DE, IL, IN, MI, MO, NJ, NY, OH, PA, WI and Ontario, Canada; Mid-south=States of AR, KY, MO and TN; Southeast=States of NC, SC, and VA; Deep South=States of AL, GA, LA, and MS. The best lines are candidates for new commercial varieties; those still deficient in a few traits may be used as parents to produce new populations for further selection.

Identification of individuals that are genetically superior is a difficult task because for most traits the true genotypic value is masked by other confounding plant traits or environmental factors. One method of identifying a superior genotype is to observe its performance relative to other experimental genotypes and to a widely grown standard variety. Generally, a single observation is inconclusive, so replicated observations are required to provide a better estimate of its genetic worth. A breeder uses various methods to help determine which plants should be selected from the segregating populations and ultimately which lines will be used for commercialization. In addition to the knowledge of the germplasm and other skills used by a breeder, a part of the selection process is dependent on experimental design coupled with the use of statistical analysis. Experimental design and statistical analysis are used to help determine which plants, which family of plants, and finally which lines are significantly better or different for one or more traits of interest. Experimental design methods are used to control error so that differences between two lines can be more accurately determined. Statistical analysis includes the calculation of mean values, determination of the statistical significance of the sources of variation, and the calculation of the appropriate variance components. Five and one percent significance levels are customarily used to determine whether a difference that occurs for a given trait is real or due to the environment or experimental error.

Selection methods. Popular selection methods commonly include pedigree selection, modified pedigree selection, mass selection, recurrent selection, etc. Descriptions of other breeding methods that are commonly used for different traits and crops can be found in one of several reference books (e.g., Allard, *Principles of Plant Breeding*, 1960; Simmonds, *Principles of Crop Improvement*, 1979; editor Heyne, *Wheat and Wheat Improvement*, 1987; Allan, "Wheat", Chapter 18, *Principles of Crop Development*, vol. 2, Fehr editor, 1987).

Pedigree breeding. Pedigree breeding is commonly used for the improvement of self-pollinating crops (e.g., wheat, etc). Two parents that possess favorable, complementary traits are crossed to produce an F1. An F2 population is produced by 'selfing' or 'sibbing' one or several F1's. Selection of the best individuals may begin in the F2 population, and beginning in the F3, the best individuals in the best families are selected. Replicated testing of families can begin in the F4 generation to improve the effectiveness of selection for traits with low heritability. At an advanced stage of inbreeding (e.g., F5, F6 and F7), the best lines or mixtures of phenotypically similar lines are tested for potential release as new varieties.

Backcross breeding. Backcross breeding may be used to transfer genes for simply inherited, qualitative, traits from a donor parent into a desirable homozygous variety that is utilized as the recurrent parent. The source of the traits to be transferred is called the donor parent. After the initial cross, individuals possessing the desired trait or traits of the donor parent are selected and then repeatedly crossed (backcrossed) to the recurrent parent. The resulting plant is expected to have the attributes of the recurrent parent (e.g., variety) plus the desirable trait or traits transferred from the donor parent. This approach has been used extensively for breeding disease-resistant varieties.

Recurrent selection. Various recurrent selection techniques are used to improve quantitatively inherited traits controlled by numerous genes. The use of recurrent selection in self-pollinating crops depends on the ease of pollination and the number of hybrid offspring recovered from each successful cross. Recurrent selection can be used to improve populations of either self- or cross-pollinated crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. Plants from the populations can be selected and self-pollinated to create new varieties.

Single-seed descent and modified single-seed descent. Another breeding method is single-seed descent. This procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed. In a multiple-seed procedure, wheat breeders commonly harvest one or more spikes (heads) from each plant in a population and thresh them together to form a 'bulk.' Part of the 'bulk' is used to plant the next generation and part is put in reserve. The procedure has been referred to as modified single-seed descent. The multiple-seed procedure has been used to save labor at harvest. It is considerably faster to thresh spikes with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Bulk breeding. Bulk breeding can also be used. In the bulk breeding method, an F2 population is grown. The seed from the populations is harvested in bulk and a sample of the seed is used to make a planting the next season. This cycle can be repeated several times. In general, when individual plants are expected to have a high degree of homozygosity, individual plants are selected, tested, and increased for possible use as a variety.

Determination of homozygotic stability, phenotypic stability, heritability and identity, and the use of 'Marker Assisted Selection' (MAS).' There are many analytical methods available to determine the homozygotic stability, phenotypic stability, heritability and identity of the wheat varieties. The oldest and most traditional method of analysis is the observation of phenotypic traits. The data is usually collected in field experiments over the life of the wheat plants to be examined. Phenotypic characteristics most often observed are for traits such as seed yield, head configuration, glume configuration, seed configuration, lodging resistance, disease resistance, maturity, etc.

In addition to phenotypic observations, the genotype of a plant can also be examined through segregation analysis or the use of biotechnology. There are many art-recognized, laboratory-based techniques available for the analysis, comparison and characterization of plant genotype, including but not limited to Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs). One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of 'markers' linked to the positive-effecting alleles and/or the elimination of the markers linked to the negative-effecting alleles from the plant's genome.

Molecular markers can also be used during the breeding process for the selection of qualitative and quantitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program (Openshaw et al. Marker-assisted Selection in Backcross Breeding. In: Proceedings Symposium of the Analysis of Molecular Marker Data, 5-6 Aug. 1994, pp. 41-43. Crop Science Society of America, Corvallis, Oreg.). The use of molecular markers in the selection process is often called 'Genetic Marker Enhanced Selection' or 'Marker Assisted Selection' (MAS).

Use of 'double haploids' (DH). The production of 'double haploids' can also be used for the development of homozygous lines in a breeding program. Double haploids are produced by the doubling of a set of chromosomes (1N) from a heterozygous plant to produce a completely homozygous individual. This can be advantageous because the process omits the generations of 'selfing' otherwise needed to obtain a homozygous plant from a heterozygous source. Various methodologies of making double haploid plants in wheat are known in the art (e.g., Laurie, D. A. and S. Reymondie, Plant Breeding, 1991, v. 106:182-189; Singh, N. et al., Cereal Research Communications, 2001, v. 29:289-296; Redha, A. et al., Plant Cell Tissue and Organ Culture, 2000, v. 63:167-172; and U.S. Pat. No. 6,362,393).

Use of 'hybrid' wheat. Though pure-line varieties are the predominate form of wheat grown for commercial wheat production hybrid wheat is also used. Hybrid wheat plants are produced with the help of cytoplasmic male sterility, nuclear genetic male sterility, or chemicals. Various combinations of these three male sterility systems have been used in the production of hybrid wheat.

Tissue culture and regeneration. Further reproduction of the root-rot-tolerant wheat genotypes of the invention can occur by tissue culture and regeneration. Tissue culture of various tissues of wheat and regeneration of plants therefrom is well known and widely published. A review of various wheat tissue culture protocols can be found in "In Vitro Culture of Wheat and Genetic Transformation-Retrospect and Prospect" by Maheshwari et al. (*Critical Reviews in Plant Sciences*, 14(2): pp 149-178, 1995). Thus, another inventive aspect is to provide cells that upon growth and differentiation produce wheat plants capable of having the physiological and morphological characteristics of the root-rot-tolerant wheat genotypes of the invention.

Mutation Breeding

Mutation Breeding has been used successfully to develop wheat varieties with resistance to powdery mildew (J. T. Kinane and P. W. Jones 2001. "Isolation of wheat mutants with increased resistance to powdery mildew from small induced variant populations." Euphytica 117 (3): 251-260), leaf rust and stem rust (N. D. Williams, J. D. Miller, and D. L. Klindworth 1992. "Induced mutations of a genetic suppressor of resistance to wheat stem rust." Crop Science 32(3): 612-617; B. Friebe, J. Jiang, D. R. Knott, and B. S. Gill 1994. "Compensation indices of radiation-induced wheat-*Agropyron elongatum* translocations conferring resistance to leaf rust and stem rust." Crop Science 34 (2): 400-404; E. R. Kerber and T. Aung 1995. "Confirmation of nonsuppressor mutation of stem rust resistance in 'Canthatch' common wheat." Crop Science 35(3): 743-744); and yellow and brown rust.

Isolated Root-Rot-Tolerance Gene Sequences and Their Use

Also, contemplated by the instant invention are the nucleic acids which comprise the genes which when expressed in the wheat plant, provide root-rot resistance in wheat plants. The genetic sequences that comprise mutations responsible for conferring root-rot tolerance to the wheat plants of the present invention can be genetically mapped, identified, isolated, and the sequence determined by those of ordinary skill in the art (see e.g., Example 6 herein). See also, for example: Plant Genomes: Methods for Genetic and Physical Mapping, J. S. Beckmann and T. C. Osborn, 1992, Kluwer Academic Publishers; Genome Mapping in Plants, Paterson, 1996, Harcourt Brace and Co.; Wheat Genome Mapping, A. Kalinski, 1996, Diane Publishing Co.; and Methods in Molecular Biology, Vol. 82, *Arabidopsis* Protocols, Martinez Zapater and Salinas, 1998, Humana Press. Where the isolated nucleic acid encoding the genetic element conferring the root-rot resistance encodes a protein responsible for causing the plant to be root-rot resistant, the isolated nucleic acid can be used to (1) identify other nucleic acids which may contain mutations that provide root-rot resistance to wheat plants; (2) introduce the isolated nucleic acid into a wheat plant which lacks root-rot resistance by means of genetic engineering; (3) insert the isolated nucleic acid into a suitable vector which can be expressed in a wheat plant; and (4) insert the vector into a plant cell (e.g., a wheat plant cell).

The present invention also contemplates the fabrication of DNA constructs comprising the isolated nucleic acid sequence containing the genetic element and/or coding sequence from the gene that confers root-rot resistance operatively linked to plant gene expression control sequences. "DNA constructs" are defined herein to be constructed (not naturally-occurring) DNA molecules useful for introducing DNA into host cells, and the term includes chimeric genes, expression cassettes, and vectors.

As used herein "operatively linked" refers to the linking of DNA sequences (including the order of the sequences, the orientation of the sequences, and the relative spacing of the various sequences) in such a manner that the encoded protein is expressed. Methods of operatively linking expression control sequences to coding sequences are well known in the art. See, e.g., Maniatis et al., Molecular Cloning: A Laboratory Manual, Cold Spring Harbor, N.Y., 1982; and Sambrook et al., Molecular Cloning: A Laboratory Manual, Cold Spring Harbor, N.Y., 1989.

"Expression control sequences" are DNA sequences involved in any way in the control of transcription or translation. Suitable expression control sequences and methods of making and using them are well known in the art.

The expression control sequences preferably include a promoter. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds, Nucleic Acids Res., 15, 2343-2361, 1987. Also, the location of the promoter relative to the transcription start may be optimized. See, e.g., Roberts et al., Proc. Natl. Acad. Sci. USA, 76:760-764, 1979.

Many suitable promoters for use in plants are well known in the art. For instance, suitable constitutive promoters for use in plants include the promoters of plant viruses, such as the peanut chlorotic streak caulimovirus (PC1SV) promoter (U.S. Pat. No. 5,850,019); the 35S and 19S promoter from cauliflower mosaic virus (CaMV) (Odell et al., I 313:3810-812, 1985); promoters of the *Chlorella* virus methyltransferase genes (U.S. Pat. No. 5,563,328); the full-length transcript promoter from figwort mosaic virus (FMV) (U.S. Pat. No. 5,378,619); the promoters from such genes as rice actin (McElroy et al., Plant Cell 2:163-171(1990)), ubiquitin (Christiansen et al., Plant Mol. Biol. 12:619-632, 1989), and (Christiansen et al., Plant Mol. Biol. 18: 675-689, 1992), pEMU (Last et al., Theor. Appl. Genet. 81:581-588, 1991), MAS (Velten et al., Embo J. 3:2723-2730, 1984), wheat histone (Lepetit et al., Mol. Gen. Genet. 231:276-285, 1992), and Atanassova et al., Plant Journal 2:291-300, 1992), *Brassica napus* ALS3 (International Publication No. WO 97/41228); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al., Proc. Natl. Acad. Sci. 90:4567-4571, 1993); the promoter of the wheat In 2 gene which responds to benzenesulfonomide herbicide safeners (U.S. Pat. No. 5,364,780 and Gatz et al., Mol. Gen. Genet. 243:32-38, 1994), and the promoter of the Tet repressor from Tn10 (Gatz et al., Mol. Gen. Genet. 227:229-237, 1991). According to one embodiment, the promoter for use in plants is one that responds to an inducing agent to which plants normally do not respond. An exemplary inducible promoter of this type is the inducible promoter from a steroid hormone gene, the transcriptional activity of which is induced by a glucosteroid hormone (Schena et al., Proc. Natl. Acad. Sci. 88:10421, 1991) or the application of a chimeric transcription activator, XVE, for use in an estrogen receptor-based inducible plant expression system activated by estradiol (Zou et al., Plant J. 24 265-273, 2000). Other inducible promoters for use in plants are described in European Patent No. 332104, International Publication No. WO 93/21334 and International Publication No. WO 97/06269, and discussed in Gatz and Lenk Trends Plant Sci., 3:352-358, 1998, and Zou and Chua, Curr. Opin. Biotechnol., 11:146-151, 2000. Finally, promoters composed of portions of other promoters and partially or totally synthetic promoters can be used. See, e.g., Ni et al., Plant J. 7:661-676, 1995, and International Publication No. WO 95/14098, which describes such promoters for use in plants.

The promoter may include, or be modified to include, one or more enhancer elements. Preferably, the promoter will include a plurality of enhancer elements. Promoters containing enhancer elements provide for higher levels of transcription as compared to promoters that do not include them. Suitable enhancer elements for use in plants include the PC1SV enhancer element (U.S. Pat. No. 5,850,019), the CaMV 35S enhancer element (U.S. Pat. Nos. 5,106,739 and 5,164,316), and the FMV enhancer element (Maiti et al., Transgenic Res., 6:143-156, 1997). See also, International Publication No. WO 96/23898 and Enhancers and Eukaryotic Expression (Cold Spring Harbor Press, Cold Spring Harbor, N.Y., 1983).

For efficient expression, the coding sequences are preferably also operatively linked to a 3' untranslated sequence. The 3' untranslated sequence will preferably include a transcription termination sequence and a polyadenylation sequence. The 3' untranslated region can be obtained from the flanking regions of genes from *Agrobacterium*, plant viruses, plants and other eukaryotes. Suitable 3' untranslated sequences for use in plants include those of the cauliflower mosaic virus 35S gene, the phaseolin seed storage protein gene, the pea ribulose-1,5-bisphosphate carboxylase small subunit E9 gene, the wheat 7S storage protein gene, the octopine synthase gene, and the nopaline synthase gene.

A 5' untranslated leader sequence can also be optionally employed. The 5' untranslated leader sequence is the portion of an mRNA that extends from the 5' CAP site to the translation initiation codon. This region of the mRNA is necessary for translation initiation in plants and plays a role in the regulation of gene expression. Suitable 5' untranslated leader sequence for use in plants includes those of alfalfa mosaic virus, cucumber mosaic virus coat protein gene, and tobacco mosaic virus.

The DNA construct may be a 'vector.' The vector may contain one or more replication systems which allow it to replicate in host cells. Self-replicating vectors include plasmids, cosmids and virus vectors. Alternatively, the vector may be an integrating vector which allows the integration into the host cell's chromosome of the DNA sequence encoding the root-rot resistance gene product. The vector desirably also has unique restriction sites for the insertion of DNA sequences. If a vector does not have unique restriction sites it may be modified to introduce or eliminate restriction sites to make it more suitable for further manipulation.

Vectors suitable for use in expressing the nucleic acids, which when expressed in a plant confer root-rot resistance, include but are not limited to pMON979, pMON977, pMON886, pCaMVCN, and vectors derived from the tumor inducing (Ti) plasmid of *Agrobacterium tumefaciens* described by Rogers et al., Meth. Enzymol., 153:253-277, 1987. The nucleic acid is inserted into the vector such that it is operably linked to a suitable plant active promoter. Suitable plant active promoters for use with the nucleic acids include, but are not limited to CaMV35S, ACTJN, FMV35S, NOS and PCSLV promoters. The vectors comprising the nucleic acid can be inserted into a plant cell using a variety of known methods. For example, DNA transformation of plant cells include but are not limited to *Agrobacterium*-mediated plant transformation, protoplast transformation, electroporation, gene transfer into pollen, injection into reproductive organs, injection into immature embryos and particle bombardment. These methods are described more fully in U.S. Pat. No. 5,756,290, and in a particularly efficient protocol for wheat described in U.S. Pat. No. 6,153,812, and the references cited therein. Site-specific recombination systems can also be employed to reduce the copy number and random integration of the nucleic acid into the cotton plant genome. For example, the Cre/lox system can be used to immediate lox site-specific recombination in plant cells. This method can be found at least in Choi et al., Nuc. Acids Res. 28:B19, 2000).

Transgenes:

Molecular biological techniques allow the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, that are inserted into the genome using transformation are referred to herein collectively as "transgenes." Several methods for producing transgenic plants have been developed, and the present invention, in particular embodiments, also relates to transformed versions of the root-rot-tolerant wheat genotypes of the invention.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements. Various genetic elements can be introduced into the plant genome using transformation. These elements include but are not limited to genes; coding sequences; inducible, constitutive, and tissue specific promoters; enhancing sequences; and signal and targeting sequences.

A genetic trait which has been engineered into a particular wheat plant using transformation techniques could be moved into another line using traditional breeding techniques that are well known in the plant breeding arts. For example, a backcrossing approach could be used to move a transgene from a transformed wheat plant to an elite wheat variety and the resulting progeny would comprise a transgene. As used herein, "crossing" can refer to a simple X by Y cross, or the process of backcrossing, depending on the context. The term "breeding cross" excludes the processes of selfing or sibbing.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-96, 1981.

According to a preferred embodiment, the transgenic plant provided for commercial production of foreign protein is a wheat plant. In another preferred embodiment, the biomass of interest is seed. A genetic map can be generated, primarily via conventional RFLP, PCR, and SSR analysis, which identifies the approximate chromosomal location of the integrated DNA molecule. For exemplary methodologies in this regard, see Glick and Thompson, Methods in Plant Molecular Biology and Biotechnology 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Introduction of Transgenes of Agronomic Interest by Transformation

Agronomic genes can be expressed in transformed plants. For example, plants can be genetically engineered to express various phenotypes of agronomic interest, or, alternatively, transgenes can be introduced into a plant by breeding with a plant that has the transgene. Through the transformation of wheat, the expression of genes can be modulated to enhance disease resistance, insect resistance, herbicide resistance, water stress tolerance and agronomic traits as well as grain quality traits. Transformation can also be used to insert DNA sequences which control or help control male-sterility. DNA sequences native to wheat as well as non-native DNA sequences can be transformed into wheat and used to modulate levels of native or non-native proteins. Anti-sense technology, various promoters, targeting sequences, enhancing sequences, and other DNA sequences can be inserted into the wheat genome for the purpose of modulating the expression of proteins. Exemplary genes implicated in this regard include, but are not limited to, those categorized below.

1. Genes that Confer Resistance to Pests or Disease:

(A) Plant defenses are often activated by specific interaction between the product of a disease resistance gene (R) in the plant and the product of a corresponding avirulence (Avr) gene in the pathogen. A plant variety can be transformed with a cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78:1089, 1994 (*Arabidopsis* RSP2 gene for resistance to *Pseudomonas syringae*).

*Fusarium* head blight along with deoxynivalenol both produced by the pathogen *Fusarium graminearum* Schwabe have caused devastating losses in wheat production. Genes expressing proteins with antifungal action can be used as transgenes to prevent *Fusarium* head blight. Various classes of proteins have been identified. Examples include endochitinases, exochitinases, glucanases, thionins, thaumatin-like proteins, osmotins, ribosome inactivating proteins, flavonioids, lactoferricin. During infection with *Fusarium graminearum* deoxynivalenol is produced. There is evidence that production of deoxynivalenol increases the virulence of the disease. Genes with properties for detoxification of deoxynivalenol (Adam and Lemmens, In International Congress on Molecular Plant-Microbe Interactions, 1996; McCormick et al. Appl. Environ. Micro. 65:5252-5256, 1999) have been engineered for use in wheat. A synthetic peptide that competes with deoxynivalenol has been identified (Yuan et al., Appl. Environ. Micro. 65:3279-3286, 1999). Changing the ribosomes of the host so that they have reduced affinity for deoxynivalenol has also been used to reduce the virulence of the *Fusarium graminearum*.

Genes used to help reduce *Fusarium* head blight include but are not limited to Tri101 (*Fusarium*), PDR5 (yeast), tip-1 (oat), tip-2 (oat), leaf tip-1 (wheat), tip (rice), tip-4 (oat), endochitinase, exochitinase, glucanase (*Fusarium*), permatin (oat), seed hordothionin (barley), alpha-thionin (wheat), acid glucanase (alfalfa), chitinase (barley and rice), class beta II-1,3-glucanase (barley), PR5/tip (*arabidopsis*), zeamatin (maize), type 1 RIP (barley), NPR1 (*arabidopsis*), lactoferrin (mammal), oxalyl-CoA-decarboxylase (bacterium), IAP (baculovirus), ced-9 (*C. elegans*), and glucanase (rice and barley).

(B) A gene conferring resistance to a pest, such as Hessian fly, wheat, stem soft fly, cereal leaf beetle, and/or green bug, for example, the H9, H10, and H21 genes.

(C) A gene conferring resistance to disease, including wheat rusts, *septoria tritici, septoria nodorum*, powdery mildew, helminthosporium diseases, smuts, bunts, *fusarium* diseases, bacterial diseases, and viral diseases.

(D) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt delta-endotoxin gene. Moreover, DNA molecules encoding delta-endotoxin genes can be purchased from American Type Culture Collection (Manassas, Va.), for example, under ATCC Accession Nos. 40098, 67136, 31995 and 31998.

(E) An insect-specific hormone or pheromone such as an ecdysteroid and juvenile hormone, a variant thereof, a mimetic based thereon, or an antagonist or agonist thereof. See, for example, the disclosure by Hammock et al., Nature 344:458, 1990, of baculovirus expression of cloned juvenile hormone esterase, an inactivator of juvenile hormone.

(F) An insect-specific peptide or neuropeptide which, upon expression, disrupts the physiology of the affected pest. For example, see the disclosures of Regan, *J. Biol Chem*. 269:9, 1994 (expression cloning yields DNA coding for insect diuretic hormone receptor), and Pratt et al., Biochem. Biophys. Res. Comm.163:1243, 1989 (an allostatin is identified in *Diploptera puntata*). See also U.S. Pat. No. 5,266,317 to Tomalski et al., who disclose genes encoding insect-specific, paralytic neurotoxins.

(G) An enzyme responsible for an hyperaccumulation of a monterpene, a sesquiterpene, a steroid, hydroxamic acid, a phenylpropanoid derivative or another non-protein molecule with insecticidal activity.

(H) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol*. 23: 691 (1993), who teach the nucleotide sequence of a cDNA encoding tobacco hookworm chitinase, and Kawalleck et al., Plant Molec. Biol 21:673, 1993, providing the nucleotide sequence of the parsley ubi4-2 polyubiquitin gene.

(I) A molecule that stimulates signal transduction. For example, see the disclosure by Botella et al., Plant Molec. Biol. 24:757, 1994, of nucleotide sequences for mung bean calmodulin cDNA clones, and Griess et al., Plant Physiol. 104:1467, 1994, who provide the nucleotide sequence of a maize calmodulin cDNA clone.

(J) A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference for this purpose.

(K) A membrane permease, a channel former or a channel blocker. For example, see the disclosure by Jaynes et al., Plant Sci. 89:43, 1993, of heterologous expression of a cecropin-beta lytic peptide analog to render transgenic tobacco plants resistant to *Pseudomonas solanacearum*.

(L) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451, 1990. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(M) An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland, 1994 (enzymatic inactivation in transgenic tobacco via production of single-chain antibody fragments).

(N) A virus-specific antibody. See, for example, Tavladorali et al., Nature 366:469, 1993, who show that transgenic plants expressing recombinant antibody genes are protected from virus attack.

(O) A developmental-arrestive protein produced in nature by a pathogen or a parasite. Thus, fungal endo alpha-1,4-D-polygalacturonases facilitate fungal colonization and plant nutrient release by solubilizing plant cell wall homoalpha-1,4-D-galacturonase. See Lamb et al., Bio/Technology 10:1436, 1992. The cloning and characterization of a gene which encodes a bean endopolygalacturonase-inhibiting protein is described by Toubart et al., Plant J. 2:367, 1992.

(P) A developmental-arrestive protein produced in nature by a plant. For example, Logemann et al., Bio/Technology 10:305, 1992, have shown that transgenic plants expressing the barley ribosome-inactivating gene have an increased resistance to fungal disease.

(Q) Genes involved in the Systemic Acquired Resistance (SAR) Response and/or the pathogenesis related genes. Briggs, Current Biology, 5(2), 1995.

(R) Antifungal genes (Cornelissen and Melchers, Plant Physiol. 101:709-712, 1993; Parijs et al., Planta 183:258-264, 1991; and Bushnell et al., Can. J. of Plant Path. 20:137-149, 1998).

(S) Detoxification genes, such as for fumonisin, beauvericin, moniliformin and zearalenone and their structurally related derivatives. For example, see U.S. Pat. No. 5,792,931.

(T) Cystatin and cysteine proteinase inhibitors.

(U) Defensin genes. See WO03000863.

(V) Genes conferring resistance to nematodes. See WO 03/033651 and Urwin et. al., Planta 204:472-479, 1998.

2. Genes that Confer Resistance to an Herbicide:

(A) Acetohydroxy acid synthase, which has been found to make plants that express this enzyme resistant to multiple types of herbicides, has been introduced into a variety of plants (see, e.g., Hattori et al., Mol Gen Genet 246:419, 1995). Other genes that confer tolerance to herbicides include: a gene encoding a chimeric protein of rat cytochrome P4507A1 and yeast NADPH-cytochrome P450 oxidoreductase (Shiota et al., Plant Physiol. 106:17, 1994), genes for glutathione reductase and superoxide dismutase (Aono et al., Plant Cell Physiol 36:1687, 1995) and genes for various phosphotransferases (Datta et al., Plant Mol Biol. 20:619, 1992).

(B) A herbicide that inhibits the growing point or meristem, such as an imidazalinone or a sulfonylurea. Exemplary genes in this category code for mutant ALS and AHAS enzyme as described, for example, by Lee et al., EMBO J. 7: 1241, 1988, and Miki et al., Theor. Appl. Genet. 80: 449, 1990, respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference for this purpose.

(C) Glyphosate (tolerance, or resistance, imparted by mutant 5-enolpyruvl-3-phosphikimate synthase (EPSP) and aroA genes, respectively) and other phosphono compounds such as glufosinate (phosphinothricin acetyl transferase, PAT) and Streptomyces hygroscopicus phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. In U.S. Pat. No. 5,627,061 to Barry et al. describes genes encoding EPSPS enzymes. In U.S. 2002/0062503 A1 Chen et al. describe a wheat plant tolerant to glyphosate. The DNA construct pMON30139 was inserted in wheat via transformation and contains the EPSPS gene as well as other elements. See also U.S. Pat. Nos. 6,248,876 B1; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and U.S. Pat. No. 5,491,288; and international publications WO 97/04103; WO 00/66746; WO 01/66704; and WO 00/66747, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. Application Ser. Nos. 60/244,385; 60/377,175 and 60/377,719.

A DNA molecule encoding a mutant aroA gene can be obtained under ATCC accession No. 39256, and the nucleotide sequence of the mutant gene is disclosed in U.S. Pat. No. 4,769,061 to Comai. European Patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., Bio/Technology 7: 61, 1989, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose. Vasil et al. (Bio/Technology 10:667, 1992) reported developing wheat plants resistant to glufosinate via particle bombardment and the use of bar genes. The use of bar genes has also resulted in the resistance to the herbicide bialaphos. Exemplary of genes conferring resistance to phenoxy propionic acids and cycloshexones, such as sethoxydim and haloxyfop, are the Acc1-S1, Acc1-S2 and Acc1-S3 genes described by Marshall et al., Theor. Appl. Genet. 83:435, 1992.

(D) A herbicide that inhibits photosynthesis, such as a triazine (psbA and gs+ genes) and a benzonitrile (nitrilase gene). Przibilla et al., Plant Cell 3:169, 1991, describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., Biochem. J. 285:173, 1992.

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825, which are incorporated herein by reference for this purpose.

3. Genes that Confer or Improve Grain Quality:

(A) The content of high-molecular-weight gluten subunits (HMW-GS). Genomic clones have been isolated for different HMW subunits (Anderson et al., In Proceedings of the 7th International Wheat Genetics Symposium, IPR, pp. 699-704, 1988; Shewry et al. In Oxford Surveys of Plant Molecular and Cell Biology, pp. 163-219, 1989; Shewry et al. Journal of Cereal Sci. 15:105-120, 1992). Blechl et al. (J. Plant Phys. 152: 703-707, 1998) have transformed wheat with genes that encode a modified HMW-GS. See also U.S. Pat. Nos. 5,650,558; 5,914,450; 5,985,352; 6,174,725; and 6,252,134, which are incorporated herein by reference for this purpose.

(B) Modified fatty acid metabolism, for example, by transforming a plant with an antisense gene of stearoyl-ACP desaturase to increase stearic acid content of the plant. See Knultzon et al., Proc. Nat'l. Acad. Sci. USA 89:2624, 1992.

(C) Decreased phytate content for example introduction of a phytase-encoding gene would enhance breakdown of phytate, adding more free phosphate to the transformed plant. For example, see Van Hartingsveldt et al., *Gene* 127:87, 1993, for a disclosure of the nucleotide sequence of an *Aspergillus niger* phytase gene. See also U.S. patent application Ser. Nos. 10/255,817 and 10/042,894 and international publication numbers WO 99/05298, WO 03/027243, and WO 02/059324, which are incorporated herein by reference for this purpose.

(D) Modified carbohydrate composition effected, for example, by transforming plants with a gene coding for an enzyme that alters the branching pattern of starch. See Shiroza et al., *J. Bacteriol.* 170:810, 1988 (nucleotide sequence of *Streptococcus mutans* fructosyltransferase gene), Steinmetz et al., *Mol. Gen. Genet.* 200:220, 1985 (nucleotide sequence of *Bacillus subtilis* levansucrase gene), Pen et al., *Bio/Technology* 10:292, 1992 (production of transgenic plants that express *Bacillus licheniformis* alpha-amylase), Elliot et al., *Plant Molec. Biol.* 21:515, 1993 (nucleotide sequences of tomato invertase genes), Søgaard et al., J. Biol. Chem. 268:22480, 1993 (site-directed mutagenesis of barley alpha-amylase gene), and Fisher et al., *Plant Physiol.* 102:1045, 1993 (maize endosperm starch branching enzyme II).

4. Genes that Control Male Sterility:
(A) Introduction of a deacetylase gene under the control of a tapetum-specific promoter and with the application of the chemical N-Ac-PPT (WO 01/29237).
(B) Introduction of various stamen-specific promoters (WO 92/13956, WO 92/13957).
(C) Introduction of the barnase and the barstar gene (Paul et al., Plant Mol. Biol. 19:611-622, 1992).

5. Genes that Confer Agronomic Enhancements, Nutritional Enhancements, or Industrial Enhancements:
(A) Improved tolerance to water stress from drought or high salt water condition. The HVA1 protein belongs to the group 3 LEA proteins that include other members such as wheat pMA2005, cotton D-7, carrot Dc3, and rape pLEA76. These proteins are characterized by 11-mer tandem repeats of amino acid domains which may form a probable amphophilic alpha-helical structure that presents a hydrophilic surface with a hydrophobic stripe. The barley HVA1 gene and the wheat pMA2005 gene are highly similar at both the nucleotide level and predicted amino acid level. These two monocot genes are closely related to the cotton D-7 gene and carrot Dc3 gene with which they share a similar structural gene organization. There is, therefore, a correlation between LEA gene expression or LEA protein accumulation with stress tolerance in a number of plants. For example, in severely dehydrated wheat seedlings, the accumulation of high levels of group 3 LEA proteins was correlated with tissue dehydration tolerance (Ried and Walker-Simmons, 1993). Studies on several indica varieties of rice showed that the levels of group 2 LEA proteins (also known as dehydrins) and group 3 LEA proteins in roots were significantly higher in salt-tolerant varieties compared with sensitive varieties. The barley HVA1 gene was transformed into wheat. Transformed wheat plants showed increased tolerance to water stress, (Sivamani et al. Plant Science 155:1-9, 2000, and U.S. Pat. No. 5,981,842).

(B) Another example of improved water stress tolerance is through increased mannitol levels via the bacterial mannitol-1-phosphate dehydrogenase gene. To produce a plant with a genetic basis for coping with water deficit, Tarczynski et al. (Proc. Natl. Acad. Sci. USA, 89:2600, 1992; WO 92/19731, published No. 12, 1992; Science 259:508, 1993) introduced the bacterial mannitol-1-phosphate dehydrogenase gene, mtlD, into tobacco cells via *Agrobacterium*-mediated transformation. Root and leaf tissues from transgenic plants regenerated from these transformed tobacco cells contained up to 100 mM mannitol. Control plants contained no detectable mannitol. To determine whether the transgenic tobacco plants exhibited increased tolerance to water deficit, Tarczynski et al. compared the growth of transgenic plants to that of untransformed control plants in the presence of 250 mM NaCl. After 30 days of exposure to 250 mM NaCl, transgenic plants had decreased weight loss and increased height relative to their untransformed counterparts. The authors concluded that the presence of mannitol in these transformed tobacco plants contributed to water deficit tolerance at the cellular level. See also U.S. Pat. No. 5,780,709 and international publication WO 92/19731 which are incorporated herein by reference for this purpose.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick and Thompson, eds. (CRC Press, Inc., Boca Raton, 1993) pp. 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The transgenes described above can also be introduced into a root-rot-tolerant plant of the present invention by conventional breeding using as one parent a plant that has the transgene of interest.

Mutagenesis of Root-Rot-Tolerant Plants of the Invention

Further embodiments of the invention are the treatment of a root-rot -tolerant wheat genotype of the invention with a mutagen and the plant produced by such mutagenesis. Information about mutagens and mutagenizing seeds or pollen are presented in the IAEA's *Manual on Mutation Breeding* (IAEA, 1977) other information about mutation breeding in wheat can be found in C. F. Konzak, "Mutations and Mutation Breeding" chapter 7B, of *Wheat and Wheat Improvement*, $2^{nd}$ edition, ed. Heyne, 1987.

EXAMPLE 1

Methods for Chemical Mutagenesis of Zak, Scarlet, Macon, Hollis, Tara 2002, and Louise, and Screening of Same Mutagenesis. General embodiments of the invention comprise the use of the wheat cultivars for chemical mutagenesis. According to particular aspects, the cultivars Zak and Scarlet (5,000 seeds each) were mutagenized with ethane methyl sulfonate (EMS). Zak, Scarlet, Macon, Hollis, Tara 2002, and Louise were mutagenized with ethane methyl sulfonate (EMS; aka: ethyl methane sulfonate). Briefly, seeds were presoaked in 200 ml 50 mM sodium phosphate buffer (Ph 7.0) for 5 hr, then transferred to 200 ml of 0.3% EMS solution in phosphate buffer in a 2L flask sealed and incubated with shaking for 16 hours at 22° C. An equal volume of 10% sodium thiosulfate (w/v) was added to neutralize the EMS and allowed to stand for 5 min before washing 10 times with water, allowing the seeds to stand for 30 minutes in water between washes.

Approximately 28,000 grams of Macon grain, 16,000 gm Hollis, 18,000 gm of Tara 2002, and 29,000 gm of Louise were screened.

Screen for *Rhizoctonia* resistance. Mutagenized Zak and Scarlet are evaluated for disease reaction to *Rhizoctonia* root rot as seedlings in a growth chamber as described by Smith et al. 2003a. Briefly, two treatments are used: 1) pasteurized soil (60° C. moist heat for 30 minutes) infested with ground oat grain inoculum; and, 2) pasteurized soil only. Humidity is at 95% to limit plant transpiration and evaporative water losses from the soil. Growth conditions can be 14-hour day, with day and night temperatures of 23° C. and 11° C., respectively.

To grow *Rhizoctonia*, plastic tubes plugged with paper towel, are filled with a layer of vermiculite to aid in aeration, followed by soil/inoculum on top. Tubes are watered to near saturation and incubated 1 week to allow mycelium to colonize the soil. Two pre-germinated mutagenized seeds are planted per tube. After 3 weeks, seedlings are removed and scored for disease damage to roots.

EXAMPLE 2

The Cultivars Zak and Scarlet were Chemically Mutagenized to Provide Novel Wheat Genotypes Resistant to *R. solani, R. oryzea* and to *Pythium*; the Rz1 Genotype Segregated as a Single Gene, Semi-Dominant (Additive) Mutation As described herein, *Rhizoctonia* resistance in wheat cultivars (e.g., Zak or Scarlet) would revolutionize direct seeded spring wheat production (e.g., in the Pacific North West PNW of the United States). These resistant varieties also would serve as ideal gene donors for future variety enhancement efforts in the PNW, across the United States and worldwide, wherever soilborne disease pathogens like *Rhizoctonia* and *Pythium* are problematic. *Rhizoctonia solani* AG-8 and *R. oryzae* cause *Rhizoctonia* rot root of wheat and barley in the Pacific Northwest of the United States and in cereal production regions throughout the world. Acute (high) levels of *R. solani* AG-8 can cause bare patches in the field, as the pathogen attacks young roots after they have emerged from the seed. *R. oryzae* can cause *Rhizoctonia* damping-off, in which roots are attacked during emergence from the seed. Therefore, in particular aspects, the pathogen tolerance assays disclosed herein were conducted to monitor both seedling tolerance to *R. solani* and/or *R. oryzae*, and damping-off tolerance to *R. oryzae*.

Screening for *Rhizoctonia* root rot tolerance was performed in a wide range of chemically mutagenized spring wheat cultivars produced. In years one and two, 1085 and 1995 mutagenized plants from Zak and Scarlet, respectively, were screened for tolerance to *Rhizoctonia solani*. From this screening, a single mutant Scarlet line (015) (referred to herein as 'Rz1', or as 'RRR Scarlet') has shown reproducible tolerance. Over the past two years, 7,007 M2 lines of Macon, Hollis, Tara 2002 and Louise have been screened for tolerance to *R. solani*, and four mutants from Hollis and seven from Louise which may have tolerance to *Rhizoctonia* were isolated.

The exemplary *Rhizoctonia* tolerant Scarlet line 015 has been characterized in detail herein. Originally two Scarlet lines, 015 and 028, appeared to retest for *Rhizoctonia* root rot tolerance, but mutant 028 did not have strong tolerance so mutant 015 was characterized in most detail. The presently disclosed results with 015 show that it gives tolerance not only to *R. solani*, but also to *R. oryzea* and to *Pythium*. Nonetheless, however, line 015 is highly susceptible to strip rust, a foliar fungal pathogen, indicating that the mutation in 015 provides tolerance to necrotrophic root pathogens, but not to pathogens that infect the aerial part of the plant. This is a useful and validating result, because mutations that are too general (e.g., that generally impact resistance for many types of diseases) can have drawbacks that adversely affect agronomic performance. Scarlet mutant 015 was grown in the field in 2005, and was phenotypically indistinguishable from unmutagenized Scarlet.

In particular aspects, three backcrosses of the *Rhizoctonia* tolerant mutant to unmutagenized Scarlet (BC$_3$ to Scarlet) were completed to provide for germplasm release and to deploy the trait into adapted germplasm (e.g., for use in gene deployment strategies).

Significantly, in initial genetic analysis of BC$_1$ progeny, *Rhizoctonia* tolerance segregated 1:2:1 suggesting that it is a single gene, semi-dominant (additive) mutation (TABLES 1 and 2 below).

TABLE 1

Segregation of *Rhizoctonia*-induced disease on roots of three *Triticum aestivum* cv. RRR Scarlet (S-015 6-4) BC$_1$F$_2$ individuals.

| Line/Treatment [a] | R | I | S | n = No. of Individuals [b] |
|---|---|---|---|---|
| % Infected SR [c] | | | | |
| Scarlet wildtype, control | 8 | 0 | 0 | 8 |
| Scarlet wildtype + 400 ppg | 0 | 1 | 7 | 8 |
| BC$_1$F$_2$ S-015 6-4-1 + 400 ppg | 4 | 10 | 2 | 16 |
| BC$_1$F$_2$ S-015 6-4-2 + 400 ppg | 5 | 8 | 3 | 16 |
| BC$_1$F$_2$ S-015 6-4-4S + 400 ppg | 0 | 1 | 15 | 16 |
| Disease severity [d] | | | | |
| Scarlet wildtype, control | 8 | 0 | 0 | 8 |
| Scarlet wildtype + 400 ppg | 0 | 3 | 5 | 8 |
| BC$_1$F$_2$ S-015 6-4-1 + 400 ppg | 3 | 9 | 2 | 16 |
| BC$_1$F$_2$ S-015 6-4-2 + 400 ppg | 4 | 8 | 4 | 16 |
| BC$_1$F$_2$ S-015 6-4-4S + 400 ppg | 0 | 5 | 11 | 16 |

[a] Soil was infested with 200 propagules ger g soil *Rhizoctonia solani* C1 plus 200 propagules per g soil *Rhizoctonia oryzea* Rh 0801387 (total 400 ppg).
[b] Phenotypic classes: R, resistant; I, intermediate disease; S, susceptible. P < 0.05. n = total number of individuals. S-015 6-4-4S is a susceptible sib.
[c] Percent of seminal roots showing disease symptoms. 0-20% = R; 21-60% = I; >60% = S
[d] Disease severity was rated on a scale of 0 (no symptoms) to 4 (root lesions with stunting) 14 days post-inoculation. 0 = R; 1-2 = I; 3-4 = S

TABLE 2

Segregation of *Rhizoctonia*-induced disease on roots of six *Triticum aestivum* cv. RRR Scarlet (S-015 6-4) BC$_1$F$_3$ individuals.

| Line/Treatment [a] | R | I | S | n = No. of Individuals [b] |
|---|---|---|---|---|
| % Infected SR [c] | | | | |
| Scarlet wildtype, control | 24 | 0 | 0 | 24 |
| Scarlet wildtype + 500 ppg | 0 | 0 | 24 | 24 |
| BC$_1$F$_3$ S-015 6-4-1-1 + 500 ppg | 5 | 9 | 2 | 16 |

TABLE 2-continued

Segregation of *Rhizoctonia*-induced disease on roots of six *Triticum aestivum* cv. RRR Scarlet (S-015 6-4) BC₁F₃ individuals.

| Line/Treatment [a] | R | I | S | n = No. of Individuals [b] |
|---|---|---|---|---|
| BC₁F₃ S-015 6-4-1-2 + 500 ppg | 6 | 9 | 1 | 16 |
| BC₁F₃ S-015 6-4-2-4 + 500 ppg | 6 | 4 | 4 | 14 |
| BC₁F₃ S-015 6-4-2-5 + 500 ppg | 6 | 6 | 2 | 14 |
| BC₁F₃ S-015 6-4-1-6S + 500 ppg | 0 | 2 | 14 | 16 |
| BC₁F₃ S-015 6-4-2-7S + 500 ppg | 0 | 0 | 16 | 16 |
| Disease severity [d] | | | | |
| Scarlet wildtype, control | 24 | 0 | 0 | 24 |
| Scarlet wildtype + 500 ppg | 0 | 4 | 20 | 24 |
| BC₁F₃ S-015 6-4-1-1 + 500 ppg | 5 | 9 | 2 | 16 |
| BC₁F₃ S-015 6-4-1-2 + 500 ppg | 4 | 11 | 1 | 16 |
| BC₁F₃ S-015 6-4-2-4 + 500 ppg | 5 | 7 | 2 | 14 |
| BC₁F₃ S-015 6-4-2-5 + 500 ppg | 5 | 8 | 1 | 14 |
| BC₁F₃ S-015 6-4-1-6S + 500 ppg | 0 | 0 | 16 | 16 |
| BC₁F₃ S-015 6-4-2-7S + 500 ppg | 0 | 5 | 11 | 16 |

[a] Soil was infested with 250 propagules ger g soil *Rhizoctonia solani* C1 plus 250 propagules ger g soil *Rhizoctonia oryzae* Rh 0801387 (total 500 ppg).
[b] Phenotypic classes: R, resistant; I, intermediate disease; S, susceptible. P < 0.05. n = total number of individuals. S-015 6-4-1-6S and S-015 6-4-1-7S are susceptible sibs.
[c] Percent of seminal roots showing disease symptoms. 0-20% = R; 21-60% = I; >60% = S
[d] Disease severity was rated on a scale of 0 (no symptoms) to 7 (root lesions with severe root stunting) 14 days post-inoculation. 0 = R; 1-2 = I; 3-7 = S a. The previously isolated Scarlet line 015 is used to introduce good tolerance to *Rhizoctonia solani*, *Rhizoctonia oryzae*, and *Pythium* into the spring wheat breeding program. The first step in this process is to complete the three backcrosses to normal Scarlet required to "clean up" the after-effects of mutagenesis. Genetic analysis of the first backcross is complete. The second and third backcrosses have been made and disease rating can be used to identify useful progeny for the breeding program. Following the third backcross this gene can be deployed throughout the spring wheat breeding program.
b. The *Rhizoctonia* tolerance gene can be mapped to develop a molecular marker linked to the gene to speed deployment of the gene by reducing the amount of disease evaluation needed to identify plants carrying the desired gene.
c. The degree of tolerance or resistance imparted by the gene from line 015 can be quantified using the real time PCR technique to measure the amount of pathogen in the roots.
d. Field testing can be used to determine how well these plants perform in the field with and without disease pressure using a *Rhizoctonia* nursery developed for in-field testing of *Rhizoctonia* tolerance.

In additional aspects, the present applicants followed *Rhizoctonia* seedling tolerance in two backcrosses of Scarlet Rz1 (BC₁ and BC₂), and in two generations (F₂ and F₃ of BC₁; F₃ and F₄ of BC₂) per backcross (for a total of different four generations). The origin of Scarlet Rz1 populations used in the tolerance assays was as follows:

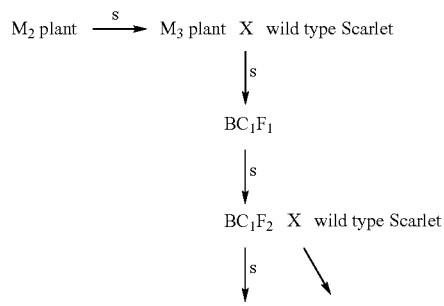

```
M₂ plant  ──s──▶  M₃ plant  X  wild type Scarlet
                              │s
                              ▼
                            BC₁F₁
                              │s
                              ▼
                            BC₁F₂  X  wild type Scarlet
                              │s
                              ▼
```

-continued

```
BC₁F₃         BC₂F₁
               │s
               ▼
              BC₂F₂
               │s
               ▼
              BC₂F₃
               │s
               ▼
              BC₂F₄
```

Key: s-self-pollinate

Figure 4:
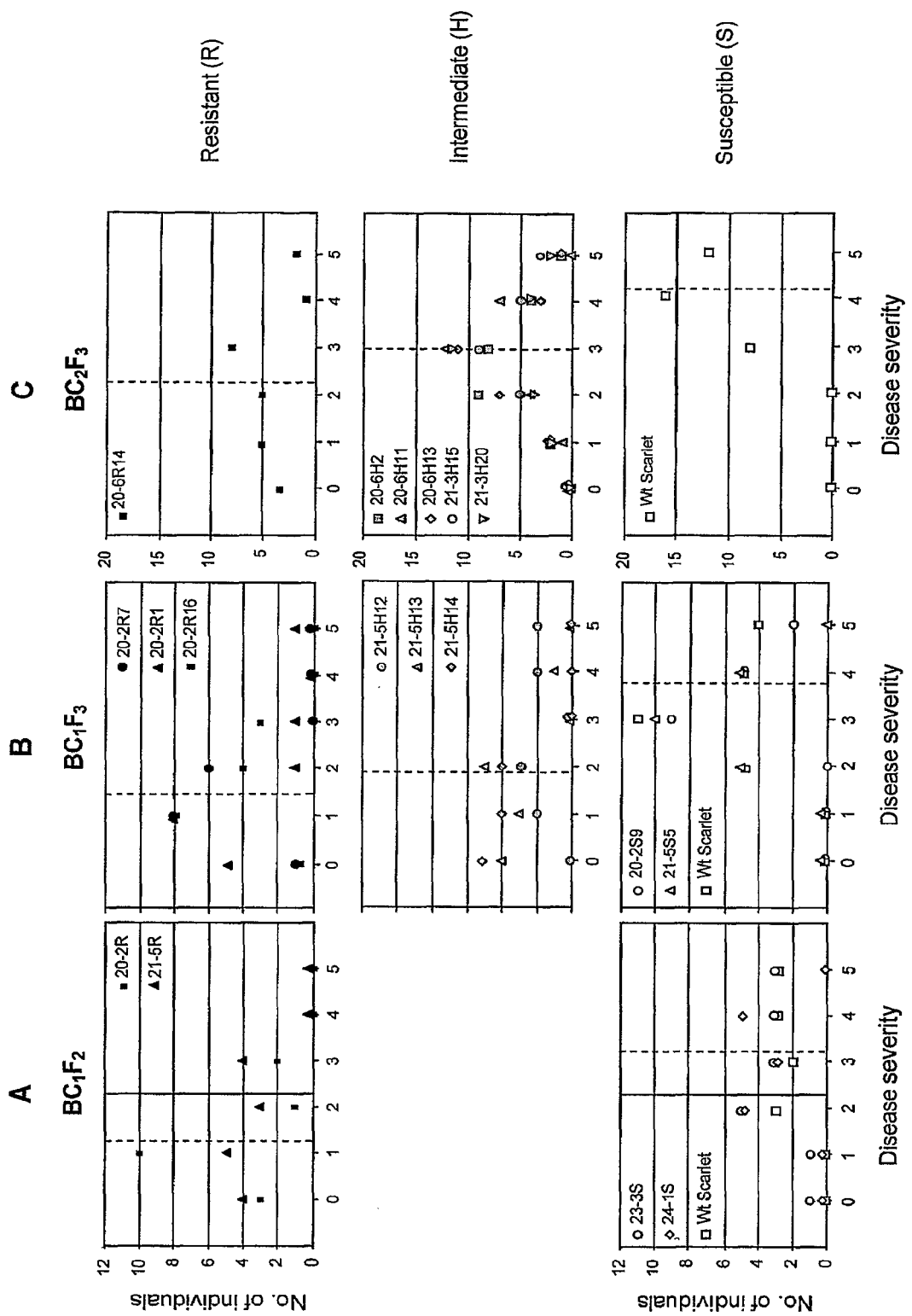
FIG. 4 shows, according to particular exemplary embodiments of the present invention, frequency of seedling tolerance in three generations of Scarlet Rz1, indicated by disease severity scores.
Figure 5:
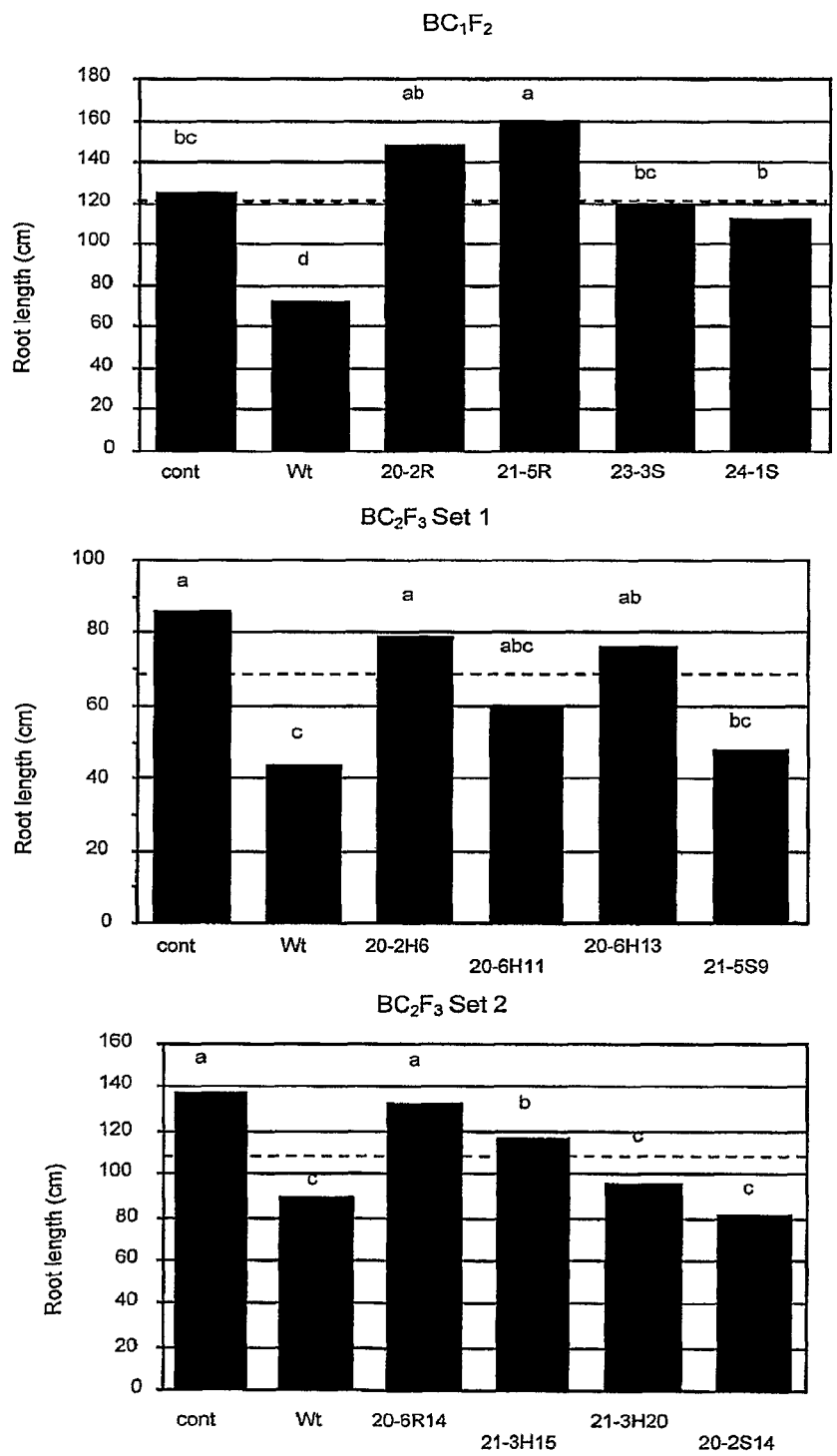
FIG. 5 shows, according to particular exemplary embodiments of the present invention, average root length values obtained from individuals of the first (BC1F2) and second (BC2F3) backcross groups of Scarlet Rz1, wild type Scarlet (Wt) and non-inoculated wild type Scarlet control ("cont").
Figure 6:
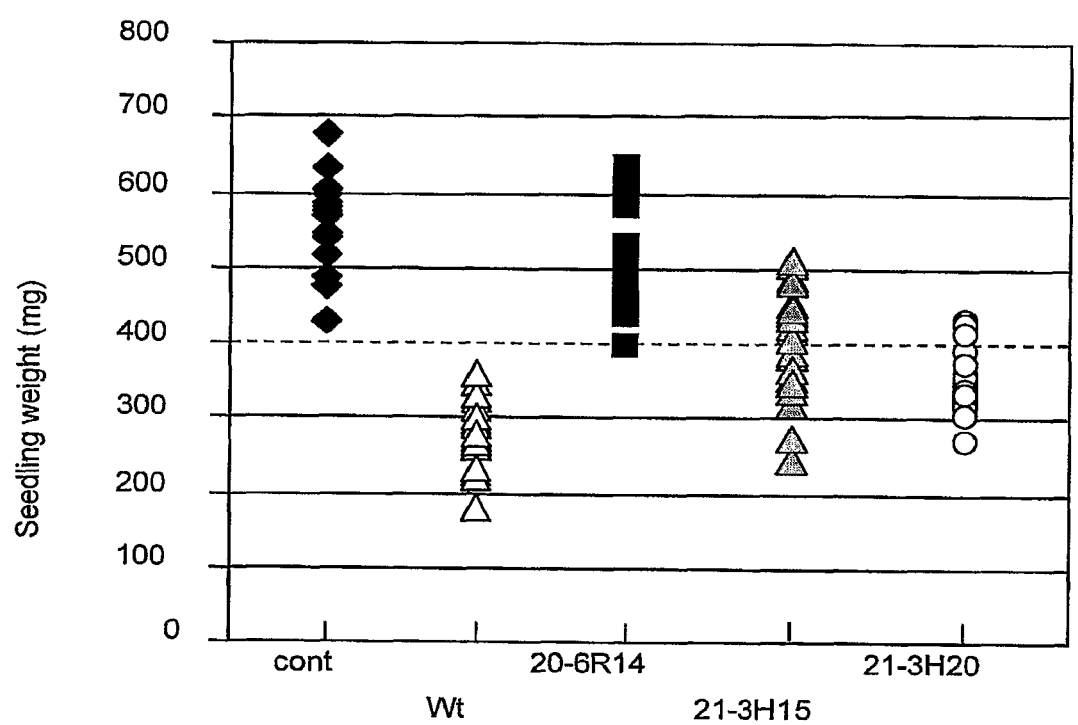
FIG. 6 shows, according to particular exemplary embodiments of the present invention, comparison of distribution of seedling weights of individuals from three BC2F3 groups of Scarlet Rz1.

*Rhizoctonia* tolerance was found to be heritable in all generations (FIGS. 4-8). The number of tolerant and susceptible individuals within each group in each of the four generations was tracked to determine whether tolerance was a single- or multi-gene trait (FIGS. 4-6).

Figure 7:
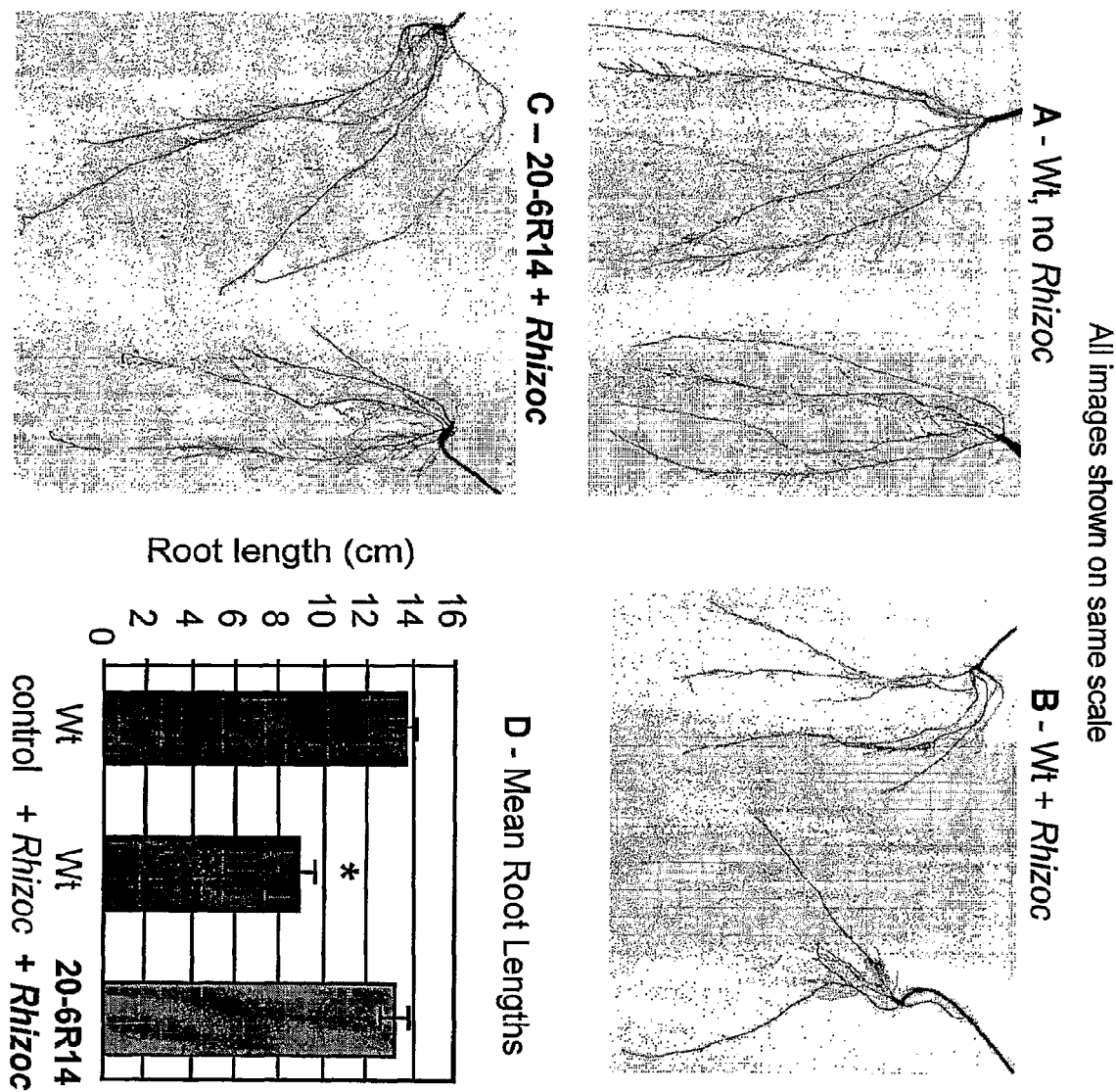
FIGS. 7A-D show, according to particular exemplary embodiments of the present invention, digital images of wild type Scarlet (Wt) (FIG. 7B) and a BC2F3 plant (20-6R14) of Scarlet Rz1 (FIG. 7C) after 14 days of growth in pasteurized Spillman (Palouse silt loam) soil infested with 400 ppg each of *Rhizoctonia solani* AG-8 C1 and *R. oryzae* 0801387.

To facilitate the assays, we used a combination of *Rhizoctonia solani* AG-8 and *R. oryzae* (equal amounts of each pathogen). Pathogen inoculum levels were adjusted to distinguish between tolerant and susceptible individuals while achieving a moderate degree of infection, that is, disease severity ratings of 4 to 6 for wild type Scarlet. It was necessary to use higher pathogen levels (inoculum) for each successive generation of Scarlet Rz1. Applicants postulate that the tolerance trait was expressed more strongly in each generation as EMS-induced mutations in other regions of the genome were eliminated by the process of gene sorting or segregation. In general, the most reliable indicators of pathogen tolerance were disease severity ratings of 0 to 1, high root fresh weights and high total root lengths (FIG. 7). Shoot growth (FIG. 8) and whole seedling weight (FIG. 6) also were positively correlated to tolerance. BC₂F₄ plants derived from group 20-6R14 and homozygous for *Rhizoctonia* tolerance were tested for seedling tolerance to *R. solani* AG-8 (FIG. 9) or *R. oryzae* (FIG. 10). A separate experiment to monitor damping-off tolerance to *R. oryzae* (FIG. 11) was conducted. All BC₂F₄ plants of Scarlet Rz1 showed tolerance in all of the assays.

Specifically, FIG. 4 shows, according to particular exemplary embodiments of the present invention, frequency of seedling tolerance in three generations of Scarlet Rz1, indicated by disease severity scores. BC1F2 groups 20-2R and 21-SR (Column A) of Scarlet Rz1 were used to derive BC1F3 groups (Column B). Second (BC2F3) backcross groups (Column C) were derived from sibs of 20-2R and 21-5R. Plants were grown for 14 days in soil infested with *R. solani* AG-8 C1 plus *R. oryzae* 0801387. BC1F2 assays were conducted using 200 ppg of each pathogen and 16 individuals per group; BC1F3 and BC2F3 assays used 250 ppg and 400 ppg of each pathogen, respectively, and 24 individuals per group. Disease severity was rated on a scale of 0 (no symptoms) to 8 (dead plant). Groups were sorted into categories according to the highest ("resistant" (R)), intermediate ("intermediate" (H)) or lowest ("susceptible" (S)) proportion of tolerant individuals within each group. The vertical dashed lines indicate the mean disease severity score for each category. Tolerance was not inherited in BC1F2 groups 23-3S and 24-1S, as all individuals in these groups displayed disease ratings of 2 or greater. However, tolerance in groups 20-2 and 20-6 was heritable in both backcross generations, because at least some individuals displayed disease ratings of 0 to 1.

FIG. 5 shows, according to particular exemplary embodiments of the present invention, average root length values obtained from individuals of the first (BC1F2) and second (BC2F3) backcross groups of Scarlet Rz1, wild type Scarlet (Wt) and non-inoculated wild type Scarlet control ("cont"). Total root length was obtained from digitized scans of roots using WinRHIZO 6.0 (Regent Instruments, Inc., Quebec, Canada). Letters indicate significant (P<0.05) differences among the means, determined using the least significant difference test (Statistix 8.1, Analytical Software, Tallahassee, Fla.). The horizontal dashed lines indicate mean values of all groups. Groups with means greater than that of Wt carried the tolerance trait. Groups with means in the same statistical class as "cont" (a) were comprised of more tolerant individuals than groups with means in the same statistical class as Wt (c). Based on this distinction, the former groups might be homozygous for the tolerance trait. Homozygous candidates include 20-2R, 21-5R, 20-2H6, 20-6H13, and 20-6R14.

FIG. 6 shows, according to particular exemplary embodiments of the present invention, comparison of distribution of seedling weights of individuals from three BC2F3 groups of Scarlet Rz1. Wild type Scarlet with (Wt) and without (cont) pathogen challenge were included as controls. Conditions for pathogen assays are as described in FIG. 5. A group that is homozygous for Rhizoctonia tolerance would consist of all individuals having seedling weights above the dotted line. Seedling weights within group 20-6R14 were clustered, very similar to those of non-inoculated Scarlet (cont), and distinct from those of Wt, indicating that 20-6R14 was homozygous for the tolerance trait. These data confirmed the findings shown in FIG. 5, which identified 20-6R14 as a possible homozygote. All progeny derived from 20-6R14 also will be homozygous for the trait.

FIGS. 7A-D show, according to particular exemplary embodiments of the present invention, digital images of wild type Scarlet (Wt) (FIG. 7B) and a BC2F3 plant (20-6R14) of Scarlet Rz1 (FIG. 7C) after 14 days of growth in pasteurized Spillman (Palouse silt loam) soil infested with 400 ppg each of Rhizoctonia solani AG-8 C1 and R. oryzae 0801387. More details of growth conditions are discussed in the comments to FIG. 8. Wt without pathogen treatment (FIG. 7A) is shown as a control. FIG. 7D shows mean root lengths of plants from the above treatments. Twelve and 24 individuals were sampled for wild type Scarlet (Wt) and group 20-6R14, respectively. Asterisk indicates significant (P<0.05) differences among the means determined using the least squares method (Statistix vers 8.1, Tallahassee, Fla.). Root growth in 20-6R14 plants was significantly greater than Wt after pathogen treatment, indicating tolerance in 20-6R14 plants.

Figure 8:
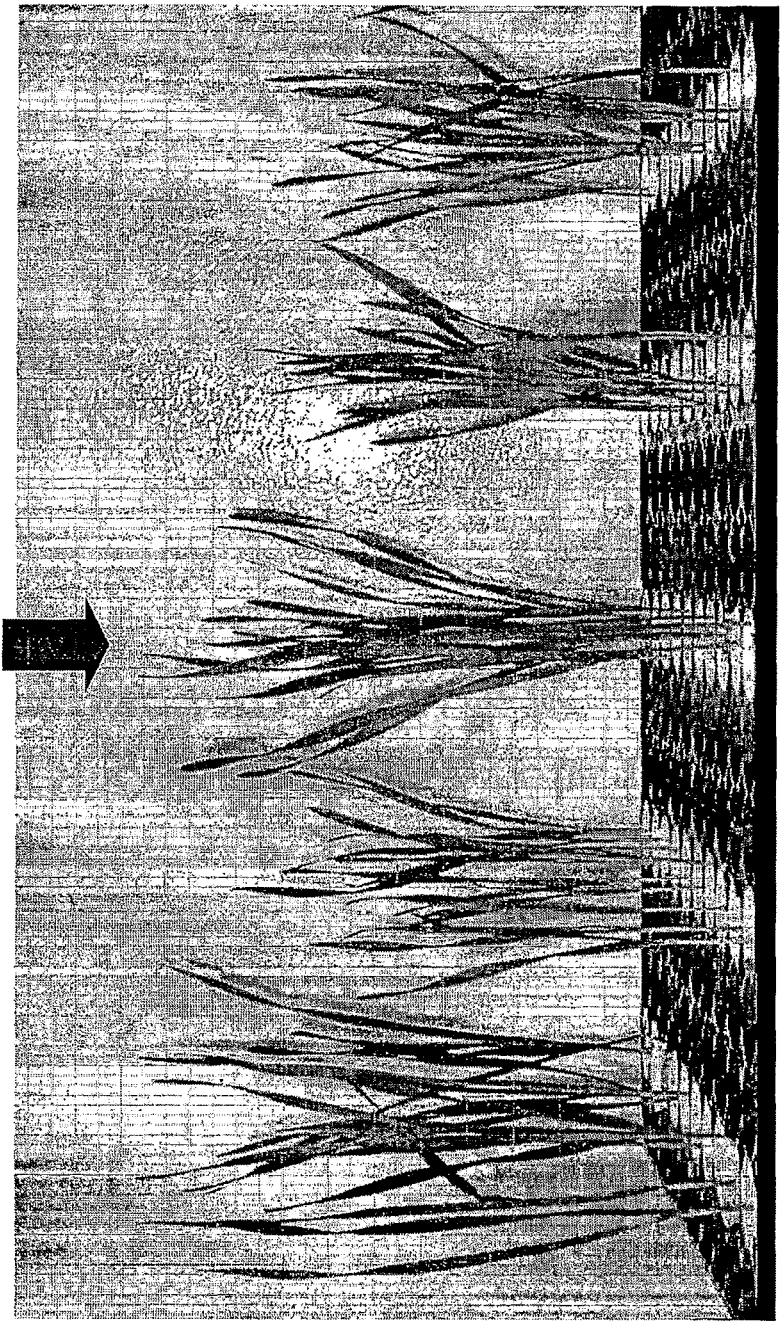
FIG. 8 shows, according to particular exemplary embodiments of the present invention, comparison of shoot height in 14-day-old Scarlet wild type (Wt), plants of BC2F3 group 20-6R14, and susceptible sibs of 20-6R14, all used for FIG. 7.

FIG. 8 shows, according to particular exemplary embodiments of the present invention, comparison of shoot height in 14-day-old Scarlet wild type (Wt), plants of BC2F3 group 20-6R14, and susceptible sibs of 20-6R14, all used for FIG. 7. Seedlings were germinated for 2 to 4 days prior to sowing in pasteurized Spillman (Palouse Silt Loam) soil infested with a combination of Rhizoctonia solani AG-8 C1 and R. oryzae 0801387 (400 propagules per gram soil of each isolate). Plants were grown in the greenhouse at 15° C.±1° C. with 12 hours per day supplemental lighting. The 12 hr per day refers to supplemental lighting only; the "total" photoperiod was day length of natural light. Tolerance in Scarlet Rz1 group 20-6R14 is indicated by a noticeable increase in shoot length compared to sibs of 20-6R14 and to Wt. This increased shoot length is comparable to uninoculated Wt control plants.

Figures 9A, 9B:
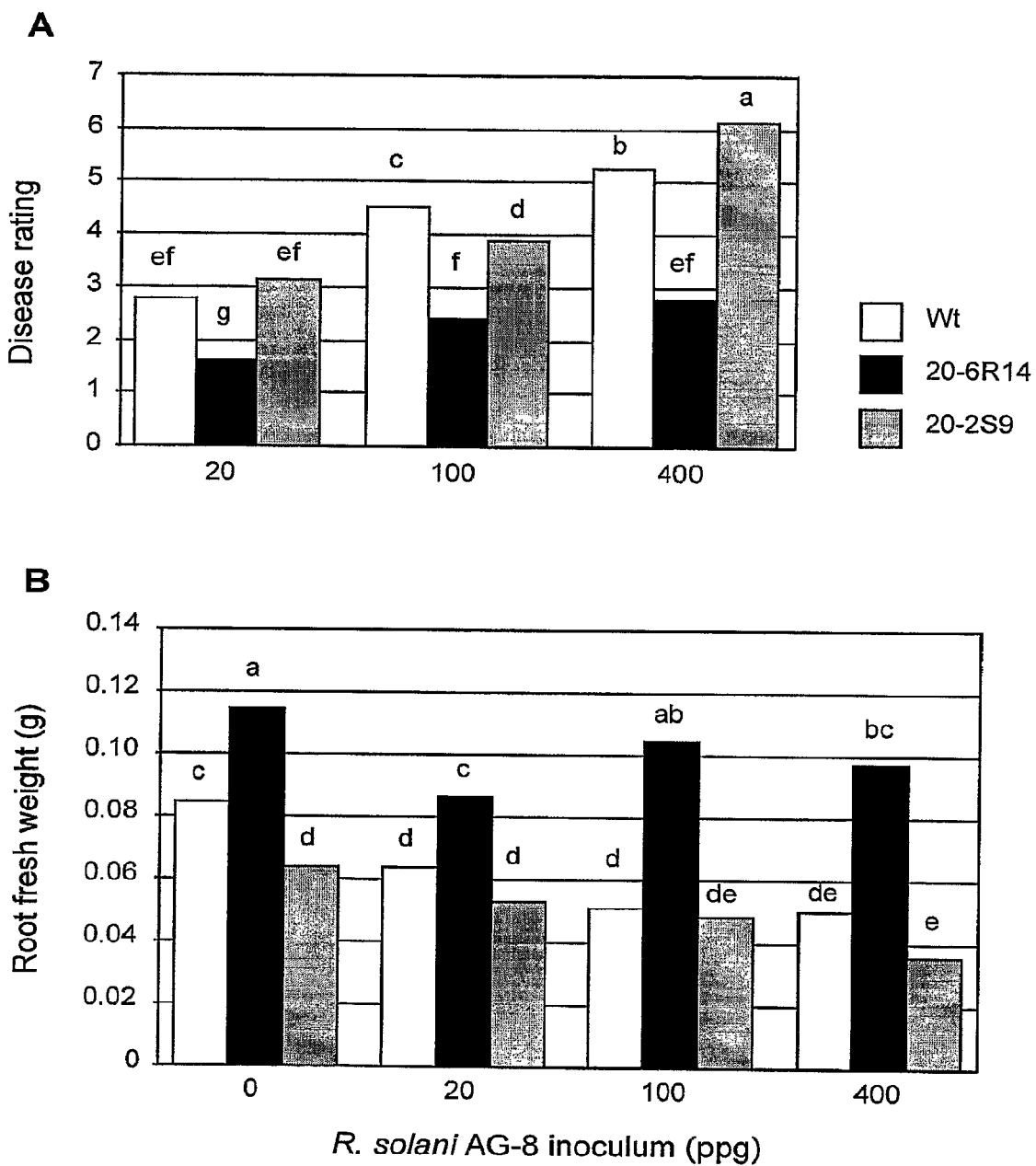
FIGS. 9A and B show, according to particular exemplary embodiments of the present invention, seedling tolerance of BC2F4 group 20-6R14 to *R. solani* AG-8 isolate C1

FIGS. 9A and B show, according to particular exemplary embodiments of the present invention, seedling tolerance of group 20-6R14 to R. solani AG-8 isolate C1. Twenty four individuals of the BC2F4 group 20-6R14 from Scarlet Rz1 or 20-2S9 (BC1F3 susceptible sib of Scarlet Rz1) were grown in soil infested with 20, 100 and 400 ppg of the pathogen. Twelve plants of wild type Scarlet (Wt) were included as a control. Disease severity was rated on a scale of 0 (no symptoms) to 8 (dead plant) after 14 days. Mean disease severity (FIG. 9A) was significantly decreased and root weight (FIG. 9B) was significantly enhanced in Line 20-6R14 compared to Wt and Scarlet Rz1 susceptible sibs at all pathogen levels. Letters indicate significant (P<0.05) differences among the means, determined using the least significant difference test (Statistix 8.1, Analytical Software, Tallahassee, Fla.). Reduced disease severity ratings and enhanced root weights in 20-6R14 indicate tolerance to levels of R. solani AG-8 as high as 400 ppg (or about 6 to 10 times higher than levels found in the field) is present in the BC2F4 generation of Scarlet Rz1.

Figures 10A, 10B:
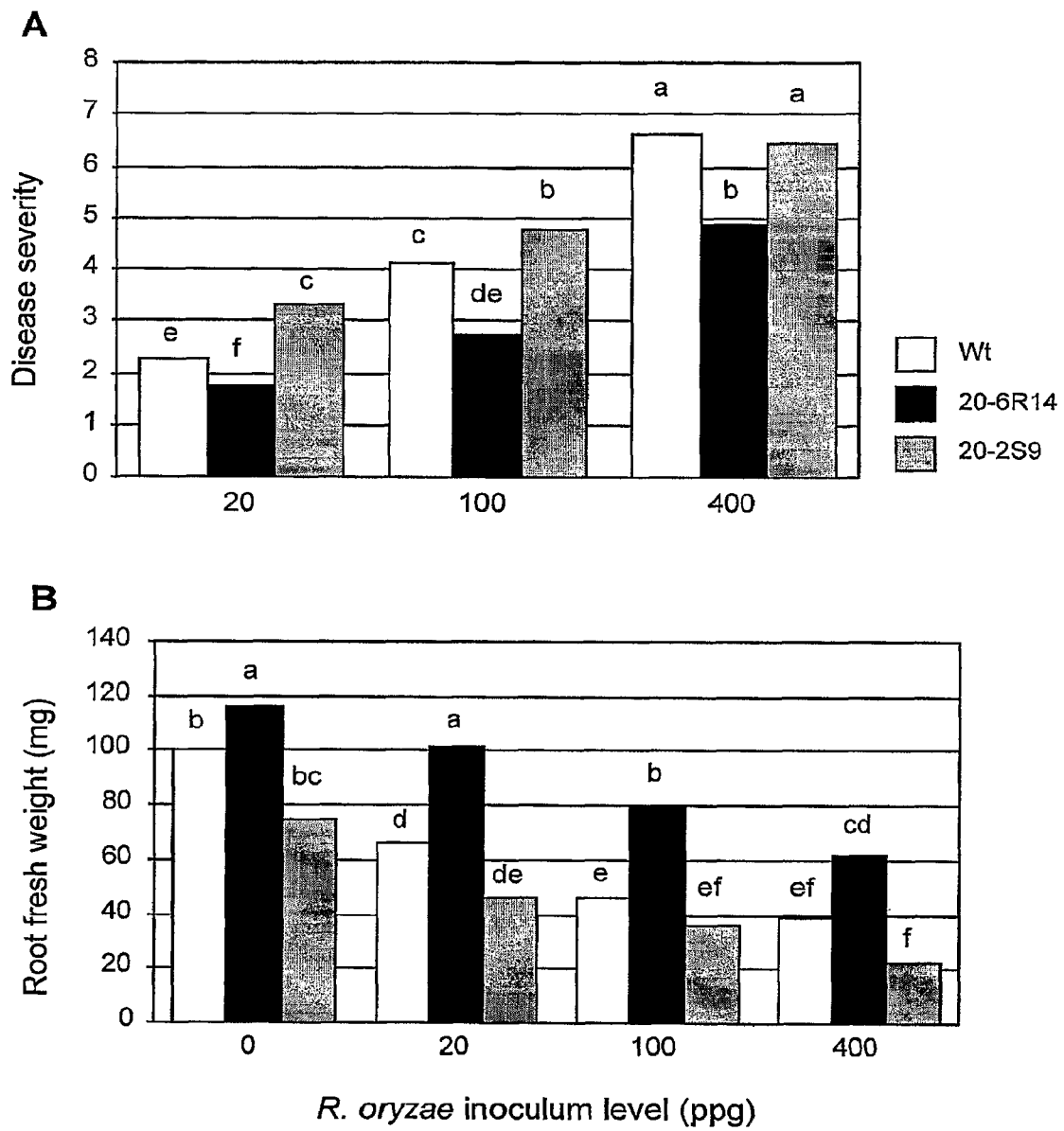
FIGS. 10A and B show, according to particular exemplary embodiments of the present invention, seedling tolerance of BC2F4 group 20-6R14 to *R. oryzae* isolate 0801387

FIGS. 10A and B show, according to particular exemplary embodiments of the present invention, seedling tolerance of 20-6R14 to R. oryzae isolate 0801387. Twenty four individuals of the BC2F4 group 20-6R14 of Scarlet Rz1 or 20-2S9 (BC1F3 susceptible sib) were grown in soil infested with 20, 100 and 400 ppg of the pathogen. Twelve plants of wild type Scarlet (Wt) were included as a control. Disease severity was rated on a scale of 0 (no symptoms) to 8 (dead plant) after 14 days. Mean disease severity (FIG. 10A) was decreased and root weight (FIG. 10B) was enhanced in Line 20-6R14 compared to Wt and the Scarlet Rz1 susceptible sibs at all inoculum levels. Letters indicate significant (P<0.05) differences among the means, determined using the least significant difference test (Statistix 8.1, Analytical Software, Tallahassee, Fla.). Reduced disease severity ratings and enhanced root weights in 20-6R14 indicate tolerance to levels of R. oryzae as high as 400 ppg (or about 6 to 10 times higher than levels found in the field) is present in the BC2F4 generation of Scarlet Rz1.

Figure 11A:
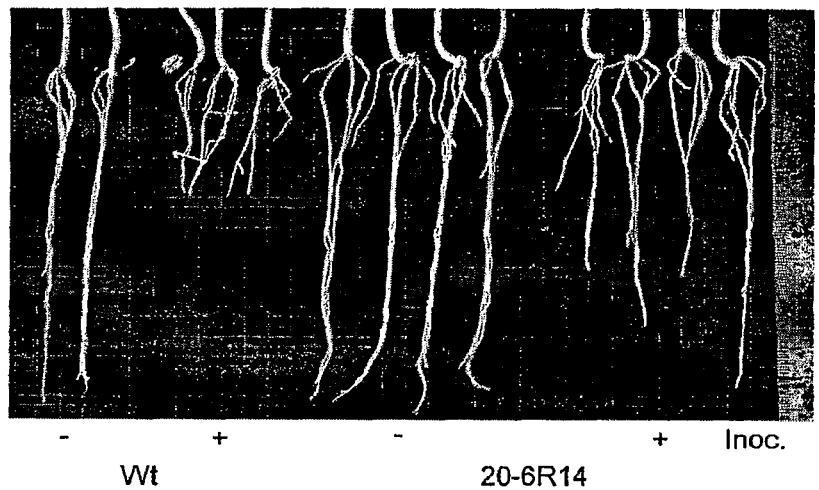
FIGS. 11A, B and C show, according to particular exemplary embodiments of the present invention, damping-off tolerance to *R. oryzae* in BC2F4 individuals of group 20-6R14 of Scarlet Rz1
Figure 11B:
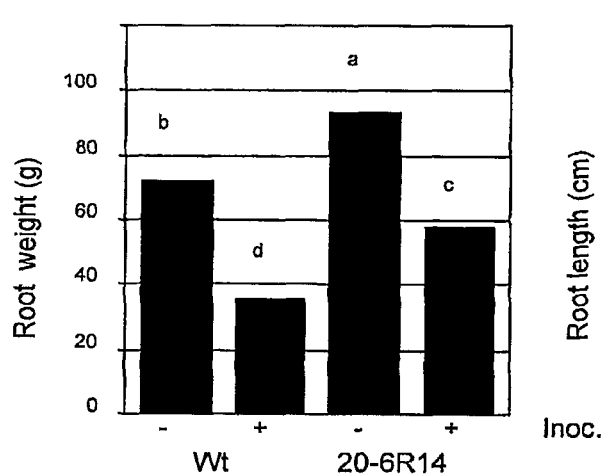
Figure 11C:
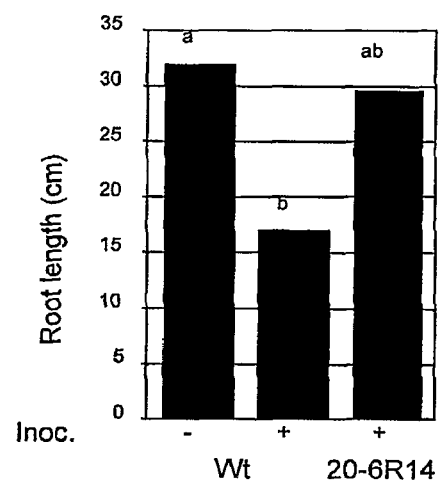

FIGS. 11A, B and C show, according to particular exemplary embodiments of the present invention, damping-off tolerance to R. oryzae in BC2F4 individuals of group 20-6R14 of Scarlet Rz1. Damping-off tolerance is tested by sowing seed directly into infested soil, rather than allowing the seeds to sprout for 2 to 3 days before planting. Seeds were sown in soil infested with 400 ppg R. oryzae 0801387, then evaluated for root development after 8 days. FIG. 11A shows examples of typical root growth of wild type Scarlet (Wt) and 20-6R14 plants. FIG. 11B shows root fresh weight of wild type Scarlet and group 20-6R14 (mean of 24 individuals). FIG. 11c shows total root length obtained using WinRHIZO 6.0 (Regent Instruments, Inc., Quebec, Canada). Letters indicate significant (P<0.05) differences among the means, determined using the least significant difference test (Statistix 8.1, Analytical Software, Tallahassee, Fla.). Both root weight and total root length were higher in 20-6R14 compared to Wt. The data indicate that Scarlet Rz1 carries damping-off tolerance in addition to seedling tolerance to R. oryzae.

In summary, four generations of Scarlet Rz1 (see TABLE 3 below) were tested for tolerance to Rhizoctonia solani AG-8 isolate C1 and R. oryzae isolate 0801387. For seedling tolerance assays, plants were germinated on moist filter paper in Petri plates for 2 to 4 days prior to sowing in

*Rhizoctonia*-infested soil. For damping-off tolerance assays, seeds were sown directly into *Rhizoctonia*-infested soil. All assays were carried out on plants individually grown in 6-inch plastic containers (Stuewe & Sons, Corvallis, Oreg.) containing 70 g of pasteurized Spillman soil with or without the pathogens. Plants were maintained at 15±1° C., with 12 h daily supplemental lighting (66 to 90 umol/m$^2$/sec). Roots of each plant were washed free of soil and rated for disease symptoms on a scale of 0 (no symptoms) to 8 (dead plant). Shoot length and root fresh weight data were obtained. Digital images of roots were generated using a HP ScanJet 5370 (Hewlett Packard, Palo Alto, Calif.), and total root length was determined using WinRHIZO 5.0 (Regent Instruments, Inc., Quebec, Canada). Individual plants showing good tolerance in the assays were "rescued" by transplantation to pots of soil without pathogen, and grown in the greenhouse for advancement to the next generation. In these cases, seedlings were left intact and root weights could not be taken.

TABLE 3

Assay details for each generation of Scarlet Rz1 are summarized below.

| Generation | Pathogen[1] | Tolerance[2] | Inoculum[3] | Plant age[4] | No. tested[5] | FIG. |
|---|---|---|---|---|---|---|
| BC$_1$F$_2$ | Rs + Ro | seedling | 400 ppg | 14 days | 16 | 4-5 |
| BC$_1$F$_3$ | Rs + Ro | seedling | 500 ppg | 14 days | 24 | 4-5 |
| BC$_2$F$_3$ | Rs + Ro | seedling | 800 ppg | 14 days | 24 | 4-6 |
| BC$_2$F$_4$ | Rs or Ro | seedling | 400 ppg | 14 days | 24 | 9, 10 |
|  | Ro | damping-off | of each | 8 days | 24 | 11 |

[1]Rs—*R. solani* AG-8 isolate C1; Ro—*R. oryzae* isolate 0801387.
[2]Type of tolerance tested.
[3]Total for both pathogens except in assays of BC$_2$F$_4$.
[4]Age of plants at the time of harvest.
[5]Number of individuals of each genotype tested in the assays.

The disclosed findings indicate that *Rhizoctonia* tolerance is conferred by a single co-dominant gene or locus. Applicants also identified a BC$_2$F$_3$ group (20-6R14) in which all tested individuals gave highly uniform responses to the pathogens (example in FIG. 6). The trait for tolerance appeared to be homozygous in this group, and is expected to be homozygous in all generations derived from this group.

EXAMPLE 3

The Rz1 Genotypes were also Demonstrated to be *Pythium* Tolerant

The following Example shows, according to exemplary aspects of the present invention, that the Scarlet Rz1 genotypes were also demonstrated to be *Pythium* tolerant.
Example Overview/Background:

*Pythium* root rot, caused by *Pythium* species, occurs in virtually all wheat fields in Washington State (Cook and Veseth, 1991, Paulitz and Adams, 1993), and this disease may be the most yield-limiting disease of wheat in North America (Cook and Veseth, 1991). *Pythium* spp. cause a decrease in root mass, which leads to poor nutrient uptake, resulting in variable crop stands, decreased tiller numbers, varying maturity dates and yield losses (Weller and Cook, 1986). Grain yields of wheat grown in *Pythium*-free soil have been reported to be 15% to 25% higher than those of wheat grown in *Pythium* infested soil (Cook and Haglund, 1991, Cook et al. 1987, Cook et al., 1980, Hering et al. 1987, Weller and Cook, 1986). If embryo damage is severe, seedlings often fail to emerge when infected with *Pythium* (Fukui et al., 1994). *Pythium* root rot is prevalent in cool, wet soils covered with crop debris (Cook and Haglund 1991, Cook et al. 1987, Cook and Veseth, 1991), which is typical of direct-seeded wheat fields. An increased awareness of the environmental impacts of traditional tillage practices, such as wind and water erosion, nutrient leaching, and decreased soil organic matter, has caused many growers to shift to direct-seeded wheat production (Pannkuk et al., 1987, Weller and Cook, 1986). This shift in production practices provides *Pythium* species with an optimal environment for infecting wheat crops (Cook 1992, Cook et al. 1990). Chamswarng and Cook (1985) isolated and identified 10 *Pythium* species from soils in eastern Washington that were pathogenic to wheat. They found *P. aristosporum*, *P. volutum*, *P. ultimum*, *P. sylvaticum* complex, and *P. irregulare* to be the most virulent of the isolates they identified. Ingram and Cook (1990) assessed the pathogenicity of four *Pythium* species on wheat, peas, lentils, and barley, and *P. ultimum* and *P. irregulare* were the most virulent species to wheat, which agreed with other reports (Chamswarng and Cook, 1985). In a recent study, Higginbotham et al. (2003) detected differences between species and among isolates within species of *Pythium* collected from wheat fields throughout Eastern Washington (Paulitz and Adams, 2003). *Pythium debaryanum* isolate 90136 and *P. ultimam* isolate 90039 were the most virulent of the isolates evaluated (Higginbotham et al. 2003), and may prove useful in future disease screenings of *Triticum* germplasm where identifying genetic resistance for highly virulent isolates is the goal.

Higginbotham et al. (2004a, 2004b) recently evaluated the level of tolerance to *Pythium* root rot among a diverse set of wheat germplasm collected from all major wheat production regions in the United States. *Pythium debaryanum* isolate 90136 and *P. ultimum* isolate 90038, identified as the most virulent *Pythium* isolates on wheat, were used to infest pasteurized soil, which was seeded with wheat genotypes and placed in a growth chamber maintained at a constant 16° C., 12 hr photoperiod and ambient humidity (Higginbotham et al. 2004a). Length of the first leaf and plant height measurements were recorded, and roots were digitally scanned to create computer files that were analyzed using WinRhizo software. Significant (P<0.05) differences in susceptibility were detected among wheat genotypes in the presence of both *Pythium* species, and a significant (P<0.0001) correlation between plant stunting and root loss was detected (Higginbotham et al. 2004b). Based on both shoot and root measurements, Caledonia, Chinese Spring, MN97695 and OR942504 appear to be highly susceptible to *Pythium* root rot, whereas genotypes KS93U161, OH708 and Sunco were the most tolerant to this disease. Genotypes with high levels of tolerance may be useful gene donors for cultivar improvement efforts.

Example Overview References:

Chamswarng, C. and R. J. Cook. 1985. Identification and comparative pathogenicity of *Pythium* species from wheat roots and wheat-field soils in the Pacific Northwest. Phytopathology 75:821-827.

Cook, R. J. 1990. Diseases caused by root-infecting pathogens in dryland agriculture. Advances in Soil Science 13:215-239.

Cook, R. J. 1992. Wheat root health management and environmental concern. Can. J. Plant Pathol. 14:76-85.

Cook, R. J., and W. A. Haglund. 1991. Wheat yield depression associated with conservation tillage caused by root pathogens in the soil not phytotoxins from the straw. Soil Biol. Biochem. 23:1125-1132.

Cook, R. J., J. W. Sitton and J. T. Waldher. 1980. Evidence for *Pythium* as a pathogen of direct-drilled wheat in the Pacific Northwest. Plant Dis. 64:102-103.

Cook, R. J., J. W. Sitton and W. A. Haglund. 1987. Influence of soil treatments on growth and yield of wheat and implications for control of *Pythium* rot. Phytopathology 77:1192-1198.

Cook, R. J. and R. Veseth. 1991. Wheat Health Management. The American Phytopathological Society. St. Paul, Minn.

Fukui, R., G. S. Campbell and R. J. Cook. 1994. Factors influencing the incidence of embryo infection by *Pythium* spp. during germination of wheat seeds in soils. Phytopathology 84:695-702.

Hering, T. F., R. J. Cook and W.-H. Tang. 1987. Infection of wheat embryos by *Pythium* species during seed germination and the influence of seed age and soil matric potential. Phytopathology 77:1104-1108.

Higginbotham, R. W, Paulitz, T. C., Campbell, K. G., Kidwell, K. K. 2004b. Evaluation of adapted wheat cultivars for tolerance to *Pythium* root rot. Plant Disease: submitted.

Higginbotham, R. W., Paulitz, T. C. and Kidwell, K. K. 2004a. Virulence of *Pythium* spp. isolated from wheat fields in eastern Washington. Plant Disease: submitted.

Higginbotham, R. W., T. C. Paulitz and K. K. Kidwell. 2003. Virulence of *Phythium* species isolated from wheat fields in Eastern Washington. Plant Disease (submitted).

Ingram, D. M., and Cook, R. J. 1990. Pathogenicity of four *Pythium* species to wheat, barley, peas and lentils. Plant. Pathol. 39:110-117.

Pannkuk, C. D., R. I., Papendick and K. E. Saxton. 1997. Fallow management effects of soil water storage and wheat yields in the Pacific Northwest. Agronomy Journal 89:386-391

Paulitz, T. C. and K. Adams. 2003. Composition and distribution of *Pythium* communities in wheat fields in eastern Washington State. Phytopathology 93: 867-873.

Weller, D. M. and R. J. Cook. 1986. Increased growth of wheat by seed treatments with fluorescent pseudomonads, and implications of *Pythium* control. Can. J. Plant Pathol. 8:328-334.

Methods for this Example:

Two groups of Scarlet Rz1 $BC_1F_2$, designated 20-6 and 21-3, were sibs of groups 20-2R and 21-5R that were used in the *Rhizoctonia* experiments described herein above. Furthermore, tolerant individuals from groups 20-6 and 21-3 were used to produce the $BC_2F_3$ and $BC2F_4$ generations that displayed *Rhizoctonia* tolerance.

Seedling germination and growth conditions for *Pythium* tolerance assays were essentially as described for that of *Rhizoctonia* spp. Twenty-four seedlings of groups 20-6 and 21-3 were sown in pasteurized Spillman (Palouse silt loam) soil infested with 1000 propagules per gram (ppg) each of *Pythium ultimum* isolate 0900119 plus *P. irregulare* isolate 0900101. Both isolates are highly pathogenic to wheat and barley (Higginbotham et al. 2004; Ingram and Cook 1990; Paulitz and Adams 2003). Plants were harvested 14 days after growth in the *Pythium*-infested soil. First leaf length (mm) and total root length (cm) were used to evaluate tolerance. Total root length was determined using WinRHIZO 5.0 (Regent Instruments, Inc., Quebec, Canada). Analysis of variance was done using Statistix vers. 8.1 (Analytical Software, Tallahassee, Fla.).

Results for this Example:

*Pythium* damage is subtle, and roots cannot be rated for disease symptoms as in the case of *Rhizoctonia* damage. However, the length of the first true leaf is a reliable indicator of *Pythium* damage (Higginbotham et al. 2004), as seedling roots that are attacked early by *Pythium* do not support normal foliar growth. Root length also is impacted by *Pythium* attack.

Figure 12:
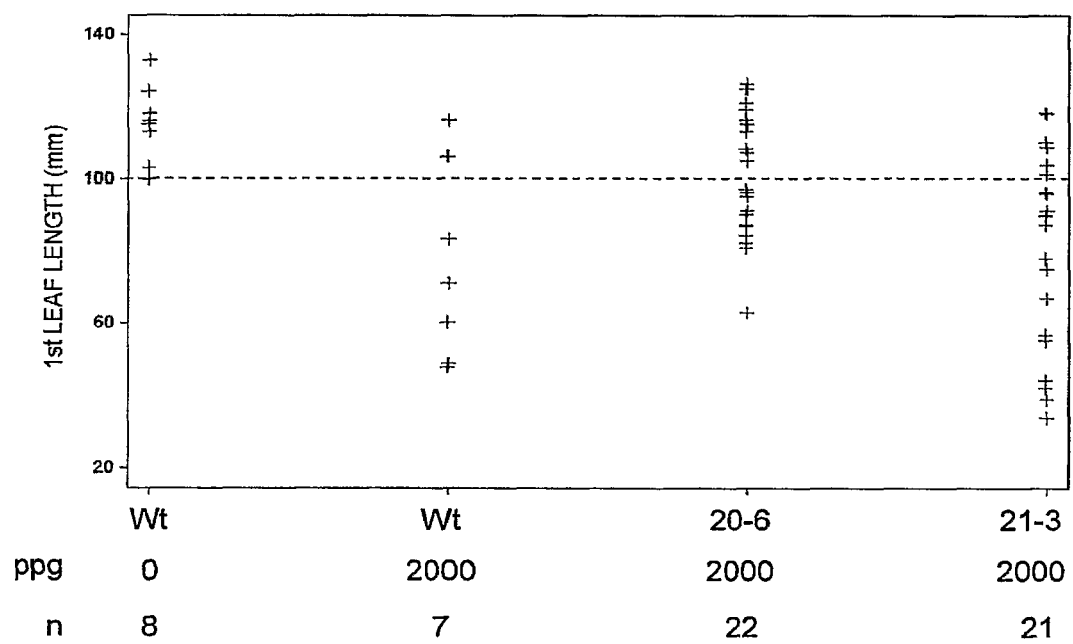
FIG. 12 shows, according to particular exemplary embodiments of the present invention, *Pythium* tolerance in Scarlet Rz1 as indicated by distribution of first leaf length (rum) among individuals of Scarlet wild type (Wt) and Scarlet Rz1 BC1F2 populations P20-6 and P21-3. Seedlings were germinated for 2 to 4 days, then grown for 14 days in pasteurized Spillman soil infested with 1000 propagules per gram (ppg) each of *Pythium ultimum* isolate 0900119 and 1000 ppg *P. irregulare* grp I isolate 0900101.

Tolerance to a combination of *P. ultimum* and *P. irregulare* grp I was observed in Scarlet Rz1 $BC_1F_2$ groups 20-6 and 21-3. A proportion of plants within a $BC_1F_2$ group are expected to be heterozygous for pathogen tolerance and show an intermediate degree of tolerance, whereas some plants will be homozygous for either tolerance (strong tolerance) or susceptibility (no tolerance). Uninoculated wild type Scarlet displayed leaf length values above 100 mm, whereas *Pythium*-challenged wild type Scarlet generally showed leaf length values below 100 mm. As expected for a $BC_1F_2$ group, the $BC_1F_2$ plants showed a range of leaf length values (FIG. 12). Mean leaf length values are shown in TABLE 4.

Specifically, FIG. 12 shows distribution of first leaf length (mm) among individuals of Scarlet wild type (Wt) and Scarlet Rz1 BC1F2 populations P20-6 and P21-3. Seedlings were germinated for 2 to 4 days, then grown for 14 days in pasteurized Spillman soil infested with 1000 propagules per gram (ppg) each of *Pythium ultimum* isolate 0900119 and 1000 ppg *P. irregulare* grp I isolate 0900101. Length of the first true leaf was measured at 14 days. The dotted line is the mean leaf length derived from all individuals, and delineates uninoculated wild type Scarlet plants from inoculated plants that sustained *Pythium* damage. Many plants within BC1F2 group 20-6 and several from group 21-3 had first leaf length values that fell above the dotted line. The findings indicate that these plants were tolerant to a combination of *P. ultimum* and *P. irregulare* to an extent that they resembled uninoculated wild type Scarlet plants. n=number of individuals screened.

TABLE 4

Demonstration of *Pythium* tolerance in two $BC_1F_2$ groups (20-6 and 21-3) of Scarlet Rz1.

| Population/Treatment [a] | Leaf length (mm) [b] | Total root length (cm) [b, c] |
|---|---|---|
| Scarlet wild type, control | 115 ± 3.8 | 120 ± 9.7 |
| Scarlet wild type + 2000 ppg | 76 ± 10 | 35 ± 6.3 |

TABLE 4-continued

Demonstration of *Pythium* tolerance in two
BC$_1$F$_2$ groups (20-6 and 21-3) of Scarlet Rz1.

| Population/Treatment [a] | Leaf length (mm) [b] | Total root length (cm) [b, c] |
|---|---|---|
| 20-6 + 2000 ppg | 102 ± 3.7* | 50 ± 3.6* |
| 21-3 + 2000 ppg | 80 ± 5.9 | 52 ± 4.9* |

20-6 and 21-3 were sibs of groups 20-2R and 21-5R that were used in the *Rhizoctonia* experiments. Furthermore, tolerant individuals from groups 20-6 and 21-3 were used to produce the BC$_2$F$_3$ and BC$_2$F$_4$ generations that displayed *Rhizoctonia* tolerance. Leaf length and root length were measured in plants grown 14 days in pasteurized Spillman (Palouse silt loam) soil infested with a combination of 1000 propagules per gram (ppg) *P. ultimum* isolate 0900119 and 1000 ppg *P. irregulare* grp I isolate 0900101. Mean first leaf length of plants in group 20-6 was significantly (P < 0.05, *) greater than that of Scarlet wild type after *Pythium* treatment. Mean total root length of both 20-6 and 21-3 also were significantly (P < 0.05, *) greater than that of Scarlet wild type after *Pythium* challenge. The data indicate that enhanced tolerance to *Pythium* is present in both BC$_1$F$_2$ groups.
[a] Soil was infested with 1000 propagules g$^{-1}$ soil each of *P. ultimum* 0900119 and *P. irregulare* grp 10900101 (total 2000 ppg).
[b] Means and standard errors of leaf length were determined after 14 days of growth in infested soil.
[c] Means and standard errors of total root length were obtained for 14-day-old plants using WinRHIZO 5.0 (Regent Instruments, Inc., Quebec, Canada). soil.
[c] Means and standard errors of total root length were obtained for 14-day-old plants using WinRHIZO 5.0 (Regent Instruments, Inc., Quebec, Canada).

The plants from each BC$_1$F$_2$ group were divided into three arbitrary classes based on first leaf length (L): (R) or strong tolerance, where L>100; (I) or intermediate tolerance, where 80≤L≤100; and (S) or susceptible, where 30<L<80. Significant (P<0.05) differences of the means of each class were observed (FIG. 13), indicating that tolerance to *Pythium* is segregating among individuals of the BC$_1$F$_2$ groups, as expected.

Figure 13:
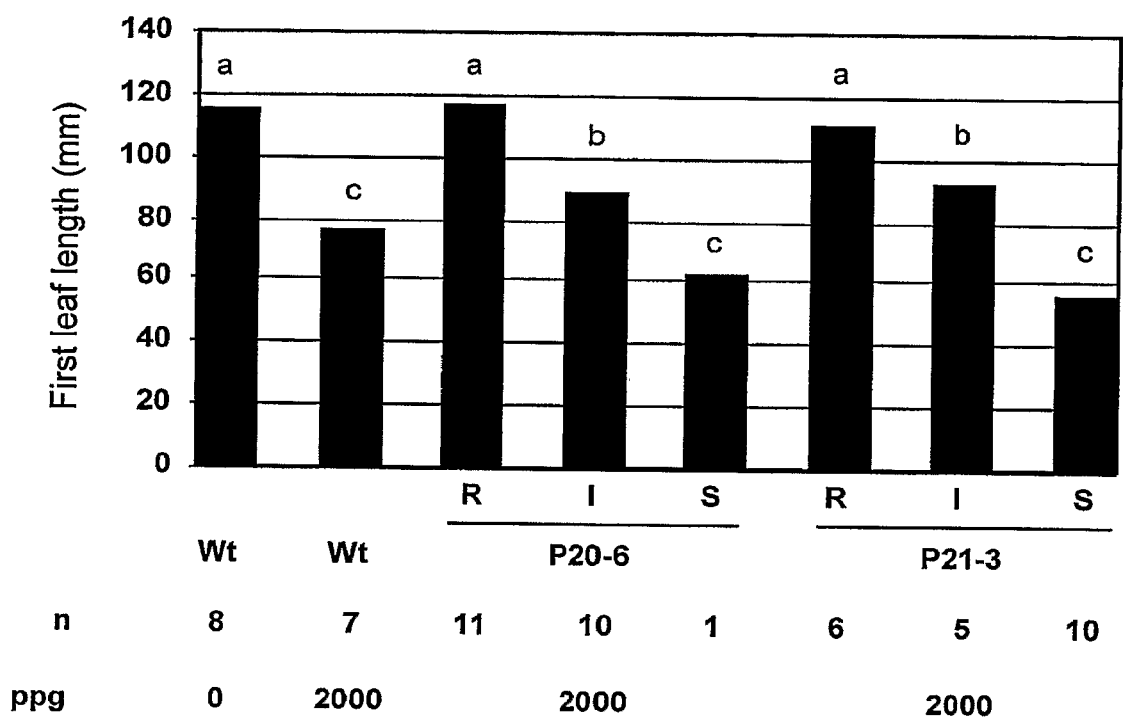
FIG. 13 shows, according to particular exemplary embodiments of the present invention, that a proportion of plants within a BC1F2 group are expected to be heterozygous for *Pythium* tolerance and show an intermediate degree of tolerance, whereas some plants will be homozygous for either tolerance (strong tolerance) or susceptibility (no tolerance).

Specifically, FIG. 13 shows that a proportion of plants within a BC1F2 group are expected to be heterozygous for *Pythium* tolerance and show an intermediate degree of tolerance, whereas some plants will be homozygous for either tolerance (strong tolerance) or susceptibility (no tolerance). Controls and growth conditions are as described in FIG. 12. Plants in BC1F2 groups 20-6 and 21-3 were sorted into three arbitrary classes based on first leaf length: (R) or strong tolerance, where L>100; (I) or intermediate tolerance, where 80≤L≤100; and (S) or susceptible, where 30<L<80. Letters above the bars indicate significant (P<0.05) differences among the means of each class were observed, indicating that tolerance to *Pythium* is segregating among individuals of the BC1F2 groups, as expected. Without the sorting, leaf length values of tolerant (R) plants would be averaged with susceptible (S) plants, with no apparent overall tolerance.

Individual plants from the R (strong tolerance) and S (susceptible) leaf length classes were picked at random for root length analysis. Total root length values appeared to be segregating among individuals of 20-6 and 21-3, and those plants with longer leaf length also had longer roots. Mean total root length values for all groups are given in TABLE 4. In the R class, a small but significant (P<0.05) increase in root length was observed in *Pythium*-challenged BC1F$_2$ plants compared to *Pythium*-challenged wild type Scarlet (FIG. 14). *Pythium* tolerance was therefore indicated by enhancement of both foliar and root growth. A small degree of root length enhancement in tolerant plants is expected because other EMS mutations that reduce plant health are likely present in the BC1F$_2$ generation; these would be eliminated in subsequent generations by gene or chromosome sorting.

Figure 14:
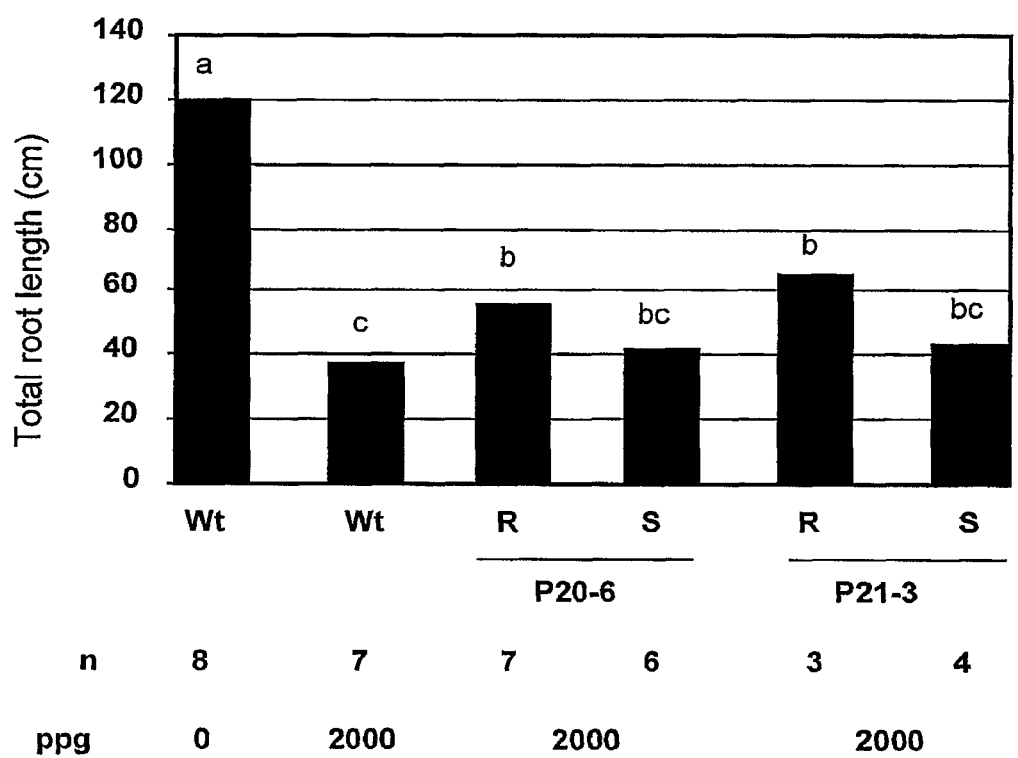
FIG. 14 shows, according to particular exemplary embodiments of the present invention, to validate the *Pythium* tolerance indicated by leaf measurements, plants from the R (strong tolerance) and S (susceptible) leaf length classes (see FIG. 13) were picked at random for root length analysis. The findings show that *Pythium* tolerance in BC1F2 plants of Scarlet Rz1 is indicated by enhanced root growth, as well as enhanced foliar growth.
Figure 15:
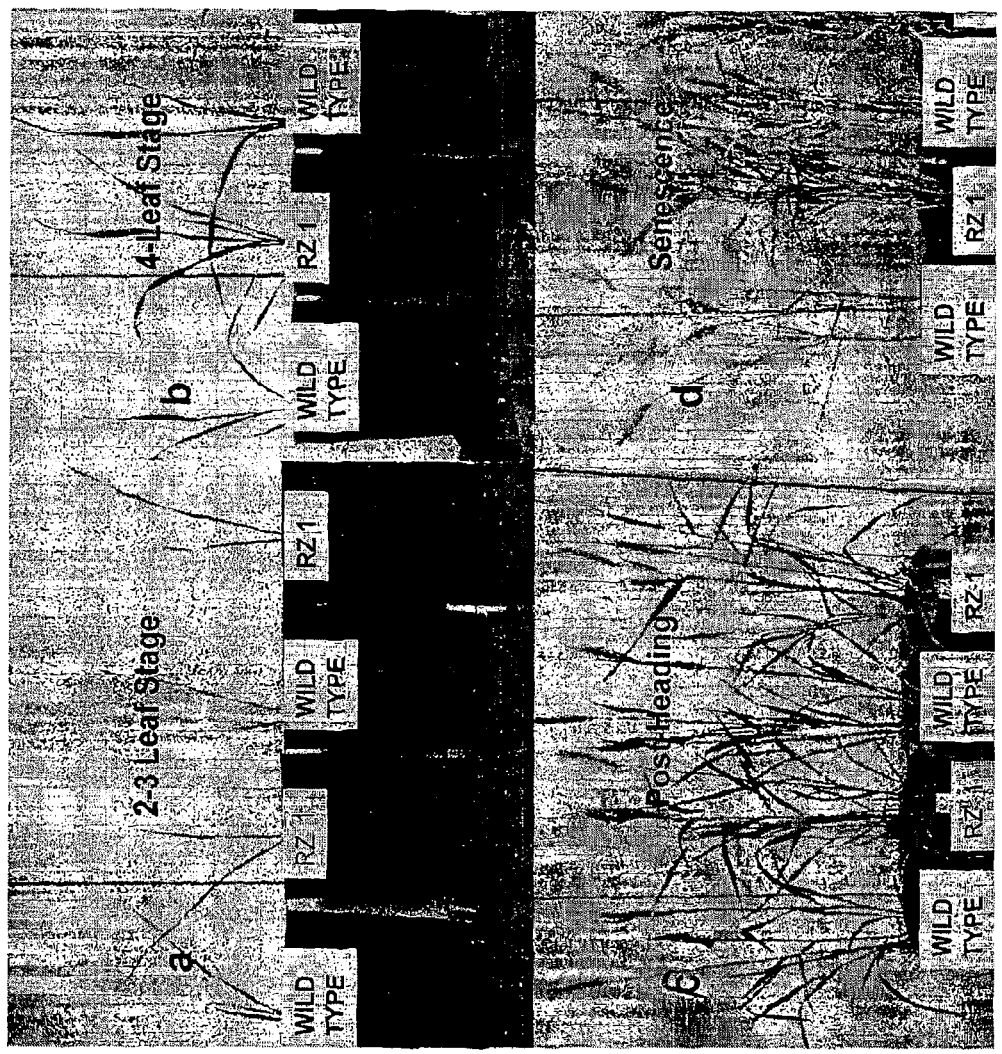
FIGS. 15A-D show, according to particular exemplary embodiments of the present invention, plant growth comparisons of wildtype (WT=unmutagenized) Scarlet and Rz1, the *Rhizoctonia* and *Pythium* root rot resistant mutant recovered from EMS mutagenesis of Scarlet at: a) 2-3 leaf stage; b) 4 leaf stage; c) post heading; and d) during senescence. No obvious phenotypic differences between WT Scarlet and Rz1 are evident at any growth stage.
Figure 16:
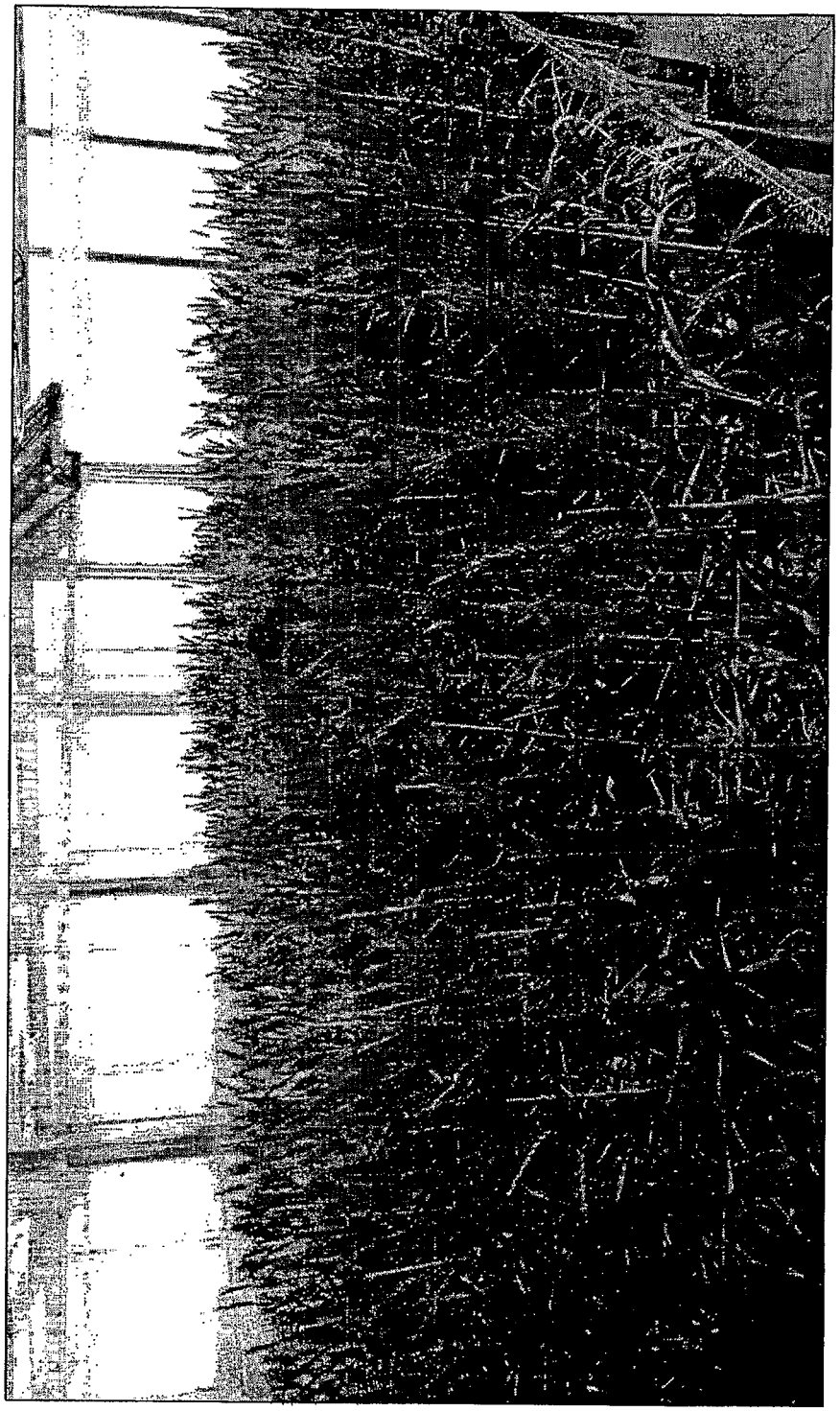
FIG. 16 shows, according to particular exemplary embodiments of the present invention, seed increase of Rz1 in the Wheat Research Facility at Washington State University in Pullman. Phenotypically, Rz1 is indistinguishable from non-mutagenized spring wheat under typical greenhouse growth conditions. Plants are vigorous, healthy and have high fertility levels.

Specifically, FIG. 14 shows, to validate the *Pythium* tolerance indicated by leaf measurements, plants from the R (strong tolerance) and S (susceptible) leaf length classes (see FIG. 13) were picked at random for root length analysis. Controls were wild type Scarlet (Wt) with and without inoculum. Letters indicate significant (P<0.05) differences among the means (LSD). As with leaf length values, root length values of tolerant (R) plants would be averaged with susceptible (S) plants, with no apparent overall tolerance if the sorting was omitted. In the R class, a small but significant (P<0.05) increase in root length was observed in *Pythium*-challenged BC1F2 plants compared to *Pythium*-challenged wild type Scarlet. A small degree of root length enhancement in tolerant plants is expected because other EMS mutations that reduce plant health are likely present in the BC1F2 generation; these would be eliminated in subsequent generations by gene or chromosome sorting. The findings show that *Pythium* tolerance in BC1F2 plants of Scarlet Rz1 is indicated by enhanced foliar as well as root growth.

Additional references are: Higginbotham, R. W., Paulitz, T. C, and Kidwell, K. K. 2004. Virulence of *Pythium* species isolated from wheat fields in eastern Washington. Plant Dis. 88: 1021-1026; Ongram, D. M. and Cook, R. J. 1990. Pathogenicity of four *Pythium* species to wheat, barley, peas and lentils. Plant Pathol. 39: 110-117; and Paulitz, T. C. and Adams, K. 2003. Composition and distribution of *Pythium* communities in wheat fields in eastern Washington state. Phytopathology 93: 867-873.

EXAMPLE 4

The Cultivar Scarlet was Chemically Mutagenized to Provide Novel Wheat Genotypes with Increased Drought Tolerance The Example describes isolation of drought tolerant wheat plants based on increased sensitivity to the plant hormone ABA (abscisic acid) during seed germination. The present applicants identified 19 independent mutants with increased drought tolerance. These lines were backcrossed to Chinese spring, and evaluated in a preliminary field trial at Spillman Farm in 2005. Four of the most promising mutants were crossed to the *Rhizoctonia* tolerant Scarlet mutant (see above) to provide for introducing these genes into adapted spring wheat germplasm.

Rationale. Low precipitation levels limit yield potential of both spring and winter wheat grown in Eastern Washington, and the development of drought tolerant varieties could result in increased grain yields in the Pacific Northwest (PNW), U.S.A.

Methods. The screen used to isolate drought tolerant wheat plants was based on previous work in the model plant *Arabidopsis* showing that plants with increased sensitivity to the plant hormone ABA during seed germination tend to be tolerant to drought stress. ABA is both the seed dormancy hormone and the drought tolerance hormone. ABA application inhibits seed germination in a concentration-dependent manner. Applicants screened for mutants that were unable to germinate on a concentration of ABA that is normally too low to inhibit seed germination. These "ABA hypersensitive" mutants are more sensitive to ABA in germination than normal plant. ABA is the signal from the roots to the shoots to conserve water as the soil dries. By making plants more sensitive to ABA, they are forced to conserve water earlier than normal. In the case of era1 mutants in *Arabidopsis* and in canola, this results in a high degree of drought tolerance.

Results. Applicants have characterized the drought tolerance of ABA hypersensitive mutants of Chinese spring, Scarlet, and Zak. The first screening was performed in a 'lab rat' wheat genotype called 'Chinese spring'. Of the 25 lines found to be ABA hypersensitive based on seed germination, 4 appeared to be drought tolerant using transpiration rate measurements. Based on segregation analysis of eight $BC_1F_2$ plants from backcross to normal Chinese spring, 4 mutations appeared to be semi-dominant, 2 dominant, and 1 recessive. Four putative drought tolerant plants have been crossed to the *Rhizoctonia* tolerant Scarlet mutant to provide for mapping genes associated with these traits and to deploy drought tolerance into adapted spring wheat germplasm. ABA hypersensitive plants were grown to evaluate the effect of these mutations on growth under dry conditions.

When the screen was repeated a total of 27 ABA hypersensitive mutants were isolated in Scarlet and 4 in Zak. Drought tolerance tests indicate that 5 of the 27 Scarlet and 1 of Zak lines show drought tolerance. The first backcross of 4 Zak and 14 Scarlet ABA hypersensitive lines has been completed.

EXAMPLE 5

Breeding Strategy for Deploying Fungal Root Pathogen Resistance in Rz1

The Example describes, according to further embodiments, forward breeding and backcross breeding strategies for deploying fungal root pathogen resistance in Rz1).

Based on the genetic segregation data disclosed herein, the *Rhizoctonia* root rot resistance in Rz1 is controlled by a single, dominant gene. According to additional aspects, the following strategy are used to deploy this gene into adapted spring wheat germplasm through traditional cross-hybridization techniques (Allard 1999). Since resistance is conferred by a single dominant gene, a 1 (homozygous resistant):2 (heterozygous):1 (homozygous susceptible) segregation ratio is expected among self-pollinated progeny from a heterozygous plant when challenged with the pathogens.

Forward Breeding

An adapted line (susceptible) is cross-hybridized to a $BC_2F_4$ homozygous derivative of Scarlet Rz1 (resistant) to create novel genetic combinations containing the resistance gene from Rz1. Seed is planted and resulting $F_1$ hybrid plants are allowed to self-pollinate and resulting F2 seed are harvested. Seed is planted and resulting $F_2$ plants re challenged with the pathogens to select resistant plants for advancement. Twenty-five percent of the $F_2$ progeny are expected to be homozygous resistant. These lines are self-pollinated, resulting $F_3$ seed is harvested, and a 40 g subsample is used to establish a single $F_3$ plot in the field. Single heads from 100-150 $F_3$ plants are threshed individually to establish $F_4$ head row families. Following selection for grain appearance, plant height, and general adaptation, seed from 30-50 plants within each selected head row are bulk harvested to obtain $F_5$ seed for early generation, end-use quality and disease response assessment. Prior to end-use quality assessment, seedlings from each selected $F_5$ bulk are assayed for resistance to *Rhizoctonia* and *Pythium* root rot in controlled environment assays. Resistant lines are then evaluated for end-use quality potential. Following selection for end-use quality, $F_5$ seed is used to establish single location field plots for initial yield evaluations during the following crop year. $F_6$ seed from high yielding lines is subjected to small-scale milling and baking analyses. Advanced lines ($F_7$) with superior agronomic and end-use quality potential are entered into preliminary yield trial evaluations where detailed notes on field performance, including grain yields, test weights, plant heights, heading dates, disease and insect resistance ratings and various quality characteristics, are recorded. Superior lines are selected and advanced to the next generation for field evaluation in replicated trials at multiple locations. Advanced lines with variety release potential are evaluated in the regional variety testing trials to assess agronomic performance in diverse environments for at least 2 years, targeting areas prone to damage to soil-borne fungal root pathogens. Experimental lines that equal or exceed agronomic and end-use quality standards over multiple site/years with demonstrated resistance to *Rhizoctonia* and/or *Pythium* root rots are released for commercial production.

Backcross Breeding

In particular aspects, a backcross strategy is used to introgress the resistance gene from Rz1 into agronomically superior adapted spring wheat varieties. An adapted line (susceptible recurrent parent) is cross-hybridized to a $BC_2F_4$ homozygous derivative of Scarlet Rz1 (resistant donor parent). Seed is planted and pollen from resulting $F_1$ hybrid (heterozygous) plants is used to pollinate the recurrent parent to produce $BC_1F_1$ seed. $BC_1F_1$ seed is planted and resulting plants are screened for resistance to *Rhizoctonia* root rot. A 1 (resistant (heterozygous)) to 1 (susceptible (homozygous)) segregation ratio is expected among $BC_1F_1$ progeny. Pollen from resistant $BC_1F_1$ plants is used to pollinate recurrent parent plants, to generate the $BC2F_1$ plants. Again, a 1 (resistant (heterozygous)) to 1 (susceptible (homozygous)) segregation ratio is expected among $BC_2F_1$ progeny. The cycle is repeated to create $BC_3F_1$ plants. $BC_3F_1$ plants are challenged by the pathogens, and resistant lines are allowed to self-pollinate. Individuals within resistant $BC_3F_2$ families are challenged with the pathogens to identify lines that are homozygous for the resistance gene. 25% of the $BC_3F_2$ are expected to be families to be homozygous resistant. $BC_3F_3$ seed from homozygous resistant lines is used to establish single plot field trials Agronomic and end-use quality potential is assessed as previously described. Allard, R. W. 1999. *Principles of Plant Breeding*. Second Edition. John Wiley and Sons, Inc., New York, N.Y.

EXAMPLE 6

Mapping the Rz1 Mutation; Marker Assisted Selection (MAS)

The Example describes, according to further embodiments, mapping of the Rz1 mutation to provide for Marker Assisted Selection (MAS).

Rationale. Biotechnology has revolutionized plant breeding by providing tools, such as molecular markers, which can be used in Marker-Assisted Selection (MAS) strategies to rapidly incorporate associated genes into improved varieties (Paterson et al. 1991). The development of molecular markers associated with beneficial traits offers an opportunity to assay genotypes during the breeding process to ensure that essential genes are in fact present in selected individuals. Molecular markers have been developed and used to introgress genes for resistance to various diseases into a wide array of crops (Paterson et al. 1991; Cenci et al. 1999; Naik et al. 1998; Paltridge et al. 1998; Quint et al. 2002; Ramalingam et al. 2002). The success and efficiency of using MAS depends upon how closely the marker is associated with the target gene of interest, and the ease with which the marker can be selected for among segregating progeny.

As described herein, traditional breeding approaches are used to incorporate Rz1 into adapted germplasm. Unfortunately, selecting for this trait is challenging because pathogen resistance assays are time-consuming and labor-intensive. Carefully-controlled conditions are required to conduct disease screening assays, and 3 weeks are required to collect resistance response data from 120 plants. To circumvent these problems, development of laboratory-based assays using DNA tags associated with Rz1 for use in Marker-Assisted Selection (MAS) strategies is desired, and such markers are useful in rapidly deploying this gene into adapted wheat germplasm. Using MAS will increase the rate of gene deployment by reducing the need to conduct disease evaluations in the growth chamber at every stage of early generation advancement. The presence of DNA tags associated with Rz1 can be monitored during the advancement process, eliminating the need to verify the tolerance response in the growth chamber until a manageable number of genotypes carrying the molecular markers for Rz1 have been identified. In such instances, disease response is confirmed through growth chamber analyses prior to field testing. With the ability to conduct MAS for Rz1, incorporation of the gene into fifth generation breeding material in an 18 month time span is possible.

Localization of Rz1 to a Chromosomal Segment:

The disease resistance in Scarlet-Rz1 is the result of a mutation created through EMS mutagenesis, which is know to generate C to T nucleic acid transitions and, less frequently, small chromosomal deletions. According to particular aspects, mutations that result in the creation of Rz1 results from a loss or change in function. Where Rz1 is the result of loss of gene function, it is possible to localize the gene to a chromosome location based on *Rhizoctonia* resistance reactions of wheat deletion lines (Qi et al. 2003; Sears 1966). This approach reveals the chromosomal region to focus on for fine-mapping efforts.

In particular aspects, Chinese Spring nullisomic-tetrasomic and deletion lines are screened (Qi et al. 2003; Sears 1966) for resistance to *Rhizoctonia* spp. to localize Rz1 to a chromosome segment. These lines are comprised of a wheat plant in which one whole chromosome has been lost and replaced with an extra copy of a homeologous chromosome. For example, a nulli-tetrasomic line might lack chromosome 3A, but would carry two copies of chromosome 3B. For purposes of illustration, if this line was resistant to *Rhizoctonia* root rot, this would suggest that Rz1 is located on chromosome 3A.

Wheat deletion lines. Once the *Rhizoctonia* resistant phenotype is localized to a chromosome, wheat deletion lines for that chromosome are used to further delineate the position of Rz1 (Qi et al. 2003; Sears 1966). Deletion lines are missing different segments of the same chromosome, and can be used to determine what segment of a chromosome a particular gene is located on through a process called deletion mapping. At least four individuals for each genetic stock are screened for resistance to *Rhizoctonia* root rot.

Disease screening procedures. *Rhizoctonia solani* AG-8 is used to determine the resistance reaction of genetic stocks (Paulitz et al. 2003). In particular aspects, pasteurized soil is infested with 1.5 g ground oat grain inoculum per 1000 g of rolled soil. Un-inoculated soil is also included as a control. Soil is placed in sterile containers with a cotton ball in the bottom to prevent soil loss. Soil is moistened with distilled water, and containers are be incubated in a growth room at 16° C. with a 14 hr day-length for 1 week to allow mycelium to colonize the soil. A pre-germinated seedling is transferred to each container. After 3 weeks, seedlings are removed, roots washed with a high pressure water stream, and plants are rated for pathogen damage based on plant height, severity of disease symptoms, percentage of infected seminal roots, root weight, and quantitative variables analyzed in WinRhizo using root scans to determine total root length, average root diameter (indicating amount of lateral roots) and number of root tips.

Identification of Molecular Markers Associated with Rz1 in a Double Haploid (DH) Population:

In additional aspects, molecular markers associated with Rz1 are identified in a double haploid (DH) population developed from a cross between Scarlet-Rz1 and its susceptible sibling Scarlet-S. In certain aspects, EMS mutagenesis generates changes (e.g., polymorphisms) in the DNA sequences flanking the Rz1 gene. Given the nature of EMS mutagenesis, these changes are likely to involve single nucleotides; however, small deletions also are possible. Such polymorphisms are expected to be located on the same chromosome as Rz1, either within or tightly associated with the gene itself. A molecular marker associated with such a polymorphism provides facilitation for monitoring for the presence of Rz1, since it represents a unique mutation event on the Rz1 chromosome, which should be absent from other wheat cultivars.

In particular aspects parental lines have been screened with 1116 SSRs, and 46 (4.1%) were determined to be polymorphic. According to particular aspects, these markers facilitate determining the genetic linkage map location and identifying DNA markers associated with Rz1. The 46 polymorphic SSR markers are used to initiate mapping efforts in an established double haploid mapping population.

Alternatively, parental lines are screened for polymorphisms using restriction site polymorphisms (Sequence Tagged Site (STS)) markers, and microarray-based Single Feature Polymorphisms (SFPs).

Screening for linked markers using conventional SSR and STS markers. Screening for polymorphisms between Scarlet-Rz1 and its susceptible sibling Scarlet-S is first performed using SSR and STS markers. Because these markers are easy to use, they are good initial screening tools. Rz1 is mapped to its chromosomal location through genetic linkage analysis as described by Anderson et al. (1992) to provide a molecular marker associated with the gene for use in MAS (Anderson 2000). Initial cross-hybridizations to create a segregating mapping population for DNA marker evaluation and trait analysis are made between resistant Scarlet-Rz1 and susceptible Scarlet-S. A mapping population of approximately 200 DH individuals derived through microspore culture (see section "c") is genotyped with polymorphic SSR markers (Stephenson et al. 1998). The mapping population is evaluated for disease responses to *R. solani* and *R. oryzae* in the growth chamber as described by Smith et al. 2003a The populations are also evaluated in replicated field trials in disease prone areas when adequate seed quantities are available. Trait data is co-aligned with marker data using MAPMAKER version 3.0 (Lander et al. 1987) to identify molecular markers associated with the resistance gene. Alternatively, SFP polymorphisms are screened for by using microarray analyses.

Microarray-based SFP markers. A polymorphism detected by a single probe in an oligonucleotide array is called a Single Feature Polymorphism (SFP), where a feature refers to a single probe in the array (West et al. 2006). Single nucleotide changes can lead to differences in signal intensity during microarray hybridization. Microarray analysis allows screening of over 100,000 probes to identify differences between genomic DNA samples isolated from parents of the mapping population. Once a polymorphism has been detected, it must be converted into a conventional marker in order to efficiently screen a large mapping population. Two venues are currently available for identifying polymorphisms using this method, the Diversity Array Technology (DArT) service and the Wheat Affymetrix Gene Chip (Akbari et al. 2006).

Generating the double haploid (DH) mapping population. Where a sufficient number of polymorphisms is detected between Scarlet-Rz1 and Scarlet-S, a DH mapping population is generated, derived from the cross of these two parent lines using microspore culture. Microspores are immature pollen and have the gametic number (n) of chromosomes. They can be induced to divide and to form embryos or calli, which provide an efficient source of double haploid plants. Double haploids are genetically homozygous and produce pure breeding lines, which can be used for linkage map construction. The protocol of Kasha et al. (2003) can be used to establish the microspore culture technique, which involves: a) collecting tillers of $F_1$ plants at the mid-to late-uninucleate stage; b) pre-treatment of 1 to 6 tillers under laminar flow hood in a petridish (150 mm×15 mm) containing sterile 0.4M mannitol solution followed by incubation in the dark at 4° C. for 7-10 days; c) microspore isolation, which involves: 1) grinding pretreated spikes in mannitol solution followed by separation of interphase (band of viable embryogenic microspores) created by maltose/mannitol density gradient centrifugation technique, purification of microspores and transferring them to culture medium at an optimum cell density; and (2) transferring resulting embryoides to regeneration medium to obtain green plantlets. Green plantlets can be recovered in 5 to 6 weeks using this procedure.

Disease screening. All individuals in the DH mapping population are screened for disease reaction to *Rhizoctonia* spp. as described above. At least 4 individual plants per DH line are evaluated.

Fine-Mapping Rz1 using SSR Markers to Evaluate a DH Population Generated from a Cross Between Scarlet-Rz1 and Chinese Spring:

In particular aspects, Chinese Spring was chosen as a mapping parent because preliminary parental screening results indicated that a significant portion of the markers evaluated were polymorphic between Chinese Spring and Scarlet-Rz1, and because mapping results generated using Chinese Spring as a parent would be expected to align with results from the deletion mapping approach described. Substantial genetic and genomic resources derived from Chinese Spring also are available to assist in gene mapping and cloning. Where the chromosome or chromosome region that contains Rz1 is identified, mapping efforts are focused on SSR markers within the chromosome region known to contain Rz1. This approach is used to accurately determine the position of Rz1 relative to markers on currently published wheat genetic and physical maps. Knowing the Rz1 map position is useful for determining what other genes or markers of interest are located in that chromosomal region. Where a marker linked to Rz1 is identified, this marker is mapped relative to polymorphic SSRs to accelerate the mapping process.

Mapping relative to SSR markers. In particular aspects, Rz1 is mapped relative to polymorphic SSR markers using DH lines derived from the cross of the resistant parent Scarlet-Rz1 and the susceptible parent Chinese Spring. A collection of at least 300 SSRs is used to screen the parents for polymorphism detection. Mapping is performed as described above.

Generating the DH mapping population. In certain aspects, a mapping population consisting of 250 to 500 DH lines derived from the pollen of 50 to 100 $F_1$ plants is used to develop this mapping population as described above.

Disease screening. All individuals in the DH mapping populations are screened for disease reaction to *Rhizoctonia* spp. as described above. At least 4 individual plants per DH line are evaluated. Alternatively, markers such as STS markers are used.

In particular aspects, therefore, the chromosomal location of the *Rhizoctonia* root rot resistance gene Rz1 is determined, and molecular markers closely associated with this trait are identified. These markers are used to assay for the presence of Rz1 among segregating progeny through MAS, which eliminates the need to conduct laborious growth chamber screening assays to identify resistant genotypes among large numbers of individuals from breeding populations in early stages of advancement. In further aspects, the markers accelerate the rate of development of *Rhizoctonia* root rot resistant wheat varieties targeted to direct-seeded production conditions. In such aspects, the risk of crop loss due to *Rhizoctonia* damage is eliminated, thereby increasing profit potential, enabling more growers to take advantage of the environmental advantages associated with direct-seeded spring wheat production.

Literature Cited:

Akbari, M., P. Wenzl, V. Caig, J. Carling, L. Xia, S. Yang, G. Uszynski, V. Mohler, A. Lehmensiek, H. Kuchel, M. Hayden, N. Howes, P. Sharp, P. Vaughan, B. Rathmell, E. Huttner and A. Kilian. 2006. Diversity arrays technology (DArT) for high-throughput profiling of the hexaploid wheat genome. Theor. Appl. Genet. 113:1409-1420.

Anderson, J. A., Y. Ogihara, M. E. Sorrells and S. D. Tanksley. 1992. Development of a chromosomal arm map for wheat based on RFLP markers. Theor. Appl. Genet. 83:1035-1043.

Anderson, J. 2000. Marker-Assisted selection of disease resistance genes in wheat. In "Application of Biotechnologies to Wheat Breeding". M M Kohli and M Francis, Editors: La Estanzuela, Uruguay. 71-84.

Bockus, W. W. and J. P. Shroyer. 1998. The impact of reduced tillage on soilborne plant pathogens. Annual Review of Phytopathology 36:485-500.

Cenci, A., D'Ovidio, R., Tanzarella, O. A., Ceoloni, C. and Porceddu, E. 1999. Identification of molecular markers linked to Pm13, an *Aegilops longissima* gene conferring resistance to powdery mildew in wheat. Theor. Appl. Genet. 98:448-454.

Cotterill, P. J. 1990. Assessment of yield loss caused by *Rhizoctonia* root rot in a barley crop sown following cultivation at Nhill Northwest Victoria, Australia. Australas. Plant Pathology 19:77-78

Cotterill, P. J., D. J. Ballinger and J. F. Kollmorgen. 1989. Use of three screening techniques for the evaluation of fungicides to control *Rhizoctonia* root rot of wheat. Annals of Applied Biology 115:229-235.

Kasha K. J., E. Simion, M. Miner, J. Letarte and T. C. Hu. 2003. Haploid wheat isolated microspore culture protocol. pp 77-81 In: M. Maluszynski, K. J. Kasha, B. P. Forster and I. Szarejko (eds). Doubled Haploid Production in Crop Plants, a Manual. Kluwer Academic, Dordrecht, Boston and London.

Kidwell, K. K., G. B. Shelton, C. F. Morris, R. F. Line, B. C. Miller, M. A. Davis and C. F. Konzak. 1999. Registration of 'Scarlet' Wheat. Crop Sci. 39:1255.

Konzak, C. F. 1987. Mutations and mutation Breeding. pp. 428-443. In Heyne, E. G. (ed), Wheat and Wheat Improvement. Agronomy Monograph 13. ASA, CSSA, and SSSA, Madison, Wisc.

Lander, E. S., P. Green, J. Abrahamson, A. Barlow, M. J. Daly, S. E. Lincoln and L. Newburg. 1987. MAPMAKER: An interactive computer package for constructing primary genetic linkage maps of experimental and natural populations. Genomics 1: 174-181.

MacNish, G. C. 1985. Methods of reducing *Rhizoctonia* bare patch of cereals in western Australia. Plant Pathology 34:175-181.

Naik, S., K. S. Gill, V. S. Prakasa Rao, V. S. Gupta, S. A. Tamhankar, S. Pujar, B. S. Gill and P. K. Ranjekar. 1998. Identification of a STS marker linked to the *Aegilops speltoides*-derived leaf rust resistance gene Lr28 in wheat. Theor. Appl. Genet. 97:535-540.

Paltridge, N. G., N. C. Collins, A. Bendahmane and R. H. Symons. 1998. Development of YLM, a codominant PCR marker closely linked to the Yd2 gene for resistance to barley yellow dwarf disease. Theor. Appl. Genet. 96:1170-1177.

Pannkuk, C. D., R. I., Papendick and K. E. Saxton. 1997. Fallow management effects of soil water storage and wheat yields in the Pacific Northwest. Agronomy Journal 89:386-391

Paterson, A. H., S. D. Tanksley and M. E. Sorrells. 1991. DNA markers in plant improvement. Advances in Agronomy 46:39-90.

Paulitz, T. C., J. D. Smith and K. K. Kidwell. 2003. Virulence of *Rhizoctonia oryzae* on wheat and barley cultivars from the Pacific Northwest. Plant Dis. 87:51-55.

Pumphrey, F. V., D. E. Wilkins, D. C. Hane and R. W Smiley. 1987. Influence of tillage and nitrogen fertilizer on *Rhizoctonia* root rot (bare patch) of winter wheat. Plant Disease 71:125:127.

Qi, L. B. Echalier, B. Friebe and B. Gill. 2003. Molecular characterization of a set of wheat deletion stocks for use in chromosome bin mapping of ESTs. Funct. Integr. Genomics 3:39-55.

Quint, M., R. Mihaljevic, C. M. Dussle, M. L. Xu, A. E. Melchinger and T. Lubberstedt. 2002. Development of RGA-CAPS markers and genetic mapping of candidate genes for sugarcane mosaic virus resistance in maize. Theor. Appl. Genet. 105:355-363.

Ramalingam, J., H. S. Basharat and G. Zhang. 2002. STS and microsatellite marker-assisted selection for bacterial blight resistance and waxy genes in rice, *Oryza sativa* L. Euphytica 127:255-260.

Rovira, A. D. 1986. Influence of crop rotation and tillage on *Rhizoctonia* bare patch of wheat. Phytopathology 76:669:673.

Sears, E. R. 1966 Nullisomic-tetrasomic combinations in hexaploid wheat. In: Rilly R, Lewis, K R (eds) Chromosome manipulations and plant genetics. Oliver and Boyd, Edinburgh, pp 29-45.

Smiley, R. W. 1996. Diseases of wheat and barley in conservation cropping systems of the semiarid Pacific Northwest. American Journal of Alternative Agriculture 11:95-103.

Smiley, R. W. and W. Uddin. 1993. Influence of soil temperature on *Rhizoctonia* root rot (*R. solani* AG-8 and *R. oryzae*) of winter wheat. Phytopathology 83:777-785.

Smiley, R. W., D. Wilkins, W. Uddin, S. Ott, K. Rhinhart and S. Case. 1989. *Rhizoctonia* root rot of wheat and barley. Oregon Agricultural Experiment Station Special Report 840:68-79.

Smiley, R. W., D. Wilkins, W. Uddin, S. Ott, K. Rhinhart and S. Case. 1990. Influence of Flutolanil and tolcofos-methyl on root and culm diseases of winter wheat. Plant Disease 74:788-791.

Smith, J. D., K. K. Kidwell, M. A. Evans, R. J. Cook and R. W. Smiley. 2003a. Assessment of spring wheat genotypes for disease reaction to *Rhizoctonia solani* AG-8 in controlled environment and direct-seeded field evaluations. Crop Sci. 43:694-700.

Smith, J. D., K. K. Kidwell, M. A. Evans, R. J. Cook and R. W. Smiley. 2003b. Evaluation of spring cereal grains and wild *Triticum* germplasm for resistance to *Rhizoctonia solani* AG-8. Crop Sci. 43:701-709.

Stephenson, P., G. Bryan, J. Kirby, A. Collins, K. Devos, C. Busso and M. Gale. 1998. Fifty new microsatellite loci for the wheat genetic map. Theor. Appl. Genet. 97:946-949.

Weller, D. M. R. J. Cook, G. MacNish, E. N. Bassett, R. L. Powelson and R. R. Petersen. 1986. *Rhizoctonia* root rot of small grains favored by reduced tillage in the Pacific Northwest. Plant Disease 70:70-73.

West, M., H. van Leeuwen, A. Kozik, D. Kliebenstein, R. Doerge, D. St. Clair and R. Michelmore. 2006. High-density haplotyping with microarray-based expression and single feature polymorphism markers in *Arabidopsis*. Genome Research 16:787-795.

The foregoing invention has been described in detail by way of illustration and example for purposes of clarity and understanding. However, it will be obvious that certain changes and modifications such as single locus modifications and mutations, somoclonal variants, variant individuals selected from large populations of the plants of the instant variety and the like may be practiced within the scope of the invention.

All publications, patents and patent applications mentioned in the specification are indicative of the level of those skilled in the art to which this invention pertains. All such publications, patents and patent applications are incorporated by reference herein for the purpose cited to the same extent as if each was specifically and individually restated herein.

The invention claimed is:

1. A wheat plant or a part thereof, comprising a semi-dominant mutation that confers root fungal tolerance to at least one root fungal pathogen selected from the group consisting of *Rhizoctonia* and *Pythium*, wherein the semi-dominant mutation is from a root fungal pathogen-tolerant wheat genotype resulting from ethyl methane sulfonate (EMS) mutagenesis of wheat germplasm, wherein the root fungal pathogen-tolerant wheat genotype is tolerant to at least one root fungal pathogen selected from the group consisting of *Rhizoctonia* and *Pythium*.

2. The wheat plant or part thereof claim 1, wherein the root fungal pathogen-tolerant wheat genotype is Scarlet-Rz1, representative sample of seed of said wheat plant having been deposited under ATCC Patent Deposit Number PTA-8198.

3. The wheat plant or part thereof of claim 1, obtained by crossing a plant of the root fungal pathogen-tolerant wheat genotype with a plant of a wheat variety that lacks the root fungal pathogen-tolerance trait to produce progeny, and selecting the wheat plant comprising the root fungal pathogen-tolerance trait from the progeny.

4. The wheat plant or part thereof of claim 1, wherein the *Rhizoctonia* spp comprises at least one selected from the group consisting of *R. solani* and *R. oryzae*.

5. The wheat plant or part thereof of claim 1, wherein the *Pythium* spp comprises at least one selected from the group consisting of *P. ultimum, P. irregulare, P. debaryanum, P. aristosporum, P. volutum*, and *P. sylvaticum*.

6. The wheat plant or part thereof of claim 1, further comprising at least one trait selected from the group consisting of: male sterility, resistance to an herbicide, insect resistance, disease resistance; waxy starch; modified fatty acid metabolism, modified phytic acid metabolism, modified carbohydrate metabolism, modified waxy starch content, modified gluten content, and modified water stress tolerance.

7. The wheat plant or part thereof of claim 6, wherein the herbicide consists of or comprises glyphosate or a derivative thereof.

8. A seed of a root fungal pathogen-tolerant wheat genotype, the root fungal pathogen-tolerant wheat genotype resulting from ethyl methane sulfonate (EMS) mutagenesis of wheat germplasm, wherein the root fungal pathogen-tolerant wheat genotype is tolerant to at least one root fungal pathogen selected from the group consisting of *Rhizoctonia* and *Pythium*.

9. The seed of claim 8, wherein the root fungal pathogen-tolerant wheat genotype is Scarlet-Rz, representative sample of seed of said wheat plant having been deposited under ATCC Patent Deposit Number PTA-8198.

10. The seed of claim 8, wherein the seed is a true-breeding seed.

11. A wheat plant or part thereof produced by growing the seed of claim 10.

12. The wheat plant or part thereof of claim 11, having all the physiological and morphological characteristics of a Scarlet-Rz1 genotype, representative sample of seed of said wheat plant having been deposited under ATCC Patent Deposit Number PTA-8198.

13. A method of making a root fungal pathogen-tolerant wheat genotype or wheat plant, comprising:
  providing germplasm of a wheat variety;
  treating the germplasm with ethyl methane sulfonate (EMS) mutagen to produce a mutagenized germplasm;
  selecting from the mutagenized germplasm a root fungal pathogen-tolerant wheat seed comprising a genotype conferring root fungal pathogen-tolerance that is caused by the mutagen; and
  growing a root fungal pathogen-tolerant wheat plant from the root fungal pathogen-tolerant wheat seed, wherein the root fungal pathogen-tolerant wheat genotype is tolerant to at least one root fungal pathogen selected from the group consisting of *Rhizoctonia* and *Pythium*.

14. The method of claim 13, wherein the germplasm consists of or comprises a plurality of seeds.

15. The method of claim 13, wherein the genotype conferring root fungal pathogen-tolerance comprises at least one mutation selected from the group consisting of a point mutation and a deletion mutation.

16. The method of claim 13, wherein the genotype conferring root fungal pathogen-tolerance comprises a semi-dominant mutation.

17. The method of claim 13, wherein the root fungal pathogen-tolerant wheat seed is identified by growing the root fungal pathogen-tolerant plant from the root fungal pathogen-tolerant wheat seed under conditions suitable to expose roots thereof to a root fungal pathogen, and observing the roots or the growth of the root fungal pathogen-tolerant plant during or after exposure to the root fungal pathogen.

18. The method of claim 13, wherein the *Rhizoctonia* spp comprises at least one selected from the group consisting of *R. solani* and *R. oryzae*.

19. The method of claim 13, wherein the *Pythium* spp comprises at least one selected from the group consisting of *P. ultimum*, *P. irregulare*, *P. debaryanum*, *P. aristosporum*, *P. volutum*, and *P. sylvaticum*.

20. The method of claim 13, wherein the root fungal pathogen-tolerant wheat plant is phenotypically similar to an unmutagenized wheat plant of the selected wheat variety.

21. A method of making a root fungal pathogen-tolerant wheat genotype or wheat plant, comprising:
  providing a plurality of seeds of a selected wheat variety;
  treating the plurality of wheat seeds with a ethyl methane sulfonate (EMS) mutagen to produce a mutagenized germplasm;
  selecting from the plurality of mutagenized wheat seeds a root fungal pathogen-tolerant wheat seed comprising a genotype conferring root fungal pathogen-tolerance that is caused by the mutagen; and
  growing a root fungal pathogen-tolerant wheat plant from the root fungal pathogen-tolerant wheat seed, wherein the root fungal pathogen-tolerant wheat plant is phenotypically similar to an unmutagenized wheat plant of the selected wheat variety, wherein the root fungal pathogen-tolerant wheat genotype is tolerant to at least one root fungal pathogen selected from the group consisting of *Rhizoctonia* and *Pythium*.

22. The method of claim 21 wherein the *Rhizoctonia* spp comprises at least one selected from the group consisting of *R. solani* and *R. oryzae*.

23. A method of producing a root fungal pathogen-tolerant wheat genotype or plant, comprising:
  crossing a plant of a selected wheat variety with a root fungal pathogen-tolerant wheat plant having a genotype of a root fungal pathogen-tolerant wheat genotype resulting from ethyl methane sulfonate (EMS) chemical mutagenesis of wheat germplasm, thereby producing a plurality of progeny; and
  selecting a progeny that is root fungal pathogen-tolerant, wherein the root fungal pathogen-tolerant wheat genotype is tolerant to at least one root fungal pathogen selected from the group consisting of *Rhizoctonia* and *Pythium*.

24. The method of claim 23, wherein the root fungal pathogen-tolerant wheat genotype is that of Scarlet-Rz1, representative sample of seed of said wheat plant having been deposited under ATCC Patent Deposit Number PTA-8198.

25. The method of claim 23, comprising:
  (a) crossing plants grown from seed of the root fungal pathogen-tolerant wheat genotype, with plants of the selected wheat variety to produce F1 progeny plants;
  (b) selecting F1 progeny plants that have the root fungal pathogen-tolerance trait;
  (c) crossing the selected F1 progeny plants with the plants of the selected wheat variety to produce backcross progeny plants;
  (d) selecting for backcross progeny plants that have the root fungal pathogen-tolerance trait and physiological and morphological characteristics of said selected wheat genotype to produce selected backcross progeny plants; and
  (e) repeating steps (c) and (d) three or more times in succession to produce selected fourth or higher backcross progeny plants that comprise the root fungal pathogen-tolerance trait and physiological and morphological characteristics of said selected wheat genotype as determined at the 5% significance level when grown in the same environmental conditions.

26. The method of claim 23, comprising:
  (a) crossing plants grown from seed of the root fungal pathogen-tolerant wheat genotype, with plants of said selected wheat variety to produce F1 progeny plants, wherein the selected wheat variety comprises a desired trait;

(b) selecting F1 progeny plants that have the desired trait to produce selected F1 progeny plants;

(c) crossing the selected progeny plants with the plants of the root fungal pathogen-tolerant wheat genotype to produce backcross progeny plants;

(d) selecting for backcross progeny plants that have the desired trait and physiological and morphological characteristics of the root fungal pathogen-tolerant wheat genotype to produce selected backcross progeny plants; and (e) repeating steps (c) and (d) three or more times in succession to produce selected fourth or higher backcross progeny plants that comprise the desired trait and physiological and morphological characteristics of said root fungal pathogen-tolerant wheat genotype as determined at the 5% significance level when grown in the same environmental conditions.

27. The method of claim 26, wherein the desired trait comprises at least one selected from the group consisting of: male sterility, resistance to an herbicide, insect resistance, disease resistance; waxy starch; modified fatty acid metabolism, modified phytic acid metabolism, modified carbohydrate metabolism, modified waxy starch content, modified gluten content, and modified water stress tolerance.

28. The method of claim 26, wherein the herbicide consists of or comprises glyphosate or a derivative thereof.

* * * * *